United States Patent
Bidwell, III et al.

(10) Patent No.: US 11,564,991 B2
(45) Date of Patent: *Jan. 31, 2023

(54) MOLECULAR-SIZE OF ELASTIN-LIKE POLYPEPTIDE DELIVERY SYSTEM FOR THERAPEUTICS MODULATES INTRARENAL DEPOSITION AND BIOAVAILABILITY

(71) Applicant: University of Mississippi Medical Center, Jackson, MS (US)

(72) Inventors: Gene L. Bidwell, III, Brandon, MS (US); Alejandro R. Chade, Brandon, MS (US)

(73) Assignee: University of Mississippi Medical Center, Jackson, MS (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/834,715

(22) Filed: Mar. 30, 2020

(65) Prior Publication Data

US 2020/0360527 A1     Nov. 19, 2020

Related U.S. Application Data

(63) Continuation-in-part of application No. 16/397,962, filed on Apr. 29, 2019, which is a continuation of application No. 15/517,805, filed as application No. PCT/US2015/060438 on Nov. 12, 2015, now Pat. No. 10,322,189.

(60) Provisional application No. 62/826,413, filed on Mar. 29, 2019, provisional application No. 62/078,752, filed on Nov. 12, 2014.

(51) Int. Cl.
    *A61K 47/64*     (2017.01)
    *A61K 38/18*     (2006.01)
    *A61P 13/12*     (2006.01)
    *A61K 38/39*     (2006.01)

(52) U.S. Cl.
    CPC .......... *A61K 47/64* (2017.08); *A61K 38/1866* (2013.01); *A61K 38/39* (2013.01); *A61K 47/6435* (2017.08); *A61P 13/12* (2018.01)

(58) Field of Classification Search
None
See application file for complete search history.

(56) References Cited

U.S. PATENT DOCUMENTS

| | | | |
|---|---|---|---|
| 7,527,792 | B1 | 5/2009 | Temsamani et al. |
| 10,081,667 | B2 * | 9/2018 | Bidwell, III ....... A61K 47/6435 |
| 10,322,189 | B2 * | 6/2019 | Chade, III ......... A61K 47/6435 |
| 2008/0032400 | A1 | 2/2008 | Dagher |
| 2010/0022466 | A1 | 1/2010 | Raucher |
| 2010/0119529 | A1 | 5/2010 | Furgeson et al. |
| 2011/0110866 | A1 | 5/2011 | Chilkoti et al. |
| 2013/0172274 | A1 | 7/2013 | Chilkoti |
| 2014/0323315 | A1 | 10/2014 | Bobrowicz et al. |

FOREIGN PATENT DOCUMENTS

| | | | |
|---|---|---|---|
| WO | WO97/10507 A1 | 3/1997 | |
| WO | WO2014/014613 A3 | 1/2013 | |
| WO | WO-2015051001 A2 * | 4/2015 | ............. C07K 14/49 |

OTHER PUBLICATIONS

Bidwell, et al., A kidney-selective biopolymer for targeted drug delivery, Am J Physiol Renal Physiol 312: F54-F64, 2017.
Chade, et al., Renal Therapeutic Angiogenesis Using a Bioengineered Polymer-Stabilized Vascular Endothelial Growth Factor Construct, J Am Soc Nephrol 27: 1741-1752, 2016.
Chade, et al., Systemic biopolymer-delivered vascular endothelial growth factor promotes therapeutic angiogenesis in experimental renovascular disease, Kidney International (2018) 93, 842-854.
Pasqualini R, Ruoslahti E (1996) Organ targeting in vivo using phage display peptide libraries. Nature 380:364-6. doi: 10.1038/380364a0.
Chade AR, Keisen S (2010) Renal microvascular disease determines the responses to revascularization in experimental renovascular disease. Circ Cardiovasc Interv 3:376-383.
Chade AR, Keisen S (2012) Reversal of renal dysfunction by targeted administration of VEGF into the stenotic kidney: a novel potential therapeutic approach. Am J Physiol Ren Physiol 302:F1342-50.
Iliescu R, Fernandez SR, Keisen S, et al. (2010) Role of renal microcirculation in experimental renovascular disease. Nephrol Dial Transplant Off Publ Eur Dial Transpl Assoc—Eur Ren Assoc 25:1079-1087.
Chade, et al., Molecular targeting of renal inflammation using drug delivery technology to inhibit NF-B improves renal recovery in chronic kidney disease, Am J Physiol Renal Physiol 319: F139-F148, 2020.
Mahdi, et al., Utilizing a Kidney-Targeting Peptide to Improve Renal Deposition of a Pro-Angiogenic Protein Biopolymer, Pharmaceutics 2019, 11, 542, pp. 1-21.

(Continued)

*Primary Examiner* — Christina Bradley
(74) *Attorney, Agent, or Firm* — Stites & Harbison PLLC; Richard S. Myers, Jr.

(57) ABSTRACT

A renal cortex targeting elastin-like polypeptide (ELP), a renal medulla and cortex targeting ELP, and a method of treating a renal disorder are provided. The renal cortex targeting ELP includes up to 95 repeat units having the sequence VPGXG (SEQ ID NO: 1), where X in each of the repeat units is any amino acid except proline. The renal medulla and cortex targeting ELP includes at least 95 repeat units of SEQ ID NO: 1, where X in each of the repeat units is any amino acid except proline. The method of treating a renal disorder includes administering an ELP and a therapeutic drug to a subject in need thereof, where the ELP includes up to 671 repeat units of SEQ ID NO: 1 and X in each of the repeat units is any amino acid except proline.

11 Claims, 22 Drawing Sheets

Specification includes a Sequence Listing.

(56) References Cited

OTHER PUBLICATIONS

Engel, et al., Targeted VEGF (Vascular Endothelial Growth Factor) Therapy Induces Long-Term Renal Recovery in Chronic Kidney Disease via Macrophage Polarization, Hypertension, 2019, pp. 1113-1123.

Guise, et al., Biopolymer-delivered vascular endothelial growth factor improves renal outcomes following revascularization, Am J Physiol Renal Physiol 316: F1016-F1025, 2019.

Kuna, et al., Molecular Size Modulates Pharmacokinetics, Biodistribution, and Renal Deposition of the Drug Delivery Biopolymer Elastin-like Polypeptide, Scientific Reports (2018) 8:7923, pp. 1-12.

Logue, et al., Therapeutic angiogenesis by vascular endothelial growth factor supplementation for treatment of renal disease, Curr Opin Nephrol Hypertens 2016, 25:404-409.

Massodi, et al., Evaluation of Cell Penetrating Peptides Fused to Elastin-Like Polypeptide for Drug Delivery; Journal of Controlled Release; 108; 2005; pp. 396-408.

Dreher, et al., Evaluation of an elastin-like polypeptide-doxorubicin conjugate for cancer therapy; Journal of Controlled Release; 91; 2003; pp. 31-43.

Meyer, et al., Targeting a genetically engineered elastin-like polypeptide to solid tumors by local hyperthermia; Cancer Research; 61; pp. 1548-1554; Feb. 15, 2001.

Rousselle C, Clair P, Lefauconnier JM, et al. (2000) New advances in the transport of doxorubicin through the blood-brain barrier by a peptide vector-mediated strategy. Mol Pharmacol 57:679-86.

Vives E, Brodin P, Lebleu B (1997) A truncated HIV-1 Tat protein basic domain rapidly translocates through the plasma membrane and accumulates in the cell nucleus. J Biol Chem 272:16010-7.

Ritchie J, Green D, Chrysochou C, et al. (2014) High-risk clinical presentations in atherosclerotic renovascular disease: prognosis and response to renal artery revascularization. Am J Kidney Dis Off J Natl Kidney Found 63:186-197. doi: 10.1053/j.ajkd.2013.07.020.

Textor SC, Lerman LO (2014) Reality and renovascular disease: when does renal artery stenosis warrant revascularization? Am J Kidney Dis Off J Natl Kidney Found 63:175-177. doi: 10.1053/j.ajkd.2013.11.004.

Textor SC, Misra S, Oderich GS (2013) Percutaneous revascularization for ischemic nephropathy: the past, present, and future. Kidney Int 83:28-40. doi: 10.1038/ki.2012.363.

Cooper CJ, Murphy TP, Cutlip DE, et al. (2014) Stenting and medical therapy for atherosclerotic renal-artery stenosis. N Engl J Med 370:13-22 doi: 10.1056/NEJMoa1310753.

Chade AR, Keisen S (2010) Renal microvascular disease determines the responses to revascularization in experimental renovascular disease. Circ Cardiovasc Interv 3:376-383. doi: 10.1161/CIRCINTERVENTIONS.110.951277.

Chade AR, Keisen S (2012) Reversal of renal dysfunction by targeted administration of VEGF into the stenotic kidney: a novel potential therapeutic approach. Am J Physiol Ren Physiol 302:F1342-50. doi: 10.1152/ajprenal.00674.2011.

Iliescu R, Fernandez SR, Kelsen S, et al. (2010) Role of renal microcirculation in experimental renovascular disease. Nephrol Dial Transplant Off Publ Eur Dial Transpl Assoc—Eur Ren Assoc 25:1079-1087. doi: 10.1093/ndt/gfp605.

Chade AR, Zhu X, Lavi R, et al. (2009) Endothelial progenitor cells restore renal function in chronic experimental renovascular disease. Circulation 119:547-557. doi: 10.1161/CIRCULATIONAHA.108.788653.

Textor, et al.; Renal Artery Stenosis: Medical Versus Interventional Therapy; Curr Cardiol Rep (2013) 15:409; pp. 1-7.

Chade, et al.; Renal Therapeutic Angiogenesis Using a Bioengineered Polymer-Stabilized Vascular Endothelial Growth Factor Construct; J Am Soc Nephrol 27; 2015; pp. 1-12.

Stewart, et al.; Renoprotective effects of hepatocyte growth factor in the stenotic kidney; 2013; Am J Physiol Renal Physiol 304: F625-F633.

Bidwell, et al.; Thermally Targeted Delivery of a c-Myc Inhibitory Polypeptide Inhibits Tumor Progression and Extends Survival in a Rat Glioma Model; PLOS ONE; 2013; vol. 8; Issue 1; pp. 1-12.

Bidwell, et al.; A thermally targeted c-Myc inhibitory polypeptide inhibits breast tumor growth; Cancer Letters 319 (2012) 136-143.

Bidwell, et al.; A kidney-selective biopolymer for targeted drug delivery; 2017; Am J Physiol Renal Physiol 312: F54-F64.

George, et al., A polypeptide drug carrier for maternal delivery and prevention of fetal exposure; 2014; J Drug Target, Early Online: 1-13.

George, et al., Growth factor purification and delivery systems (PADS) for therapeutic angiogenesis; Vascular Cell (2015) 7:1; pp. 1-10.

* cited by examiner

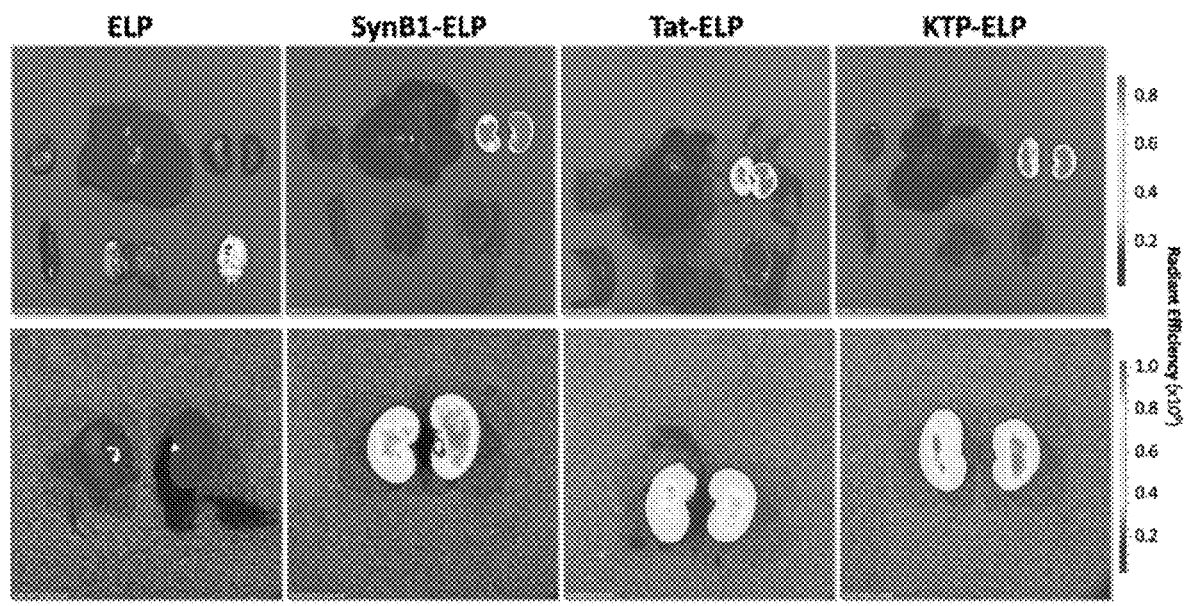
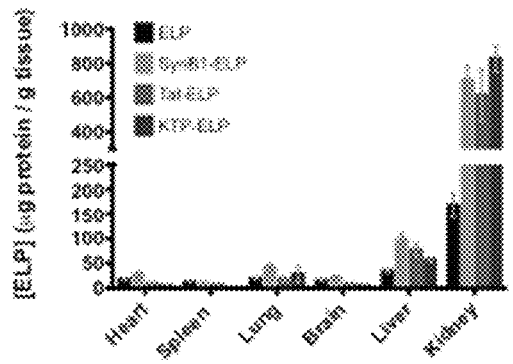
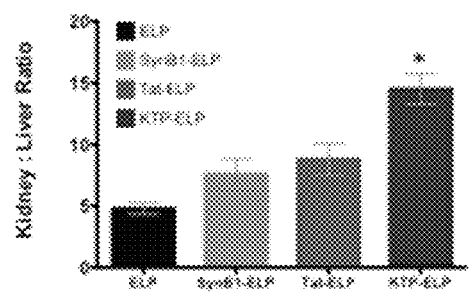
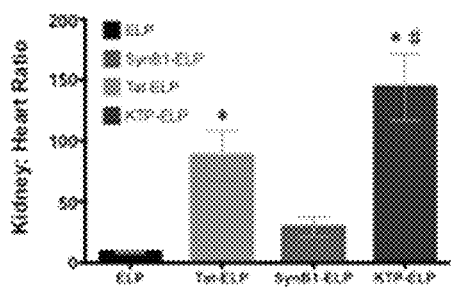
FIG. 2A
FIG. 2B
FIG. 2C
FIG. 2D

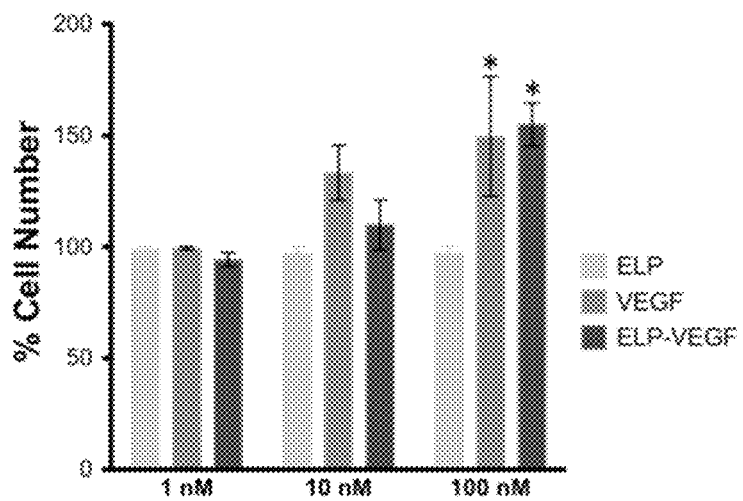
FIG. 8A
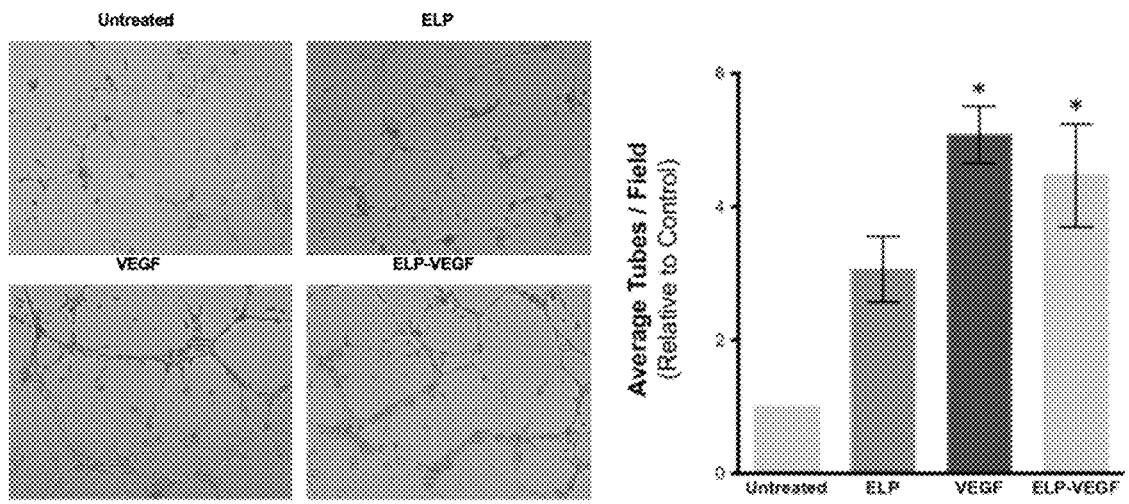
FIG. 8B
FIG. 8C
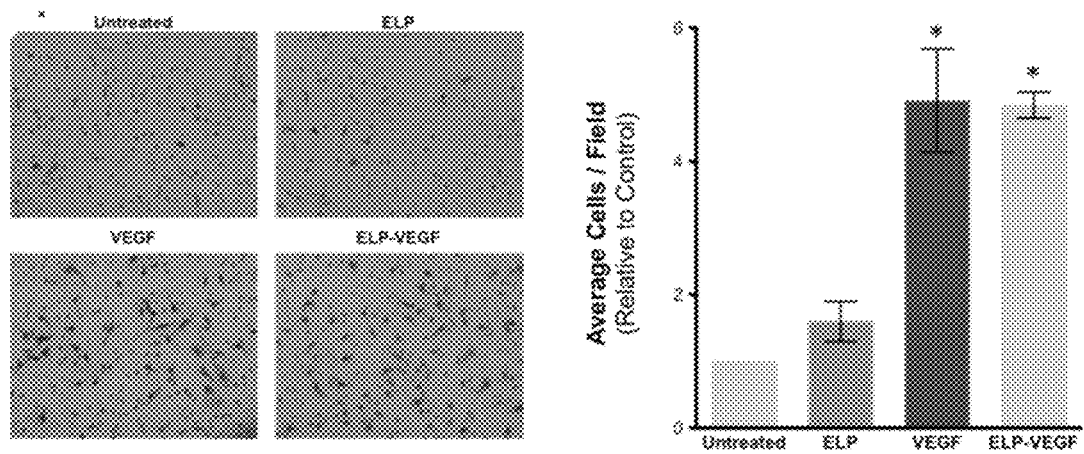
FIG. 8D
FIG. 8E

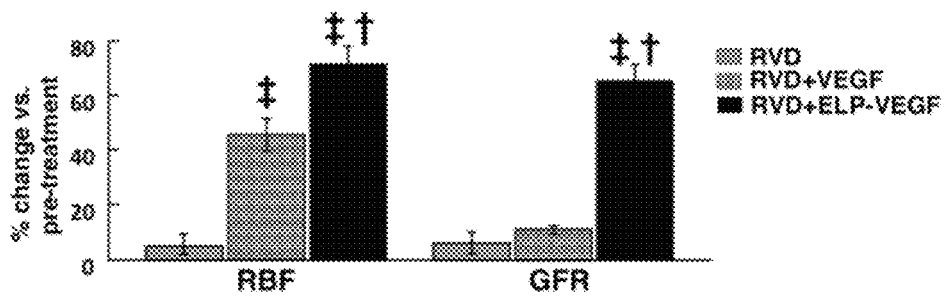
FIG. 10A
| B. Responses to Ach at 10 weeks | | Baseline | after Ach |
|---|---|---|---|
| RBF (mL/min) | ▦ | 269.7 +/-37.1 | 255.8+/- 67.4 |
| | ▨ | 281.5 +/-31.8 | 324.3+/- 44.2 ‡‡ |
| | ■ | 421.0 +/- 29.1 | 453.0 +/- 23.0 ‡‡ |
| GFR (mL/min) | ▦ | 42.3 +/- 5.4 | 43.4 +/- 7.8 |
| | ▨ | 46.5 +/- 6.7 | 53.1 +/- 5.3 |
| | ■ | 59.3 +/- 2.8 | 70.7 +/- 2.6 ‡‡ |
▦ RVD
▨ RVD+VEGF
■ RVD+ELP-VEGF
FIG. 10B
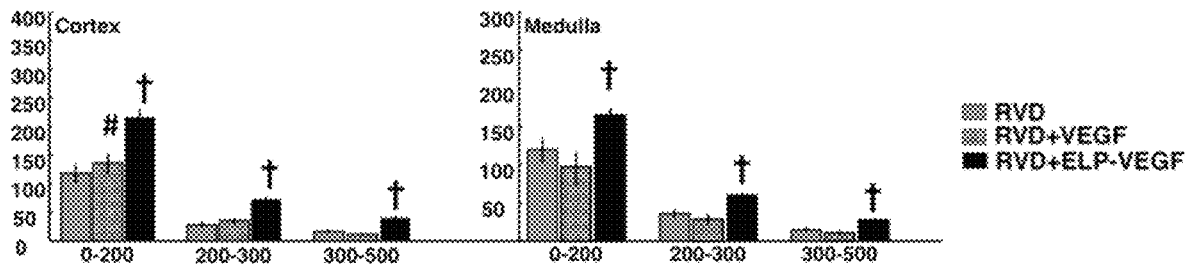
FIG. 10C

```
                       SEQUENCE LISTING

<160> NUMBER OF SEQ ID NOS: 13

<210> SEQ ID NO 1
<211> LENGTH: 5
<212> TYPE: PRT
<213> ORGANISM: Artificial
<220> FEATURE:
<223> OTHER INFORMATION: ELP Repeat
<220> FEATURE:
<221> NAME/KEY: MISC_FEATURE
<222> LOCATION: (4)..(4)
<223> OTHER INFORMATION: X can be any amino acid except proline

<400> SEQUENCE: 1

Val Pro Gly Xaa Gly
1               5

<210> SEQ ID NO 2
<211> LENGTH: 1600
<212> TYPE: PRT
<213> ORGANISM: Artificial
<220> FEATURE:
<223> OTHER INFORMATION: ELP
<220> FEATURE:
<221> NAME/KEY: MISC_FEATURE
<222> LOCATION: (1)..(1600)
<223> OTHER INFORMATION: The sequence is 20 repeating units of the
      sequence VPGVGVPGAGVPGGGVPGAGVPGGGVPGAGVPGGGVPGAGVPGGGVPGAGVPGGGVP
      GAGVPGGGVPGAGVPGGGVPGAG, i.e., n=20, however n can be an integer
      from 1 to 20

<400> SEQUENCE: 2

Val Pro Gly Val Gly Val Pro Gly Ala Gly Val Pro Gly Gly Val
1               5                   10                  15

Pro Gly Ala Gly Val Pro Gly Gly Gly Val Pro Gly Ala Gly Val Pro
                20                  25                  30

Gly Gly Gly Val Pro Gly Ala Gly Val Pro Gly Gly Gly Val Pro Gly
                35                  40                  45
```

-continued

```
Ala Gly Val Pro Gly Gly Val Pro Gly Ala Gly Val Pro Gly Gly
         50                  55                  60
Gly Val Pro Gly Ala Gly Val Pro Gly Gly Val Pro Gly Ala Gly
 65                  70                  75                  80
Val Pro Gly Val Gly Val Pro Gly Ala Gly Val Pro Gly Gly Val
                 85                  90                  95
Pro Gly Ala Gly Val Pro Gly Gly Val Pro Gly Ala Gly Val Pro
             100                 105                 110
Gly Gly Gly Val Pro Gly Ala Gly Val Pro Gly Gly Val Pro Gly
         115                 120                 125
Ala Gly Val Pro Gly Gly Val Pro Gly Ala Gly Val Pro Gly Gly
 130                 135                 140
Gly Val Pro Gly Ala Gly Val Pro Gly Gly Val Pro Gly Ala Gly
145                 150                 155                 160
Val Pro Gly Val Gly Val Pro Gly Ala Gly Val Pro Gly Gly Val
                165                 170                 175
Pro Gly Ala Gly Val Pro Gly Gly Val Pro Gly Ala Gly Val Pro
            180                 185                 190
Gly Gly Gly Val Pro Gly Ala Gly Val Pro Gly Gly Val Pro Gly
        195                 200                 205
Ala Gly Val Pro Gly Gly Val Pro Gly Ala Gly Val Pro Gly Gly
210                 215                 220
Gly Val Pro Gly Ala Gly Val Pro Gly Gly Val Pro Gly Ala Gly
225                 230                 235                 240
Val Pro Gly Val Gly Val Pro Gly Ala Gly Val Pro Gly Gly Val
                245                 250                 255
Pro Gly Ala Gly Val Pro Gly Gly Val Pro Gly Ala Gly Val Pro
            260                 265                 270
Gly Gly Gly Val Pro Gly Ala Gly Val Pro Gly Gly Val Pro Gly
        275                 280                 285
Ala Gly Val Pro Gly Gly Val Pro Gly Ala Gly Val Pro Gly Gly
290                 295                 300
Gly Val Pro Gly Ala Gly Val Pro Gly Gly Val Pro Gly Ala Gly
305                 310                 315                 320
Val Pro Gly Val Gly Val Pro Gly Ala Gly Val Pro Gly Gly Val
                325                 330                 335
Pro Gly Ala Gly Val Pro Gly Gly Val Pro Gly Ala Gly Val Pro
            340                 345                 350
Gly Gly Gly Val Pro Gly Ala Gly Val Pro Gly Gly Val Pro Gly
        355                 360                 365
Ala Gly Val Pro Gly Gly Val Pro Gly Ala Gly Val Pro Gly Gly
370                 375                 380
Gly Val Pro Gly Ala Gly Val Pro Gly Gly Val Pro Gly Ala Gly
385                 390                 395                 400
Val Pro Gly Val Gly Val Pro Gly Ala Gly Val Pro Gly Gly Val
                405                 410                 415
Pro Gly Ala Gly Val Pro Gly Gly Val Pro Gly Ala Gly Val Pro
            420                 425                 430
Gly Gly Gly Val Pro Gly Ala Gly Val Pro Gly Gly Val Pro Gly
        435                 440                 445
Ala Gly Val Pro Gly Gly Val Pro Gly Ala Gly Val Pro Gly Gly
450                 455                 460
Gly Val Pro Gly Ala Gly Val Pro Gly Gly Gly Val Pro Gly Ala Gly
```

-continued

```
            465                 470                 475                 480
Val Pro Gly Val Gly Val Pro Gly Ala Gly Val Pro Gly Gly Gly Val
                    485                 490                 495
Pro Gly Ala Gly Val Pro Gly Gly Gly Val Pro Gly Ala Gly Val Pro
                500                 505                 510
Gly Gly Gly Val Pro Gly Ala Gly Val Pro Gly Gly Gly Val Pro Gly
            515                 520                 525
Ala Gly Val Pro Gly Gly Gly Val Pro Gly Ala Gly Val Pro Gly Gly
        530                 535                 540
Gly Val Pro Gly Ala Gly Val Pro Gly Gly Gly Val Pro Gly Ala Gly
545                 550                 555                 560
Val Pro Gly Val Gly Val Pro Gly Ala Gly Val Pro Gly Gly Gly Val
                    565                 570                 575
Pro Gly Ala Gly Val Pro Gly Gly Gly Val Pro Gly Ala Gly Val Pro
                580                 585                 590
Gly Gly Gly Val Pro Gly Ala Gly Val Pro Gly Gly Gly Val Pro Gly
            595                 600                 605
Ala Gly Val Pro Gly Gly Gly Val Pro Gly Ala Gly Val Pro Gly Gly
        610                 615                 620
Gly Val Pro Gly Ala Gly Val Pro Gly Gly Gly Val Pro Gly Ala Gly
625                 630                 635                 640
Val Pro Gly Val Gly Val Pro Gly Ala Gly Val Pro Gly Gly Gly Val
                    645                 650                 655
Pro Gly Ala Gly Val Pro Gly Gly Gly Val Pro Gly Ala Gly Val Pro
                660                 665                 670
Gly Gly Gly Val Pro Gly Ala Gly Val Pro Gly Gly Gly Val Pro Gly
            675                 680                 685
Ala Gly Val Pro Gly Gly Gly Val Pro Gly Ala Gly Val Pro Gly Gly
        690                 695                 700
Gly Val Pro Gly Ala Gly Val Pro Gly Gly Gly Val Pro Gly Ala Gly
705                 710                 715                 720
Val Pro Gly Val Gly Val Pro Gly Ala Gly Val Pro Gly Gly Gly Val
                    725                 730                 735
Pro Gly Ala Gly Val Pro Gly Gly Gly Val Pro Gly Ala Gly Val Pro
                740                 745                 750
Gly Gly Gly Val Pro Gly Ala Gly Val Pro Gly Gly Gly Val Pro Gly
            755                 760                 765
Ala Gly Val Pro Gly Gly Gly Val Pro Gly Ala Gly Val Pro Gly Gly
        770                 775                 780
Gly Val Pro Gly Ala Gly Val Pro Gly Gly Gly Val Pro Gly Ala Gly
785                 790                 795                 800
Val Pro Gly Val Gly Val Pro Gly Ala Gly Val Pro Gly Gly Gly Val
                    805                 810                 815
Pro Gly Ala Gly Val Pro Gly Gly Gly Val Pro Gly Ala Gly Val Pro
                820                 825                 830
Gly Gly Gly Val Pro Gly Ala Gly Val Pro Gly Gly Gly Val Pro Gly
            835                 840                 845
Ala Gly Val Pro Gly Gly Gly Val Pro Gly Ala Gly Val Pro Gly Gly
        850                 855                 860
Gly Val Pro Gly Ala Gly Val Pro Gly Gly Gly Val Pro Gly Ala Gly
865                 870                 875                 880
Val Pro Gly Val Gly Val Pro Gly Ala Gly Val Pro Gly Gly Gly Val
                    885                 890                 895
```

-continued

```
Pro Gly Ala Gly Val Pro Gly Gly Val Pro Gly Ala Gly Val Pro
            900                 905                 910
Gly Gly Gly Val Pro Gly Ala Gly Val Pro Gly Gly Gly Val Pro Gly
            915                 920                 925
Ala Gly Val Pro Gly Gly Val Pro Gly Ala Gly Val Pro Gly Gly
            930                 935                 940
Gly Val Pro Gly Ala Gly Val Pro Gly Gly Val Pro Gly Ala Gly
945                 950                 955                 960
Val Pro Gly Val Gly Val Pro Gly Ala Gly Val Pro Gly Gly Val
                965                 970                 975
Pro Gly Ala Gly Val Pro Gly Gly Val Pro Gly Ala Gly Val Pro
            980                 985                 990
Gly Gly Gly Val Pro Gly Ala Gly Val Pro Gly Gly Gly Val Pro Gly
            995                 1000                1005
Ala Gly Val Pro Gly Gly Gly Val Pro Gly Ala Gly Val Pro Gly
            1010                1015                1020
Gly Gly Val Pro Gly Ala Gly Val Pro Gly Gly Gly Val Pro Gly
            1025                1030                1035
Ala Gly Val Pro Gly Val Gly Val Pro Gly Ala Gly Val Pro Gly
            1040                1045                1050
Gly Gly Val Pro Gly Ala Gly Val Pro Gly Gly Gly Val Pro Gly
            1055                1060                1065
Ala Gly Val Pro Gly Gly Gly Val Pro Gly Ala Gly Val Pro Gly
            1070                1075                1080
Gly Gly Val Pro Gly Ala Gly Val Pro Gly Gly Gly Val Pro Gly
            1085                1090                1095
Ala Gly Val Pro Gly Gly Gly Val Pro Gly Ala Gly Val Pro Gly
            1100                1105                1110
Gly Gly Val Pro Gly Ala Gly Val Pro Gly Val Gly Val Pro Gly
            1115                1120                1125
Ala Gly Val Pro Gly Gly Gly Val Pro Gly Ala Gly Val Pro Gly
            1130                1135                1140
Gly Gly Val Pro Gly Ala Gly Val Pro Gly Gly Gly Val Pro Gly
            1145                1150                1155
Ala Gly Val Pro Gly Gly Gly Val Pro Gly Ala Gly Val Pro Gly
            1160                1165                1170
Gly Gly Val Pro Gly Ala Gly Val Pro Gly Gly Gly Val Pro Gly
            1175                1180                1185
Ala Gly Val Pro Gly Gly Gly Val Pro Gly Ala Gly Val Pro Gly
            1190                1195                1200
Val Gly Val Pro Gly Ala Gly Val Pro Gly Gly Gly Val Pro Gly
            1205                1210                1215
Ala Gly Val Pro Gly Gly Gly Val Pro Gly Ala Gly Val Pro Gly
            1220                1225                1230
Gly Gly Val Pro Gly Ala Gly Val Pro Gly Gly Gly Val Pro Gly
            1235                1240                1245
Ala Gly Val Pro Gly Gly Gly Val Pro Gly Ala Gly Val Pro Gly
            1250                1255                1260
Gly Gly Val Pro Gly Ala Gly Val Pro Gly Gly Gly Val Pro Gly
            1265                1270                1275
Ala Gly Val Pro Gly Val Gly Val Pro Gly Ala Gly Val Pro Gly
            1280                1285                1290
```

```
Gly Gly  Val Pro Gly Ala Gly  Val Pro Gly Gly  Gly  Val Pro Gly
    1295             1300                1305

Ala Gly  Val Pro Gly Gly Gly  Val Pro Gly Ala  Gly  Val Pro Gly
    1310             1315                1320

Gly Gly  Val Pro Gly Ala Gly  Val Pro Gly Gly  Gly  Val Pro Gly
    1325             1330                1335

Ala Gly  Val Pro Gly Gly Gly  Val Pro Gly Ala  Gly  Val Pro Gly
    1340             1345                1350

Gly Gly  Val Pro Gly Ala Gly  Val Pro Gly Val  Gly  Val Pro Gly
    1355             1360                1365

Ala Gly  Val Pro Gly Gly Gly  Val Pro Gly Ala  Gly  Val Pro Gly
    1370             1375                1380

Gly Gly  Val Pro Gly Ala Gly  Val Pro Gly Gly  Gly  Val Pro Gly
    1385             1390                1395

Ala Gly  Val Pro Gly Gly Gly  Val Pro Gly Ala  Gly  Val Pro Gly
    1400             1405                1410

Gly Gly  Val Pro Gly Ala Gly  Val Pro Gly Gly  Gly  Val Pro Gly
    1415             1420                1425

Ala Gly  Val Pro Gly Gly Gly  Val Pro Gly Ala  Gly  Val Pro Gly
    1430             1435                1440

Val Gly  Val Pro Gly Ala Gly  Val Pro Gly Gly  Gly  Val Pro Gly
    1445             1450                1455

Ala Gly  Val Pro Gly Gly Gly  Val Pro Gly Ala  Gly  Val Pro Gly
    1460             1465                1470

Gly Gly  Val Pro Gly Ala Gly  Val Pro Gly Gly  Gly  Val Pro Gly
    1475             1480                1485

Ala Gly  Val Pro Gly Gly Gly  Val Pro Gly Ala  Gly  Val Pro Gly
    1490             1495                1500

Gly Gly  Val Pro Gly Ala Gly  Val Pro Gly Gly  Gly  Val Pro Gly
    1505             1510                1515

Ala Gly  Val Pro Gly Val Gly  Val Pro Gly Ala  Gly  Val Pro Gly
    1520             1525                1530

Gly Gly  Val Pro Gly Ala Gly  Val Pro Gly Gly  Gly  Val Pro Gly
    1535             1540                1545

Ala Gly  Val Pro Gly Gly Gly  Val Pro Gly Ala  Gly  Val Pro Gly
    1550             1555                1560

Gly Gly  Val Pro Gly Ala Gly  Val Pro Gly Gly  Gly  Val Pro Gly
    1565             1570                1575

Ala Gly  Val Pro Gly Gly Gly  Val Pro Gly Ala  Gly  Val Pro Gly
    1580             1585                1590

Gly Gly  Val Pro Gly Ala Gly
    1595             1600

<210> SEQ ID NO 3
<211> LENGTH: 1600
<212> TYPE: PRT
<213> ORGANISM: Artificial
<220> FEATURE:
<223> OTHER INFORMATION: ELP
<220> FEATURE:
<221> NAME/KEY: MISC_FEATURE
<222> LOCATION: (1)..(1600)
<223> OTHER INFORMATION: The sequence includes 320 repeating units of
      the amino acid sequence GVPGG, i.e., n=320; however, this unit can
      be repeated such that n is an integer from 5 to 320

<400> SEQUENCE: 3
```

```
Gly Val Pro Gly Gly Gly Val Pro Gly Gly Gly Val Pro Gly Gly Gly
1               5                   10                  15
Val Pro Gly Gly Gly Val Pro Gly Gly Gly Val Pro Gly Gly Gly Val
            20                  25                  30
Pro Gly Gly Gly Val Pro Gly Gly Gly Val Pro Gly Gly Gly Val Pro
        35                  40                  45
Gly Gly Gly Val Pro Gly Gly Gly Val Pro Gly Gly Gly Val Pro Gly
50                  55                  60
Gly Gly Val Pro Gly Gly Gly Val Pro Gly Gly Gly Val Pro Gly Gly
65                  70                  75                  80
Gly Val Pro Gly Gly Gly Val Pro Gly Gly Gly Val Pro Gly Gly Gly
            85                  90                  95
Val Pro Gly Gly Gly Val Pro Gly Gly Gly Val Pro Gly Gly Gly Val
            100                 105                 110
Pro Gly Gly Gly Val Pro Gly Gly Gly Val Pro Gly Gly Gly Val Pro
        115                 120                 125
Gly Gly Gly Val Pro Gly Gly Gly Val Pro Gly Gly Gly Val Pro Gly
    130                 135                 140
Gly Gly Val Pro Gly Gly Gly Val Pro Gly Gly Gly Val Pro Gly Gly
145                 150                 155                 160
Gly Val Pro Gly Gly Gly Val Pro Gly Gly Gly Val Pro Gly Gly Gly
            165                 170                 175
Val Pro Gly Gly Gly Val Pro Gly Gly Gly Val Pro Gly Gly Gly Val
            180                 185                 190
Pro Gly Gly Gly Val Pro Gly Gly Gly Val Pro Gly Gly Gly Val Pro
        195                 200                 205
Gly Gly Gly Val Pro Gly Gly Gly Val Pro Gly Gly Gly Val Pro Gly
    210                 215                 220
Gly Gly Val Pro Gly Gly Gly Val Pro Gly Gly Gly Val Pro Gly Gly
225                 230                 235                 240
Gly Val Pro Gly Gly Gly Val Pro Gly Gly Gly Val Pro Gly Gly Gly
            245                 250                 255
Val Pro Gly Gly Gly Val Pro Gly Gly Gly Val Pro Gly Gly Gly Val
            260                 265                 270
Pro Gly Gly Gly Val Pro Gly Gly Gly Val Pro Gly Gly Gly Val Pro
        275                 280                 285
Gly Gly Gly Val Pro Gly Gly Gly Val Pro Gly Gly Gly Val Pro Gly
    290                 295                 300
Gly Gly Val Pro Gly Gly Gly Val Pro Gly Gly Gly Val Pro Gly Gly
305                 310                 315                 320
Gly Val Pro Gly Gly Gly Val Pro Gly Gly Gly Val Pro Gly Gly Gly
            325                 330                 335
Val Pro Gly Gly Gly Val Pro Gly Gly Gly Val Pro Gly Gly Gly Val
            340                 345                 350
Pro Gly Gly Gly Val Pro Gly Gly Gly Val Pro Gly Gly Gly Val Pro
        355                 360                 365
Gly Gly Gly Val Pro Gly Gly Gly Val Pro Gly Gly Gly Val Pro Gly
    370                 375                 380
Gly Gly Val Pro Gly Gly Gly Val Pro Gly Gly Gly Val Pro Gly Gly
385                 390                 395                 400
Gly Val Pro Gly Gly Gly Val Pro Gly Gly Gly Val Pro Gly Gly Gly
            405                 410                 415
Val Pro Gly Gly Gly Val Pro Gly Gly Gly Val Pro Gly Gly Gly Val
```

```
            420                 425                 430
Pro Gly Gly Gly Val Pro Gly Gly Gly Val Pro Gly Gly Gly Val Pro
        435                 440                 445
Gly Gly Gly Val Pro Gly Gly Gly Val Pro Gly Gly Gly Val Pro Gly
    450                 455                 460
Gly Gly Val Pro Gly Gly Gly Val Pro Gly Gly Gly Val Pro Gly Gly
465                 470                 475                 480
Gly Val Pro Gly Gly Gly Val Pro Gly Gly Gly Val Pro Gly Gly Gly
                485                 490                 495
Val Pro Gly Gly Gly Val Pro Gly Gly Gly Val Pro Gly Gly Gly Val
            500                 505                 510
Pro Gly Gly Gly Val Pro Gly Gly Gly Val Pro Gly Gly Gly Val Pro
        515                 520                 525
Gly Gly Gly Val Pro Gly Gly Gly Val Pro Gly Gly Gly Val Pro Gly
    530                 535                 540
Gly Gly Val Pro Gly Gly Gly Val Pro Gly Gly Gly Val Pro Gly Gly
545                 550                 555                 560
Gly Val Pro Gly Gly Gly Val Pro Gly Gly Gly Val Pro Gly Gly Gly
                565                 570                 575
Val Pro Gly Gly Gly Val Pro Gly Gly Gly Val Pro Gly Gly Gly Val
            580                 585                 590
Pro Gly Gly Gly Val Pro Gly Gly Gly Val Pro Gly Gly Gly Val Pro
        595                 600                 605
Gly Gly Gly Val Pro Gly Gly Gly Val Pro Gly Gly Gly Val Pro Gly
    610                 615                 620
Gly Gly Val Pro Gly Gly Gly Val Pro Gly Gly Gly Val Pro Gly Gly
625                 630                 635                 640
Gly Val Pro Gly Gly Gly Val Pro Gly Gly Gly Val Pro Gly Gly Gly
                645                 650                 655
Val Pro Gly Gly Gly Val Pro Gly Gly Gly Val Pro Gly Gly Gly Val
            660                 665                 670
Pro Gly Gly Gly Val Pro Gly Gly Gly Val Pro Gly Gly Gly Val Pro
        675                 680                 685
Gly Gly Gly Val Pro Gly Gly Gly Val Pro Gly Gly Gly Val Pro Gly
    690                 695                 700
Gly Gly Val Pro Gly Gly Gly Val Pro Gly Gly Gly Val Pro Gly Gly
705                 710                 715                 720
Gly Val Pro Gly Gly Gly Val Pro Gly Gly Gly Val Pro Gly Gly Gly
                725                 730                 735
Val Pro Gly Gly Gly Val Pro Gly Gly Gly Val Pro Gly Gly Gly Val
            740                 745                 750
Pro Gly Gly Gly Val Pro Gly Gly Gly Val Pro Gly Gly Gly Val Pro
        755                 760                 765
Gly Gly Gly Val Pro Gly Gly Gly Val Pro Gly Gly Gly Val Pro Gly
    770                 775                 780
Gly Gly Val Pro Gly Gly Gly Val Pro Gly Gly Gly Val Pro Gly Gly
785                 790                 795                 800
Gly Val Pro Gly Gly Gly Val Pro Gly Gly Gly Val Pro Gly Gly Gly
                805                 810                 815
Val Pro Gly Gly Gly Val Pro Gly Gly Gly Val Pro Gly Gly Gly Val
            820                 825                 830
Pro Gly Gly Gly Val Pro Gly Gly Gly Val Pro Gly Gly Gly Val Pro
        835                 840                 845
```

Gly Gly Gly Val Pro Gly Gly Val Pro Gly Gly Val Pro Gly
850                 855                 860

Gly Gly Val Pro Gly Gly Val Pro Gly Gly Val Pro Gly Gly
865                 870                 875                 880

Gly Val Pro Gly Gly Val Pro Gly Gly Val Pro Gly Gly Gly
                885                 890                 895

Val Pro Gly Gly Gly Val Pro Gly Gly Gly Val Pro Gly Gly Val
            900                 905                 910

Pro Gly Gly Gly Val Pro Gly Gly Gly Val Pro Gly Gly Gly Val Pro
        915                 920                 925

Gly Gly Gly Val Pro Gly Gly Gly Val Pro Gly Gly Gly Val Pro Gly
930                 935                 940

Gly Gly Val Pro Gly Gly Gly Val Pro Gly Gly Gly Val Pro Gly Gly
945                 950                 955                 960

Gly Val Pro Gly Gly Gly Val Pro Gly Gly Gly Val Pro Gly Gly Gly
                965                 970                 975

Val Pro Gly Gly Gly Val Pro Gly Gly Gly Val Pro Gly Gly Gly Val
            980                 985                 990

Pro Gly Gly Gly Val Pro Gly Gly Gly Val Pro Gly Gly Gly Val Pro
        995                 1000                1005

Gly Gly Gly Val Pro Gly Gly Gly Val Pro Gly Gly Gly Val Pro
1010                1015                1020

Gly Gly Gly Val Pro Gly Gly Gly Val Pro Gly Gly Gly Val Pro
1025                1030                1035

Gly Gly Gly Val Pro Gly Gly Gly Val Pro Gly Gly Gly Val Pro
1040                1045                1050

Gly Gly Gly Val Pro Gly Gly Gly Val Pro Gly Gly Gly Val Pro
1055                1060                1065

Gly Gly Gly Val Pro Gly Gly Gly Val Pro Gly Gly Gly Val Pro
1070                1075                1080

Gly Gly Gly Val Pro Gly Gly Gly Val Pro Gly Gly Gly Val Pro
1085                1090                1095

Gly Gly Gly Val Pro Gly Gly Gly Val Pro Gly Gly Gly Val Pro
1100                1105                1110

Gly Gly Gly Val Pro Gly Gly Gly Val Pro Gly Gly Gly Val Pro
1115                1120                1125

Gly Gly Gly Val Pro Gly Gly Gly Val Pro Gly Gly Gly Val Pro
1130                1135                1140

Gly Gly Gly Val Pro Gly Gly Gly Val Pro Gly Gly Gly Val Pro
1145                1150                1155

Gly Gly Gly Val Pro Gly Gly Gly Val Pro Gly Gly Gly Val Pro
1160                1165                1170

Gly Gly Gly Val Pro Gly Gly Gly Val Pro Gly Gly Gly Val Pro
1175                1180                1185

Gly Gly Gly Val Pro Gly Gly Gly Val Pro Gly Gly Gly Val Pro
1190                1195                1200

Gly Gly Gly Val Pro Gly Gly Gly Val Pro Gly Gly Gly Val Pro
1205                1210                1215

Gly Gly Gly Val Pro Gly Gly Gly Val Pro Gly Gly Gly Val Pro
1220                1225                1230

Gly Gly Gly Val Pro Gly Gly Gly Val Pro Gly Gly Gly Val Pro
1235                1240                1245

Gly Gly Gly Val Pro Gly Gly Gly Val Pro Gly Gly Gly Val Pro
1250                1255                1260

Gly Gly Gly Val Pro Gly Gly Gly Val Pro Gly Gly Gly Val Pro
1265                1270                1275

Gly Gly Gly Val Pro Gly Gly Gly Val Pro Gly Gly Gly Val Pro
1280                1285                1290

Gly Gly Gly Val Pro Gly Gly Gly Val Pro Gly Gly Gly Val Pro
1295                1300                1305

Gly Gly Gly Val Pro Gly Gly Gly Val Pro Gly Gly Gly Val Pro
1310                1315                1320

Gly Gly Gly Val Pro Gly Gly Gly Val Pro Gly Gly Gly Val Pro
1325                1330                1335

Gly Gly Gly Val Pro Gly Gly Gly Val Pro Gly Gly Gly Val Pro
1340                1345                1350

Gly Gly Gly Val Pro Gly Gly Gly Val Pro Gly Gly Gly Val Pro
1355                1360                1365

Gly Gly Gly Val Pro Gly Gly Gly Val Pro Gly Gly Gly Val Pro
1370                1375                1380

Gly Gly Gly Val Pro Gly Gly Gly Val Pro Gly Gly Gly Val Pro
1385                1390                1395

Gly Gly Gly Val Pro Gly Gly Gly Val Pro Gly Gly Gly Val Pro
1400                1405                1410

Gly Gly Gly Val Pro Gly Gly Gly Val Pro Gly Gly Gly Val Pro
1415                1420                1425

Gly Gly Gly Val Pro Gly Gly Gly Val Pro Gly Gly Gly Val Pro
1430                1435                1440

Gly Gly Gly Val Pro Gly Gly Gly Val Pro Gly Gly Gly Val Pro
1445                1450                1455

Gly Gly Gly Val Pro Gly Gly Gly Val Pro Gly Gly Gly Val Pro
1460                1465                1470

Gly Gly Gly Val Pro Gly Gly Gly Val Pro Gly Gly Gly Val Pro
1475                1480                1485

Gly Gly Gly Val Pro Gly Gly Gly Val Pro Gly Gly Gly Val Pro
1490                1495                1500

Gly Gly Gly Val Pro Gly Gly Gly Val Pro Gly Gly Gly Val Pro
1505                1510                1515

Gly Gly Gly Val Pro Gly Gly Gly Val Pro Gly Gly Gly Val Pro
1520                1525                1530

Gly Gly Gly Val Pro Gly Gly Gly Val Pro Gly Gly Gly Val Pro
1535                1540                1545

Gly Gly Gly Val Pro Gly Gly Gly Val Pro Gly Gly Gly Val Pro
1550                1555                1560

Gly Gly Gly Val Pro Gly Gly Gly Val Pro Gly Gly Gly Val Pro
1565                1570                1575

Gly Gly Gly Val Pro Gly Gly Gly Val Pro Gly Gly Gly Val Pro
1580                1585                1590

Gly Gly Gly Val Pro Gly Gly
1595                1600

<210> SEQ ID NO 4
<211> LENGTH: 1600
<212> TYPE: PRT
<213> ORGANISM: Artificial
<220> FEATURE:
<223> OTHER INFORMATION: ELP
<220> FEATURE:
<221> NAME/KEY: MISC_FEATURE
<222> LOCATION: (1)..(1600)
<223> OTHER INFORMATION: The sequence includes 40 repeating units of the
      amino acid sequence VPGVGVPGAGVPGGGVPGAGVPGGGVPGAGVPGGGVPGAG,
      i.e., n=40; however, this unit can be repeated such that n is an
      integer from 1 to 40

<400> SEQUENCE: 4

```
Val Pro Gly Val Gly Val Pro Gly Ala Gly Val Pro Gly Gly Gly Val
1               5                   10                  15

Pro Gly Ala Gly Val Pro Gly Gly Gly Val Pro Gly Ala Gly Val Pro
            20                  25                  30

Gly Gly Gly Val Pro Gly Ala Gly Val Pro Gly Val Gly Val Pro Gly
        35                  40                  45

Ala Gly Val Pro Gly Gly Gly Val Pro Gly Ala Gly Val Pro Gly Gly
    50                  55                  60

Gly Val Pro Gly Ala Gly Val Pro Gly Gly Gly Val Pro Gly Ala Gly
65                  70                  75                  80

Val Pro Gly Val Gly Val Pro Gly Ala Gly Val Pro Gly Gly Gly Val
                85                  90                  95

Pro Gly Ala Gly Val Pro Gly Gly Gly Val Pro Gly Ala Gly Val Pro
            100                 105                 110

Gly Gly Gly Val Pro Gly Ala Gly Val Pro Gly Val Gly Val Pro Gly
        115                 120                 125

Ala Gly Val Pro Gly Gly Gly Val Pro Gly Ala Gly Val Pro Gly Gly
    130                 135                 140

Gly Val Pro Gly Ala Gly Val Pro Gly Gly Gly Val Pro Gly Ala Gly
145                 150                 155                 160

Val Pro Gly Val Gly Val Pro Gly Ala Gly Val Pro Gly Gly Gly Val
                165                 170                 175

Pro Gly Ala Gly Val Pro Gly Gly Gly Val Pro Gly Ala Gly Val Pro
            180                 185                 190

Gly Gly Gly Val Pro Gly Ala Gly Val Pro Gly Val Gly Val Pro Gly
        195                 200                 205

Ala Gly Val Pro Gly Gly Gly Val Pro Gly Ala Gly Val Pro Gly Gly
    210                 215                 220

Gly Val Pro Gly Ala Gly Val Pro Gly Gly Gly Val Pro Gly Ala Gly
225                 230                 235                 240

Val Pro Gly Val Gly Val Pro Gly Ala Gly Val Pro Gly Gly Gly Val
                245                 250                 255

Pro Gly Ala Gly Val Pro Gly Gly Gly Val Pro Gly Ala Gly Val Pro
            260                 265                 270

Gly Gly Gly Val Pro Gly Ala Gly Val Pro Gly Val Gly Val Pro Gly
        275                 280                 285

Ala Gly Val Pro Gly Gly Gly Val Pro Gly Ala Gly Val Pro Gly Gly
    290                 295                 300

Gly Val Pro Gly Ala Gly Val Pro Gly Gly Gly Val Pro Gly Ala Gly
305                 310                 315                 320

Val Pro Gly Val Gly Val Pro Gly Ala Gly Val Pro Gly Gly Gly Val
                325                 330                 335

Pro Gly Ala Gly Val Pro Gly Gly Gly Val Pro Gly Ala Gly Val Pro
            340                 345                 350

Gly Gly Gly Val Pro Gly Ala Gly Val Pro Gly Val Gly Val Pro Gly
        355                 360                 365
```

```
Ala Gly Val Pro Gly Gly Val Pro Gly Ala Gly Val Pro Gly Gly
    370                 375                 380

Gly Val Pro Gly Ala Gly Val Pro Gly Gly Gly Val Pro Gly Ala Gly
385                 390                 395                 400

Val Pro Gly Val Gly Val Pro Gly Ala Gly Val Pro Gly Gly Gly Val
                405                 410                 415

Pro Gly Ala Gly Val Pro Gly Gly Gly Val Pro Gly Ala Gly Val Pro
            420                 425                 430

Gly Gly Gly Val Pro Gly Ala Gly Val Pro Gly Val Gly Val Pro Gly
        435                 440                 445

Ala Gly Val Pro Gly Gly Val Pro Gly Ala Gly Val Pro Gly Gly
    450                 455                 460

Gly Val Pro Gly Ala Gly Val Pro Gly Gly Gly Val Pro Gly Ala Gly
465                 470                 475                 480

Val Pro Gly Val Gly Val Pro Gly Ala Gly Val Pro Gly Gly Gly Val
                485                 490                 495

Pro Gly Ala Gly Val Pro Gly Gly Gly Val Pro Gly Ala Gly Val Pro
            500                 505                 510

Gly Gly Gly Val Pro Gly Ala Gly Val Pro Gly Val Gly Val Pro Gly
        515                 520                 525

Ala Gly Val Pro Gly Gly Gly Val Pro Gly Ala Gly Val Pro Gly Gly
    530                 535                 540

Gly Val Pro Gly Ala Gly Val Pro Gly Gly Gly Val Pro Gly Ala Gly
545                 550                 555                 560

Val Pro Gly Val Gly Val Pro Gly Ala Gly Val Pro Gly Gly Gly Val
                565                 570                 575

Pro Gly Ala Gly Val Pro Gly Gly Gly Val Pro Gly Ala Gly Val Pro
            580                 585                 590

Gly Gly Gly Val Pro Gly Ala Gly Val Pro Gly Val Gly Val Pro Gly
        595                 600                 605

Ala Gly Val Pro Gly Gly Gly Val Pro Gly Ala Gly Val Pro Gly Gly
    610                 615                 620

Gly Val Pro Gly Ala Gly Val Pro Gly Gly Gly Val Pro Gly Ala Gly
625                 630                 635                 640

Val Pro Gly Val Gly Val Pro Gly Ala Gly Val Pro Gly Gly Gly Val
                645                 650                 655

Pro Gly Ala Gly Val Pro Gly Gly Gly Val Pro Gly Ala Gly Val Pro
            660                 665                 670

Gly Gly Gly Val Pro Gly Ala Gly Val Pro Gly Val Gly Val Pro Gly
        675                 680                 685

Ala Gly Val Pro Gly Gly Gly Val Pro Gly Ala Gly Val Pro Gly Gly
    690                 695                 700

Gly Val Pro Gly Ala Gly Val Pro Gly Gly Gly Val Pro Gly Ala Gly
705                 710                 715                 720

Val Pro Gly Val Gly Val Pro Gly Ala Gly Val Pro Gly Gly Gly Val
                725                 730                 735

Pro Gly Ala Gly Val Pro Gly Gly Gly Val Pro Gly Ala Gly Val Pro
            740                 745                 750

Gly Gly Gly Val Pro Gly Ala Gly Val Pro Gly Val Gly Val Pro Gly
        755                 760                 765

Ala Gly Val Pro Gly Gly Gly Val Pro Gly Ala Gly Val Pro Gly Gly
    770                 775                 780

Gly Val Pro Gly Ala Gly Val Pro Gly Gly Gly Val Pro Gly Ala Gly
```

-continued

```
            785                 790                 795                 800
Val Pro Gly Val Gly Val Pro Gly Ala Gly Val Pro Gly Gly Val
                805                 810                 815
Pro Gly Ala Gly Val Pro Gly Gly Gly Val Pro Gly Ala Gly Val Pro
                820                 825                 830
Gly Gly Gly Val Pro Gly Ala Gly Val Pro Gly Val Gly Val Pro Gly
                835                 840                 845
Ala Gly Val Pro Gly Gly Gly Val Pro Gly Ala Gly Val Pro Gly Gly
                850                 855                 860
Gly Val Pro Gly Ala Gly Val Pro Gly Gly Gly Val Pro Gly Ala Gly
865                 870                 875                 880
Val Pro Gly Val Gly Val Pro Gly Ala Gly Val Pro Gly Gly Gly Val
                885                 890                 895
Pro Gly Ala Gly Val Pro Gly Gly Gly Val Pro Gly Ala Gly Val Pro
                900                 905                 910
Gly Gly Gly Val Pro Gly Ala Gly Val Pro Gly Val Gly Val Pro Gly
                915                 920                 925
Ala Gly Val Pro Gly Gly Gly Val Pro Gly Ala Gly Val Pro Gly Gly
                930                 935                 940
Gly Val Pro Gly Ala Gly Val Pro Gly Gly Gly Val Pro Gly Ala Gly
945                 950                 955                 960
Val Pro Gly Val Gly Val Pro Gly Ala Gly Val Pro Gly Gly Gly Val
                965                 970                 975
Pro Gly Ala Gly Val Pro Gly Gly Gly Val Pro Gly Ala Gly Val Pro
                980                 985                 990
Gly Gly Gly Val Pro Gly Ala Gly  Val Pro Gly Val Gly  Val Pro Gly
                995                      1000                      1005
Ala Gly  Val Pro Gly Gly Gly  Val Pro Gly Ala Gly  Val Pro Gly
    1010                      1015                      1020
Gly Gly  Val Pro Gly Ala Gly  Val Pro Gly Gly Gly  Val Pro Gly
    1025                      1030                      1035
Ala Gly  Val Pro Gly Val Gly  Val Pro Gly Ala Gly  Val Pro Gly
    1040                      1045                      1050
Gly Gly  Val Pro Gly Ala Gly  Val Pro Gly Gly Gly  Val Pro Gly
    1055                      1060                      1065
Ala Gly  Val Pro Gly Gly Gly  Val Pro Gly Ala Gly  Val Pro Gly
    1070                      1075                      1080
Val Gly  Val Pro Gly Ala Gly  Val Pro Gly Gly Gly  Val Pro Gly
    1085                      1090                      1095
Ala Gly  Val Pro Gly Gly Gly  Val Pro Gly Ala Gly  Val Pro Gly
    1100                      1105                      1110
Gly Gly  Val Pro Gly Ala Gly  Val Pro Gly Val Gly  Val Pro Gly
    1115                      1120                      1125
Ala Gly  Val Pro Gly Gly Gly  Val Pro Gly Ala Gly  Val Pro Gly
    1130                      1135                      1140
Gly Gly  Val Pro Gly Ala Gly  Val Pro Gly Gly Gly  Val Pro Gly
    1145                      1150                      1155
Ala Gly  Val Pro Gly Val Gly  Val Pro Gly Ala Gly  Val Pro Gly
    1160                      1165                      1170
Gly Gly  Val Pro Gly Ala Gly  Val Pro Gly Gly Gly  Val Pro Gly
    1175                      1180                      1185
Ala Gly  Val Pro Gly Gly Gly  Val Pro Gly Ala Gly  Val Pro Gly
    1190                      1195                      1200
```

```
Val Gly Val Pro Gly Ala Gly Val Pro Gly Gly Gly Val Pro Gly
    1205                1210                1215

Ala Gly Val Pro Gly Gly Gly Val Pro Gly Ala Gly Val Pro Gly
    1220                1225                1230

Gly Gly Val Pro Gly Ala Gly Val Pro Gly Val Gly Val Pro Gly
    1235                1240                1245

Ala Gly Val Pro Gly Gly Gly Val Pro Gly Ala Gly Val Pro Gly
    1250                1255                1260

Gly Gly Val Pro Gly Ala Gly Val Pro Gly Gly Gly Val Pro Gly
    1265                1270                1275

Ala Gly Val Pro Gly Val Gly Val Pro Gly Ala Gly Val Pro Gly
    1280                1285                1290

Gly Gly Val Pro Gly Ala Gly Val Pro Gly Gly Gly Val Pro Gly
    1295                1300                1305

Ala Gly Val Pro Gly Gly Gly Val Pro Gly Ala Gly Val Pro Gly
    1310                1315                1320

Val Gly Val Pro Gly Ala Gly Val Pro Gly Gly Gly Val Pro Gly
    1325                1330                1335

Ala Gly Val Pro Gly Gly Gly Val Pro Gly Ala Gly Val Pro Gly
    1340                1345                1350

Gly Gly Val Pro Gly Ala Gly Val Pro Gly Val Gly Val Pro Gly
    1355                1360                1365

Ala Gly Val Pro Gly Gly Gly Val Pro Gly Ala Gly Val Pro Gly
    1370                1375                1380

Gly Gly Val Pro Gly Ala Gly Val Pro Gly Gly Gly Val Pro Gly
    1385                1390                1395

Ala Gly Val Pro Gly Val Gly Val Pro Gly Ala Gly Val Pro Gly
    1400                1405                1410

Gly Gly Val Pro Gly Ala Gly Val Pro Gly Gly Gly Val Pro Gly
    1415                1420                1425

Ala Gly Val Pro Gly Gly Gly Val Pro Gly Ala Gly Val Pro Gly
    1430                1435                1440

Val Gly Val Pro Gly Ala Gly Val Pro Gly Gly Gly Val Pro Gly
    1445                1450                1455

Ala Gly Val Pro Gly Gly Gly Val Pro Gly Ala Gly Val Pro Gly
    1460                1465                1470

Gly Gly Val Pro Gly Ala Gly Val Pro Gly Val Gly Val Pro Gly
    1475                1480                1485

Ala Gly Val Pro Gly Gly Gly Val Pro Gly Ala Gly Val Pro Gly
    1490                1495                1500

Gly Gly Val Pro Gly Ala Gly Val Pro Gly Gly Gly Val Pro Gly
    1505                1510                1515

Ala Gly Val Pro Gly Val Gly Val Pro Gly Ala Gly Val Pro Gly
    1520                1525                1530

Gly Gly Val Pro Gly Ala Gly Val Pro Gly Gly Gly Val Pro Gly
    1535                1540                1545

Ala Gly Val Pro Gly Gly Gly Val Pro Gly Ala Gly Val Pro Gly
    1550                1555                1560

Val Gly Val Pro Gly Ala Gly Val Pro Gly Gly Gly Val Pro Gly
    1565                1570                1575

Ala Gly Val Pro Gly Gly Gly Val Pro Gly Ala Gly Val Pro Gly
    1580                1585                1590
```

```
Gly Gly  Val Pro Gly Ala Gly
    1595             1600
```

<210> SEQ ID NO 5
<211> LENGTH: 7
<212> TYPE: PRT
<213> ORGANISM: Artificial
<220> FEATURE:
<223> OTHER INFORMATION: Kidney Targeting Peptide

<400> SEQUENCE: 5

```
Cys Leu Pro Val Ala Ser Cys
1               5
```

<210> SEQ ID NO 6
<211> LENGTH: 7
<212> TYPE: PRT
<213> ORGANISM: Artificial
<220> FEATURE:
<223> OTHER INFORMATION: Kidney Targeting Peptide

<400> SEQUENCE: 6

```
Cys Gly Ala Arg Glu Met Cys
1               5
```

<210> SEQ ID NO 7
<211> LENGTH: 11
<212> TYPE: PRT
<213> ORGANISM: Artificial
<220> FEATURE:
<223> OTHER INFORMATION: Tat Peptide

<400> SEQUENCE: 7

```
Tyr Gly Arg Lys Lys Arg Arg Gln Arg Arg Arg
1               5                   10
```

<210> SEQ ID NO 8
<211> LENGTH: 18
<212> TYPE: PRT
<213> ORGANISM: Artificial
<220> FEATURE:
<223> OTHER INFORMATION: SynB1 Peptide

<400> SEQUENCE: 8

```
Arg Gly Gly Arg Leu Ser Tyr Ser Arg Arg Arg Phe Ser Thr Ser Thr
1               5                   10                  15

Gly Arg
```

<210> SEQ ID NO 9
<211> LENGTH: 90
<212> TYPE: PRT
<213> ORGANISM: Artificial
<220> FEATURE:
<223> OTHER INFORMATION: Drug Binding Domain
<220> FEATURE:
<221> NAME/KEY: MISC_FEATURE
<222> LOCATION: (1)..(90)
<223> OTHER INFORMATION: The sequence includes 10 repeating units of the
      amino acid sequence GGCGGCGGC, i.e., n=10; however this unit can
      be repeated such that n is an integer from 1 to 10.

<400> SEQUENCE: 9

```
Gly Gly Cys Gly Gly Cys Gly Gly Cys Gly Gly Cys Gly Gly Cys Gly
1               5                   10                  15

Gly Cys Gly Gly Cys Gly Gly Cys Gly Gly Cys Gly Gly Cys Gly Gly
                20                  25                  30
```

```
Cys Gly Gly Cys Gly Gly Cys Gly Cys Gly Gly Cys
        35                  40                  45

Gly Gly Cys Gly Gly Cys Gly Cys Gly Gly Cys Gly
50                  55                  60

Gly Cys Gly Gly Cys Gly Cys Gly Gly Cys Gly Gly
65                  70                  75                  80

Cys Gly Gly Cys Gly Gly Cys Gly Gly Cys
                85                  90

<210> SEQ ID NO 10
<211> LENGTH: 60
<212> TYPE: PRT
<213> ORGANISM: Artificial
<220> FEATURE:
<223> OTHER INFORMATION: Drug Binding Domain
<220> FEATURE:
<221> NAME/KEY: MISC_FEATURE
<222> LOCATION: (1)..(60)
<223> OTHER INFORMATION: The sequence includes 10 repeating units of the
      amino acid sequence GCGCGC, i.e., n=10; however this unit can be
      repeated such that n is an integer from 1 to 10.

<400> SEQUENCE: 10

Gly Cys Gly Cys Gly Cys Gly Cys Gly Cys Gly Cys Gly Cys Gly Cys
1               5                   10                  15

Gly Cys Gly Cys Gly Cys Gly Cys Gly Cys Gly Cys Gly Cys Gly Cys
            20                  25                  30

Gly Cys Gly Cys Gly Cys Gly Cys Gly Cys Gly Cys Gly Cys Gly Cys
        35                  40                  45

Gly Cys Gly Cys Gly Cys Gly Cys Gly Cys Gly Cys
    50                  55                  60

<210> SEQ ID NO 11
<211> LENGTH: 90
<212> TYPE: PRT
<213> ORGANISM: Artificial
<220> FEATURE:
<223> OTHER INFORMATION: Drug Binding Domain
<220> FEATURE:
<221> NAME/KEY: MISC_FEATURE
<222> LOCATION: (1)..(90)
<223> OTHER INFORMATION: The sequence includes 10 repeating units of the
      amino acid sequence GGKGGKGGK, i.e., n=10; however, this unit can
      be repeated such that n is an integer from 1 to 10.

<400> SEQUENCE: 11

Gly Gly Lys Gly Gly Lys Gly Gly Lys Gly Gly Lys Gly Gly Lys Gly
1               5                   10                  15

Gly Lys Gly Gly Lys Gly Gly Lys Gly Gly Lys Gly Gly Lys Gly Gly
            20                  25                  30

Lys Gly Gly Lys Gly Gly Lys Gly Gly Lys Gly Gly Lys Gly Gly Lys
        35                  40                  45

Gly Gly Lys Gly Gly Lys Gly Gly Lys Gly Gly Lys Gly Gly Lys Gly
    50                  55                  60

Gly Lys Gly Gly Lys Gly Gly Lys Gly Gly Lys Gly Gly Lys Gly Gly
65                  70                  75                  80

Lys Gly Gly Lys Gly Gly Lys Gly Gly Lys
                85                  90

<210> SEQ ID NO 12
<211> LENGTH: 60
<212> TYPE: PRT
<213> ORGANISM: Artificial
```

```
<220> FEATURE:
<223> OTHER INFORMATION: Drug Binding Domain
<220> FEATURE:
<221> NAME/KEY: MISC_FEATURE
<222> LOCATION: (1)..(60)
<223> OTHER INFORMATION: The sequence includes 10 repeating units of the
      amino acid sequence GKGKGK, i.e., n=10; however, this unit can be
      repeated such that n is an integer from 1 to 10.

<400> SEQUENCE: 12

Gly Lys Gly Lys Gly Lys Gly Lys Gly Lys Gly Lys Gly Lys Gly Lys
1               5                   10                  15

Gly Lys Gly Lys Gly Lys Gly Lys Gly Lys Gly Lys Gly Lys Gly Lys
            20                  25                  30

Gly Lys Gly Lys Gly Lys Gly Lys Gly Lys Gly Lys Gly Lys Gly Lys
        35                  40                  45

Gly Lys Gly Lys Gly Lys Gly Lys Gly Lys Gly Lys
    50                  55                  60

<210> SEQ ID NO 13
<211> LENGTH: 3365
<212> TYPE: PRT
<213> ORGANISM: Artificial
<220> FEATURE:
<223> OTHER INFORMATION: ELP
<220> FEATURE:
<221> NAME/KEY: REPEAT
<222> LOCATION: (6)..(3360)
<223> OTHER INFORMATION: Includes 671 repeats of the pentamer VPGXG,
      where any or all of repeats 32-671 can either be present or absent
<220> FEATURE:
<221> NAME/KEY: MISC_FEATURE
<222> LOCATION: (6)..(3360)
<223> OTHER INFORMATION: Xaa in each VPGXG pentamer repeat can
      independently be any amino acid except proline

<400> SEQUENCE: 13

Met Cys Gly Pro Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
    130                 135                 140

Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
                165                 170                 175

Pro Gly Xaa Gly Val Pro Gly Xaa Gly Val Pro Gly Xaa Gly Val Pro
            180                 185                 190
```

-continued

Gly Xaa Gly Val Pro Gly Xaa Gly Val Pro Gly Xaa Gly Val Pro Gly
         195                 200                 205

Xaa Gly Val Pro Gly Xaa Gly Val Pro Gly Xaa Gly Val Pro Gly Xaa
        210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
                245                 250                 255

Pro Gly Xaa Gly Val Pro Gly Xaa Gly Val Pro Gly Xaa Gly Val Pro
            260                 265                 270

Gly Xaa Gly Val Pro Gly Xaa Gly Val Pro Gly Xaa Gly Val Pro Gly
        275                 280                 285

Xaa Gly Val Pro Gly Xaa Gly Val Pro Gly Xaa Gly Val Pro Gly Xaa
        290                 295                 300

Gly Val Pro Gly Xaa Gly Val Pro Gly Xaa Gly Val Pro Gly Xaa Gly
305                 310                 315                 320

Val Pro Gly Xaa Gly Val Pro Gly Xaa Gly Val Pro Gly Xaa Gly Val
                325                 330                 335

Pro Gly Xaa Gly Val Pro Gly Xaa Gly Val Pro Gly Xaa Gly Val Pro
            340                 345                 350

Gly Xaa Gly Val Pro Gly Xaa Gly Val Pro Gly Xaa Gly Val Pro Gly
        355                 360                 365

Xaa Gly Val Pro Gly Xaa Gly Val Pro Gly Xaa Gly Val Pro Gly Xaa
        370                 375                 380

Gly Val Pro Gly Xaa Gly Val Pro Gly Xaa Gly Val Pro Gly Xaa Gly
385                 390                 395                 400

Val Pro Gly Xaa Gly Val Pro Gly Xaa Gly Val Pro Gly Xaa Gly Val
                405                 410                 415

Pro Gly Xaa Gly Val Pro Gly Xaa Gly Val Pro Gly Xaa Gly Val Pro
            420                 425                 430

Gly Xaa Gly Val Pro Gly Xaa Gly Val Pro Gly Xaa Gly Val Pro Gly
        435                 440                 445

Xaa Gly Val Pro Gly Xaa Gly Val Pro Gly Xaa Gly Val Pro Gly Xaa
        450                 455                 460

Gly Val Pro Gly Xaa Gly Val Pro Gly Xaa Gly Val Pro Gly Xaa Gly
465                 470                 475                 480

Val Pro Gly Xaa Gly Val Pro Gly Xaa Gly Val Pro Gly Xaa Gly Val
                485                 490                 495

Pro Gly Xaa Gly Val Pro Gly Xaa Gly Val Pro Gly Xaa Gly Val Pro
            500                 505                 510

Gly Xaa Gly Val Pro Gly Xaa Gly Val Pro Gly Xaa Gly Val Pro Gly
        515                 520                 525

Xaa Gly Val Pro Gly Xaa Gly Val Pro Gly Xaa Gly Val Pro Gly Xaa
        530                 535                 540

Gly Val Pro Gly Xaa Gly Val Pro Gly Xaa Gly Val Pro Gly Xaa Gly
545                 550                 555                 560

Val Pro Gly Xaa Gly Val Pro Gly Xaa Gly Val Pro Gly Xaa Gly Val
                565                 570                 575

Pro Gly Xaa Gly Val Pro Gly Xaa Gly Val Pro Gly Xaa Gly Val Pro
            580                 585                 590

Gly Xaa Gly Val Pro Gly Xaa Gly Val Pro Gly Xaa Gly Val Pro Gly
        595                 600                 605

Xaa Gly Val Pro Gly Xaa Gly Val Pro Gly Xaa Gly Val Pro Gly Xaa

```
                610                 615                 620
Gly Val Pro Gly Xaa Gly Val Pro Gly Xaa Gly Val Pro Gly Xaa Gly
625                 630                 635                 640

Val Pro Gly Xaa Gly Val Pro Gly Xaa Gly Val Pro Gly Xaa Gly Val
                645                 650                 655

Pro Gly Xaa Gly Val Pro Gly Xaa Gly Val Pro Gly Xaa Gly Val Pro
            660                 665                 670

Gly Xaa Gly Val Pro Gly Xaa Gly Val Pro Gly Xaa Gly Val Pro Gly
        675                 680                 685

Xaa Gly Val Pro Gly Xaa Gly Val Pro Gly Xaa Gly Val Pro Gly Xaa
690                 695                 700

Gly Val Pro Gly Xaa Gly Val Pro Gly Xaa Gly Val Pro Gly Xaa Gly
705                 710                 715                 720

Val Pro Gly Xaa Gly Val Pro Gly Xaa Gly Val Pro Gly Xaa Gly Val
                725                 730                 735

Pro Gly Xaa Gly Val Pro Gly Xaa Gly Val Pro Gly Xaa Gly Val Pro
            740                 745                 750

Gly Xaa Gly Val Pro Gly Xaa Gly Val Pro Gly Xaa Gly Val Pro Gly
        755                 760                 765

Xaa Gly Val Pro Gly Xaa Gly Val Pro Gly Xaa Gly Val Pro Gly Xaa
770                 775                 780

Gly Val Pro Gly Xaa Gly Val Pro Gly Xaa Gly Val Pro Gly Xaa Gly
785                 790                 795                 800

Val Pro Gly Xaa Gly Val Pro Gly Xaa Gly Val Pro Gly Xaa Gly Val
                805                 810                 815

Pro Gly Xaa Gly Val Pro Gly Xaa Gly Val Pro Gly Xaa Gly Val Pro
            820                 825                 830

Gly Xaa Gly Val Pro Gly Xaa Gly Val Pro Gly Xaa Gly Val Pro Gly
        835                 840                 845

Xaa Gly Val Pro Gly Xaa Gly Val Pro Gly Xaa Gly Val Pro Gly Xaa
850                 855                 860

Gly Val Pro Gly Xaa Gly Val Pro Gly Xaa Gly Val Pro Gly Xaa Gly
865                 870                 875                 880

Val Pro Gly Xaa Gly Val Pro Gly Xaa Gly Val Pro Gly Xaa Gly Val
                885                 890                 895

Pro Gly Xaa Gly Val Pro Gly Xaa Gly Val Pro Gly Xaa Gly Val Pro
            900                 905                 910

Gly Xaa Gly Val Pro Gly Xaa Gly Val Pro Gly Xaa Gly Val Pro Gly
        915                 920                 925

Xaa Gly Val Pro Gly Xaa Gly Val Pro Gly Xaa Gly Val Pro Gly Xaa
930                 935                 940

Gly Val Pro Gly Xaa Gly Val Pro Gly Xaa Gly Val Pro Gly Xaa Gly
945                 950                 955                 960

Val Pro Gly Xaa Gly Val Pro Gly Xaa Gly Val Pro Gly Xaa Gly Val
                965                 970                 975

Pro Gly Xaa Gly Val Pro Gly Xaa Gly Val Pro Gly Xaa Gly Val Pro
            980                 985                 990

Gly Xaa Gly Val Pro Gly Xaa Gly  Val Pro Gly Xaa Gly  Val Pro Gly
        995                 1000                1005

Xaa Gly  Val Pro Gly Xaa Gly  Val Pro Gly Xaa Gly  Val Pro Gly
    1010                1015                1020

Xaa Gly  Val Pro Gly Xaa Gly  Val Pro Gly Xaa Gly  Val Pro Gly
    1025                1030                1035
```

Xaa Gly Val Pro Gly Xaa Gly Val Pro Gly Xaa Gly Val Pro Gly
    1040                1045                1050

Xaa Gly Val Pro Gly Xaa Gly Val Pro Gly Xaa Gly Val Pro Gly
    1055                1060                1065

Xaa Gly Val Pro Gly Xaa Gly Val Pro Gly Xaa Gly Val Pro Gly
    1070                1075                1080

Xaa Gly Val Pro Gly Xaa Gly Val Pro Gly Xaa Gly Val Pro Gly
    1085                1090                1095

Xaa Gly Val Pro Gly Xaa Gly Val Pro Gly Xaa Gly Val Pro Gly
    1100                1105                1110

Xaa Gly Val Pro Gly Xaa Gly Val Pro Gly Xaa Gly Val Pro Gly
    1115                1120                1125

Xaa Gly Val Pro Gly Xaa Gly Val Pro Gly Xaa Gly Val Pro Gly
    1130                1135                1140

Xaa Gly Val Pro Gly Xaa Gly Val Pro Gly Xaa Gly Val Pro Gly
    1145                1150                1155

Xaa Gly Val Pro Gly Xaa Gly Val Pro Gly Xaa Gly Val Pro Gly
    1160                1165                1170

Xaa Gly Val Pro Gly Xaa Gly Val Pro Gly Xaa Gly Val Pro Gly
    1175                1180                1185

Xaa Gly Val Pro Gly Xaa Gly Val Pro Gly Xaa Gly Val Pro Gly
    1190                1195                1200

Xaa Gly Val Pro Gly Xaa Gly Val Pro Gly Xaa Gly Val Pro Gly
    1205                1210                1215

Xaa Gly Val Pro Gly Xaa Gly Val Pro Gly Xaa Gly Val Pro Gly
    1220                1225                1230

Xaa Gly Val Pro Gly Xaa Gly Val Pro Gly Xaa Gly Val Pro Gly
    1235                1240                1245

Xaa Gly Val Pro Gly Xaa Gly Val Pro Gly Xaa Gly Val Pro Gly
    1250                1255                1260

Xaa Gly Val Pro Gly Xaa Gly Val Pro Gly Xaa Gly Val Pro Gly
    1265                1270                1275

Xaa Gly Val Pro Gly Xaa Gly Val Pro Gly Xaa Gly Val Pro Gly
    1280                1285                1290

Xaa Gly Val Pro Gly Xaa Gly Val Pro Gly Xaa Gly Val Pro Gly
    1295                1300                1305

Xaa Gly Val Pro Gly Xaa Gly Val Pro Gly Xaa Gly Val Pro Gly
    1310                1315                1320

Xaa Gly Val Pro Gly Xaa Gly Val Pro Gly Xaa Gly Val Pro Gly
    1325                1330                1335

Xaa Gly Val Pro Gly Xaa Gly Val Pro Gly Xaa Gly Val Pro Gly
    1340                1345                1350

Xaa Gly Val Pro Gly Xaa Gly Val Pro Gly Xaa Gly Val Pro Gly
    1355                1360                1365

Xaa Gly Val Pro Gly Xaa Gly Val Pro Gly Xaa Gly Val Pro Gly
    1370                1375                1380

Xaa Gly Val Pro Gly Xaa Gly Val Pro Gly Xaa Gly Val Pro Gly
    1385                1390                1395

Xaa Gly Val Pro Gly Xaa Gly Val Pro Gly Xaa Gly Val Pro Gly
    1400                1405                1410

Xaa Gly Val Pro Gly Xaa Gly Val Pro Gly Xaa Gly Val Pro Gly
    1415                1420                1425

-continued

Xaa Gly Val Pro Gly Xaa Gly Val Pro Gly Xaa Gly Val Pro Gly
1430                1435                1440

Xaa Gly Val Pro Gly Xaa Gly Val Pro Gly Xaa Gly Val Pro Gly
1445                1450                1455

Xaa Gly Val Pro Gly Xaa Gly Val Pro Gly Xaa Gly Val Pro Gly
1460                1465                1470

Xaa Gly Val Pro Gly Xaa Gly Val Pro Gly Xaa Gly Val Pro Gly
1475                1480                1485

Xaa Gly Val Pro Gly Xaa Gly Val Pro Gly Xaa Gly Val Pro Gly
1490                1495                1500

Xaa Gly Val Pro Gly Xaa Gly Val Pro Gly Xaa Gly Val Pro Gly
1505                1510                1515

Xaa Gly Val Pro Gly Xaa Gly Val Pro Gly Xaa Gly Val Pro Gly
1520                1525                1530

Xaa Gly Val Pro Gly Xaa Gly Val Pro Gly Xaa Gly Val Pro Gly
1535                1540                1545

Xaa Gly Val Pro Gly Xaa Gly Val Pro Gly Xaa Gly Val Pro Gly
1550                1555                1560

Xaa Gly Val Pro Gly Xaa Gly Val Pro Gly Xaa Gly Val Pro Gly
1565                1570                1575

Xaa Gly Val Pro Gly Xaa Gly Val Pro Gly Xaa Gly Val Pro Gly
1580                1585                1590

Xaa Gly Val Pro Gly Xaa Gly Val Pro Gly Xaa Gly Val Pro Gly
1595                1600                1605

Xaa Gly Val Pro Gly Xaa Gly Val Pro Gly Xaa Gly Val Pro Gly
1610                1615                1620

Xaa Gly Val Pro Gly Xaa Gly Val Pro Gly Xaa Gly Val Pro Gly
1625                1630                1635

Xaa Gly Val Pro Gly Xaa Gly Val Pro Gly Xaa Gly Val Pro Gly
1640                1645                1650

Xaa Gly Val Pro Gly Xaa Gly Val Pro Gly Xaa Gly Val Pro Gly
1655                1660                1665

Xaa Gly Val Pro Gly Xaa Gly Val Pro Gly Xaa Gly Val Pro Gly
1670                1675                1680

Xaa Gly Val Pro Gly Xaa Gly Val Pro Gly Xaa Gly Val Pro Gly
1685                1690                1695

Xaa Gly Val Pro Gly Xaa Gly Val Pro Gly Xaa Gly Val Pro Gly
1700                1705                1710

Xaa Gly Val Pro Gly Xaa Gly Val Pro Gly Xaa Gly Val Pro Gly
1715                1720                1725

Xaa Gly Val Pro Gly Xaa Gly Val Pro Gly Xaa Gly Val Pro Gly
1730                1735                1740

Xaa Gly Val Pro Gly Xaa Gly Val Pro Gly Xaa Gly Val Pro Gly
1745                1750                1755

Xaa Gly Val Pro Gly Xaa Gly Val Pro Gly Xaa Gly Val Pro Gly
1760                1765                1770

Xaa Gly Val Pro Gly Xaa Gly Val Pro Gly Xaa Gly Val Pro Gly
1775                1780                1785

Xaa Gly Val Pro Gly Xaa Gly Val Pro Gly Xaa Gly Val Pro Gly
1790                1795                1800

Xaa Gly Val Pro Gly Xaa Gly Val Pro Gly Xaa Gly Val Pro Gly
1805                1810                1815

Xaa Gly Val Pro Gly Xaa Gly Val Pro Gly Xaa Gly Val Pro Gly

-continued

```
            1820                1825                1830

Xaa Gly Val Pro Gly Xaa Gly Val Pro Gly Xaa Gly Val Pro Gly
    1835                1840                1845

Xaa Gly Val Pro Gly Xaa Gly Val Pro Gly Xaa Gly Val Pro Gly
    1850                1855                1860

Xaa Gly Val Pro Gly Xaa Gly Val Pro Gly Xaa Gly Val Pro Gly
    1865                1870                1875

Xaa Gly Val Pro Gly Xaa Gly Val Pro Gly Xaa Gly Val Pro Gly
    1880                1885                1890

Xaa Gly Val Pro Gly Xaa Gly Val Pro Gly Xaa Gly Val Pro Gly
    1895                1900                1905

Xaa Gly Val Pro Gly Xaa Gly Val Pro Gly Xaa Gly Val Pro Gly
    1910                1915                1920

Xaa Gly Val Pro Gly Xaa Gly Val Pro Gly Xaa Gly Val Pro Gly
    1925                1930                1935

Xaa Gly Val Pro Gly Xaa Gly Val Pro Gly Xaa Gly Val Pro Gly
    1940                1945                1950

Xaa Gly Val Pro Gly Xaa Gly Val Pro Gly Xaa Gly Val Pro Gly
    1955                1960                1965

Xaa Gly Val Pro Gly Xaa Gly Val Pro Gly Xaa Gly Val Pro Gly
    1970                1975                1980

Xaa Gly Val Pro Gly Xaa Gly Val Pro Gly Xaa Gly Val Pro Gly
    1985                1990                1995

Xaa Gly Val Pro Gly Xaa Gly Val Pro Gly Xaa Gly Val Pro Gly
    2000                2005                2010

Xaa Gly Val Pro Gly Xaa Gly Val Pro Gly Xaa Gly Val Pro Gly
    2015                2020                2025

Xaa Gly Val Pro Gly Xaa Gly Val Pro Gly Xaa Gly Val Pro Gly
    2030                2035                2040

Xaa Gly Val Pro Gly Xaa Gly Val Pro Gly Xaa Gly Val Pro Gly
    2045                2050                2055

Xaa Gly Val Pro Gly Xaa Gly Val Pro Gly Xaa Gly Val Pro Gly
    2060                2065                2070

Xaa Gly Val Pro Gly Xaa Gly Val Pro Gly Xaa Gly Val Pro Gly
    2075                2080                2085

Xaa Gly Val Pro Gly Xaa Gly Val Pro Gly Xaa Gly Val Pro Gly
    2090                2095                2100

Xaa Gly Val Pro Gly Xaa Gly Val Pro Gly Xaa Gly Val Pro Gly
    2105                2110                2115

Xaa Gly Val Pro Gly Xaa Gly Val Pro Gly Xaa Gly Val Pro Gly
    2120                2125                2130

Xaa Gly Val Pro Gly Xaa Gly Val Pro Gly Xaa Gly Val Pro Gly
    2135                2140                2145

Xaa Gly Val Pro Gly Xaa Gly Val Pro Gly Xaa Gly Val Pro Gly
    2150                2155                2160

Xaa Gly Val Pro Gly Xaa Gly Val Pro Gly Xaa Gly Val Pro Gly
    2165                2170                2175

Xaa Gly Val Pro Gly Xaa Gly Val Pro Gly Xaa Gly Val Pro Gly
    2180                2185                2190

Xaa Gly Val Pro Gly Xaa Gly Val Pro Gly Xaa Gly Val Pro Gly
    2195                2200                2205

Xaa Gly Val Pro Gly Xaa Gly Val Pro Gly Xaa Gly Val Pro Gly
    2210                2215                2220
```

```
Xaa Gly Val Pro Gly Xaa Gly Val Pro Gly Xaa Gly Val Pro Gly
    2225                2230                2235

Xaa Gly Val Pro Gly Xaa Gly Val Pro Gly Xaa Gly Val Pro Gly
    2240                2245                2250

Xaa Gly Val Pro Gly Xaa Gly Val Pro Gly Xaa Gly Val Pro Gly
    2255                2260                2265

Xaa Gly Val Pro Gly Xaa Gly Val Pro Gly Xaa Gly Val Pro Gly
    2270                2275                2280

Xaa Gly Val Pro Gly Xaa Gly Val Pro Gly Xaa Gly Val Pro Gly
    2285                2290                2295

Xaa Gly Val Pro Gly Xaa Gly Val Pro Gly Xaa Gly Val Pro Gly
    2300                2305                2310

Xaa Gly Val Pro Gly Xaa Gly Val Pro Gly Xaa Gly Val Pro Gly
    2315                2320                2325

Xaa Gly Val Pro Gly Xaa Gly Val Pro Gly Xaa Gly Val Pro Gly
    2330                2335                2340

Xaa Gly Val Pro Gly Xaa Gly Val Pro Gly Xaa Gly Val Pro Gly
    2345                2350                2355

Xaa Gly Val Pro Gly Xaa Gly Val Pro Gly Xaa Gly Val Pro Gly
    2360                2365                2370

Xaa Gly Val Pro Gly Xaa Gly Val Pro Gly Xaa Gly Val Pro Gly
    2375                2380                2385

Xaa Gly Val Pro Gly Xaa Gly Val Pro Gly Xaa Gly Val Pro Gly
    2390                2395                2400

Xaa Gly Val Pro Gly Xaa Gly Val Pro Gly Xaa Gly Val Pro Gly
    2405                2410                2415

Xaa Gly Val Pro Gly Xaa Gly Val Pro Gly Xaa Gly Val Pro Gly
    2420                2425                2430

Xaa Gly Val Pro Gly Xaa Gly Val Pro Gly Xaa Gly Val Pro Gly
    2435                2440                2445

Xaa Gly Val Pro Gly Xaa Gly Val Pro Gly Xaa Gly Val Pro Gly
    2450                2455                2460

Xaa Gly Val Pro Gly Xaa Gly Val Pro Gly Xaa Gly Val Pro Gly
    2465                2470                2475

Xaa Gly Val Pro Gly Xaa Gly Val Pro Gly Xaa Gly Val Pro Gly
    2480                2485                2490

Xaa Gly Val Pro Gly Xaa Gly Val Pro Gly Xaa Gly Val Pro Gly
    2495                2500                2505

Xaa Gly Val Pro Gly Xaa Gly Val Pro Gly Xaa Gly Val Pro Gly
    2510                2515                2520

Xaa Gly Val Pro Gly Xaa Gly Val Pro Gly Xaa Gly Val Pro Gly
    2525                2530                2535

Xaa Gly Val Pro Gly Xaa Gly Val Pro Gly Xaa Gly Val Pro Gly
    2540                2545                2550

Xaa Gly Val Pro Gly Xaa Gly Val Pro Gly Xaa Gly Val Pro Gly
    2555                2560                2565

Xaa Gly Val Pro Gly Xaa Gly Val Pro Gly Xaa Gly Val Pro Gly
    2570                2575                2580

Xaa Gly Val Pro Gly Xaa Gly Val Pro Gly Xaa Gly Val Pro Gly
    2585                2590                2595

Xaa Gly Val Pro Gly Xaa Gly Val Pro Gly Xaa Gly Val Pro Gly
    2600                2605                2610
```

```
Xaa Gly  Val Pro Gly Xaa Gly  Val Pro Gly Xaa Gly  Val Pro Gly
    2615                 2620                 2625

Xaa Gly  Val Pro Gly Xaa Gly  Val Pro Gly Xaa Gly  Val Pro Gly
    2630                 2635                 2640

Xaa Gly  Val Pro Gly Xaa Gly  Val Pro Gly Xaa Gly  Val Pro Gly
    2645                 2650                 2655

Xaa Gly  Val Pro Gly Xaa Gly  Val Pro Gly Xaa Gly  Val Pro Gly
    2660                 2665                 2670

Xaa Gly  Val Pro Gly Xaa Gly  Val Pro Gly Xaa Gly  Val Pro Gly
    2675                 2680                 2685

Xaa Gly  Val Pro Gly Xaa Gly  Val Pro Gly Xaa Gly  Val Pro Gly
    2690                 2695                 2700

Xaa Gly  Val Pro Gly Xaa Gly  Val Pro Gly Xaa Gly  Val Pro Gly
    2705                 2710                 2715

Xaa Gly  Val Pro Gly Xaa Gly  Val Pro Gly Xaa Gly  Val Pro Gly
    2720                 2725                 2730

Xaa Gly  Val Pro Gly Xaa Gly  Val Pro Gly Xaa Gly  Val Pro Gly
    2735                 2740                 2745

Xaa Gly  Val Pro Gly Xaa Gly  Val Pro Gly Xaa Gly  Val Pro Gly
    2750                 2755                 2760

Xaa Gly  Val Pro Gly Xaa Gly  Val Pro Gly Xaa Gly  Val Pro Gly
    2765                 2770                 2775

Xaa Gly  Val Pro Gly Xaa Gly  Val Pro Gly Xaa Gly  Val Pro Gly
    2780                 2785                 2790

Xaa Gly  Val Pro Gly Xaa Gly  Val Pro Gly Xaa Gly  Val Pro Gly
    2795                 2800                 2805

Xaa Gly  Val Pro Gly Xaa Gly  Val Pro Gly Xaa Gly  Val Pro Gly
    2810                 2815                 2820

Xaa Gly  Val Pro Gly Xaa Gly  Val Pro Gly Xaa Gly  Val Pro Gly
    2825                 2830                 2835

Xaa Gly  Val Pro Gly Xaa Gly  Val Pro Gly Xaa Gly  Val Pro Gly
    2840                 2845                 2850

Xaa Gly  Val Pro Gly Xaa Gly  Val Pro Gly Xaa Gly  Val Pro Gly
    2855                 2860                 2865

Xaa Gly  Val Pro Gly Xaa Gly  Val Pro Gly Xaa Gly  Val Pro Gly
    2870                 2875                 2880

Xaa Gly  Val Pro Gly Xaa Gly  Val Pro Gly Xaa Gly  Val Pro Gly
    2885                 2890                 2895

Xaa Gly  Val Pro Gly Xaa Gly  Val Pro Gly Xaa Gly  Val Pro Gly
    2900                 2905                 2910

Xaa Gly  Val Pro Gly Xaa Gly  Val Pro Gly Xaa Gly  Val Pro Gly
    2915                 2920                 2925

Xaa Gly  Val Pro Gly Xaa Gly  Val Pro Gly Xaa Gly  Val Pro Gly
    2930                 2935                 2940

Xaa Gly  Val Pro Gly Xaa Gly  Val Pro Gly Xaa Gly  Val Pro Gly
    2945                 2950                 2955

Xaa Gly  Val Pro Gly Xaa Gly  Val Pro Gly Xaa Gly  Val Pro Gly
    2960                 2965                 2970

Xaa Gly  Val Pro Gly Xaa Gly  Val Pro Gly Xaa Gly  Val Pro Gly
    2975                 2980                 2985

Xaa Gly  Val Pro Gly Xaa Gly  Val Pro Gly Xaa Gly  Val Pro Gly
    2990                 2995                 3000

Xaa Gly  Val Pro Gly Xaa Gly  Val Pro Gly Xaa Gly  Val Pro Gly
```

-continued

```
                    3005                3010                3015

Xaa Gly Val Pro Gly Xaa Gly Val Pro Gly Xaa Gly Val Pro Gly
    3020                3025                3030

Xaa Gly Val Pro Gly Xaa Gly Val Pro Gly Xaa Gly Val Pro Gly
    3035                3040                3045

Xaa Gly Val Pro Gly Xaa Gly Val Pro Gly Xaa Gly Val Pro Gly
    3050                3055                3060

Xaa Gly Val Pro Gly Xaa Gly Val Pro Gly Xaa Gly Val Pro Gly
    3065                3070                3075

Xaa Gly Val Pro Gly Xaa Gly Val Pro Gly Xaa Gly Val Pro Gly
    3080                3085                3090

Xaa Gly Val Pro Gly Xaa Gly Val Pro Gly Xaa Gly Val Pro Gly
    3095                3100                3105

Xaa Gly Val Pro Gly Xaa Gly Val Pro Gly Xaa Gly Val Pro Gly
    3110                3115                3120

Xaa Gly Val Pro Gly Xaa Gly Val Pro Gly Xaa Gly Val Pro Gly
    3125                3130                3135

Xaa Gly Val Pro Gly Xaa Gly Val Pro Gly Xaa Gly Val Pro Gly
    3140                3145                3150

Xaa Gly Val Pro Gly Xaa Gly Val Pro Gly Xaa Gly Val Pro Gly
    3155                3160                3165

Xaa Gly Val Pro Gly Xaa Gly Val Pro Gly Xaa Gly Val Pro Gly
    3170                3175                3180

Xaa Gly Val Pro Gly Xaa Gly Val Pro Gly Xaa Gly Val Pro Gly
    3185                3190                3195

Xaa Gly Val Pro Gly Xaa Gly Val Pro Gly Xaa Gly Val Pro Gly
    3200                3205                3210

Xaa Gly Val Pro Gly Xaa Gly Val Pro Gly Xaa Gly Val Pro Gly
    3215                3220                3225

Xaa Gly Val Pro Gly Xaa Gly Val Pro Gly Xaa Gly Val Pro Gly
    3230                3235                3240

Xaa Gly Val Pro Gly Xaa Gly Val Pro Gly Xaa Gly Val Pro Gly
    3245                3250                3255

Xaa Gly Val Pro Gly Xaa Gly Val Pro Gly Xaa Gly Val Pro Gly
    3260                3265                3270

Xaa Gly Val Pro Gly Xaa Gly Val Pro Gly Xaa Gly Val Pro Gly
    3275                3280                3285

Xaa Gly Val Pro Gly Xaa Gly Val Pro Gly Xaa Gly Val Pro Gly
    3290                3295                3300

Xaa Gly Val Pro Gly Xaa Gly Val Pro Gly Xaa Gly Val Pro Gly
    3305                3310                3315

Xaa Gly Val Pro Gly Xaa Gly Val Pro Gly Xaa Gly Val Pro Gly
    3320                3325                3330

Xaa Gly Val Pro Gly Xaa Gly Val Pro Gly Xaa Gly Val Pro Gly
    3335                3340                3345

Xaa Gly Val Pro Gly Xaa Gly Val Pro Gly Xaa Gly Trp Pro Gly
    3350                3355                3360

Ser Gly
    3365
```

MOLECULAR-SIZE OF ELASTIN-LIKE POLYPEPTIDE DELIVERY SYSTEM FOR THERAPEUTICS MODULATES INTRARENAL DEPOSITION AND BIOAVAILABILITY

RELATED APPLICATIONS

This application claims the benefit of U.S. Provisional Application Ser. No. 62/826,413, filed Mar. 29, 2019, and is a continuation-in-part of U.S. patent application Ser. No. 16/397,962, filed Apr. 29, 2019, which is a continuation of U.S. patent application Ser. No. 15/517,805, filed Apr. 7, 2017, now allowed, which is the National Stage of International Patent Application No. PCT/US2015/060438, filed Nov. 12, 2015, which claims the benefit of U.S. Provisional Application Ser. No. 62/078,752 filed Nov. 12, 2014, the entire disclosures of which are incorporated herein by this reference.

STATEMENT OF GOVERNMENT SUPPORT

This presently-disclosed subject matter was made with government support under grant number R01HL095638, R01HL121527, and R41DK109737 awarded by the National Institutes of Health. The government has certain rights in it.

SEQUENCE LISTING

The instant application contains a Sequence Listing which has been submitted in ASCII format via EFS-Web and is hereby incorporated by reference in its entirety. The ASCII copy of the Sequence Listing, which was created on Aug. 10, 2020, is named 11637N-181021C.txt, and is 76.4 kilobytes in size.

TECHNICAL FIELD

The presently-disclosed subject matter generally relates to a composition and method for therapeutic agent delivery of kidney diseases treatment. More particularly, the presently-disclosed subject matter relates to a composition comprising an elastin-like polypeptide (ELP) coupled to kidney targeting peptides and a therapeutic agent or agents, and a method of delivering the composition to a subject in need thereof.

INTRODUCTION

The kidney plays a critical role in sodium/water balance, maintenance of blood pressure, and removal of waste products from the circulatory system. Damage or disease to the kidneys can have very serious consequences including the often irreversible need to place patients on hemodialysis for the remainder of their life. Therefore, the kidney is an important drug target, and therapies that can prevent loss of kidney function or even restore function in damaged kidneys would have great clinical value.

Chronic kidney disease (CKD) is a progressive disorder affecting almost 14% of the general adult population, and this disease has shown a continuous growth over the past 2 decades. Patients with CKD have higher rates of hospitalization, greater mortality, shorter life expectancy, and their healthcare costs are up to 5 times more expensive than non-CKD patients. Thus, treatments to slow, halt, or reverse the progression of CKD could have a significant impact. Chronic renal vascular disease (RVD), often associated with renal artery stenosis, can deteriorate renal function and lead to CKD and end-stage renal disease. Despite the availability of treatments for RVD including drugs and renal angioplasty, renal function does not improve or even deteriorates in over half of the patients undergoing these treatments. This evidence shows that treatments available are still largely ineffective and highlights a pressing need for novel therapeutic strategies for the growing population of patients suffering from RVD.

More recently, elastin-like polypeptides (ELPs) have been investigated as possible drug carriers in many different disease areas. Elastin-like polypeptides (ELPs) are genetically engineered proteins utilized as a delivery system for therapeutics. Modifications of the sequence composition and length can be achieved by recursive directional ligation, and their influence on the polypeptide's $T_t$ have been extensively studied. Additionally, the ELP sequence is easily modified to include therapeutic peptides and proteins (TP). Additionally, small molecule drugs can easily be chemically attached. These ELP fusions confer increased stability to therapeutic peptides and protein cargo, and they can increase solubility and reduce off-target toxicity of small molecule drugs. However, careful analysis of how their physical properties, including chain length and hydrodynamic radius, influence their in vivo behavior has not been systematically described. Accordingly, there remains a need for an ELP with physical properties providing predictable in vivo behavior.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature (s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a renal cortex targeting elastin-like polypeptide (ELP) including up to 95 repeat units having the sequence VPGXG (SEQ ID NO: 1), wherein X in each of the repeat units is individually selected from the group consisting of any amino acid except proline. In one embodiment, the ELP comprises between 5 and 95 of the repeat units. In another embodiment, the ELP comprises between 31 and 95 of the repeat units. In a further embodiment, the ELP comprises between 63 and 95 of the repeat units. In one embodiment, the ELP comprises a molecular weight of up to 38 kDa. In another embodiment, the ELP comprises a molecular weight of between 13 kDa and 38 kDa. In some embodiments, the repeat units include V:G:A in a 1:4:3 ratio. In some embodiments, the ELP further includes one or more of a therapeutic agent or agents, a drug binding domain, a targeting domain, and a cell penetrating peptide.

Also provided herein, in some embodiments, is a renal medulla and cortex targeting elastin-like polypeptide (ELP) including at least 95 repeat units having the sequence VPGXG (SEQ ID NO: 1), wherein X in each of the repeat units is individually selected from the group consisting of any amino acid except proline. In one embodiment, the ELP comprises between 95 and 671 of the repeat units. In another embodiment, the ELP comprises between 95 and 450 of the repeat units. In a further embodiment, the ELP comprises between 95 and 287 of the repeat units. In one embodiment, the ELP comprises a molecular weight of at least 38 kDa. In another embodiment, the ELP comprises a molecular weight of between 38 kDa and 257 kDa. In some embodiments, the repeat units include V:G:A in a 1:4:3 ratio. In some embodiments, the ELP further includes one or more of a group selected from a therapeutic agent or agents, a drug binding domain, a targeting domain, and a cell penetrating peptide.

Further provided herein, in some embodiments, is a method of treating a renal disorder, the method including administering an elastin-like peptide (ELP) and a therapeutic drug to a subject in need thereof, where the ELP includes up to 671 repeat units having the sequence VPGXG (SEQ ID NO: 1), and X in each of the repeat units is individually selected from the group consisting of any amino acid except proline. In some embodiments, the ELP includes up to 95 of the repeat units. In some embodiments, the ELP includes at least 95 of the repeat units.

Still further provided herein, in some embodiments, is a method of decreasing the clearance of an elastin-like polypeptides ELP from plasma or a tissue, the method comprising increasing the number of repeat units in the ELP.

Further features and advantages of the presently-disclosed subject matter will become evident to those of ordinary skill in the art after a study of the description, figures, and non-limiting examples in this document.

BRIEF DESCRIPTION OF THE DRAWINGS

FIGS. 2A-D include a series of images and graphs demonstrating the enhancement of kidney specificity using Kidney Targeting Peptides. (A) Rats were administered fluorescently labeled ELP, SynB1-ELP, Tat-ELP, or KTP-ELP, and organ biodistribution was determined by ex vivo fluorescence imaging. (B) Quantitative analysis showed that the highest accumulation of all peptides was in the kidney, and the targeting agents significantly increased kidney deposition. KTP-ELP had the highest specificity for the kidney as assessed by (C) kidney:liver and (D) kidney:heart ratios.

FIGS. 8A-E include a series of bar graphs and images demonstrating that ELP-VEGF maintains its pro-angiogenic activity. (A) Stimulation of HGME cell proliferation was determined by exposing HGME cells to ELP control, unconjugated VEGF, or ELP-VEGF for 72 h, and viable cells were detected using the MTS cell proliferation assay. (B and C) To determine if ELP-VEGF could stimulate tube formation in primary endothelial cells, HGME cells were plated on growth factor reduced Matrigel, and the media was supplemented with the indicated proteins. Tube formation was assessed after 5 h of exposure to the proteins. (D and E) To determine whether ELP-VEGF functions as a chemokine for primary endothelial cells, HGME cells were plated in the top well of Matrigel-coated Boyden chambers, and media in the bottom well was supplemented with the test proteins. Migrating cells were detected on the bottom surface of the membranes by crystal violet staining after 16-24 h of protein exposure. * Levels are significantly higher than untreated cells as assessed by a one-way ANOVA and post-hoc Bonferroni multiple comparison.

FIGS. 10A-C include bar graphs and tabular data demonstrating that ELP-VEGF is superior to unmodified VEGF at restoring renal function and microvascular density in the swine model of renal artery stenosis. Comparisons between intra-renal unbound VEGF vs. ELP-VEGF therapy on: (A) basal stenotic kidney RBF and GFR, expressed as % change compared to pre-treatment values; (B) RBF and GFR responses to intra-renal infusion of acetylcholine; (C) effects of the treatments on cortical and medullary MV density (3D micro-CT reconstruction, divided by MV diameter) in renovascular disease (RVD)+VEGF and RVD+ELP-VEGF treated kidneys. †$p<0.05$ vs. RVD/RVD+VEGF; ‡$p<0.05$ vs. 6 weeks; ‡‡$p<0.05$ vs. baseline; # $p=0.09$ vs. RVD.

DESCRIPTION OF EXEMPLARY EMBODIMENTS

Figure 1A:
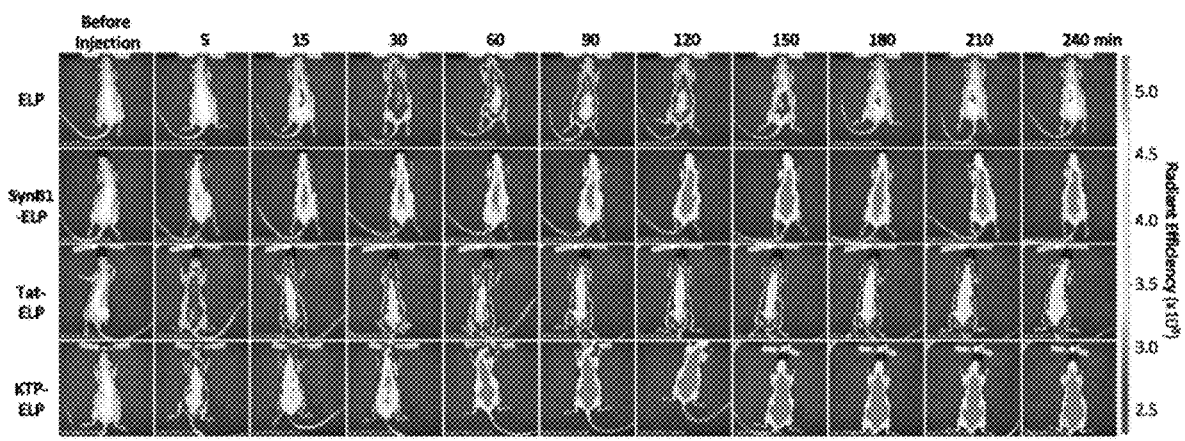
FIGS. 1A-B include a series of images and a graph depicting the biodistribution of kidney targeted ELPs in the rat. Rats were given fluorescently labeled ELP, Synb1-ELP, Tat-ELP, and KTP-ELP by intravenous injection. (A) Whole-body fluorescence was determined by in vivo fluorescence imaging at various times after injection. (B) The mean fluorescence intensity was determined at each time point and plotted to show tissue deposition and clearance. N=3 rats per treatment group.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. Further, while the terms used herein are believed to be well-understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter relates to a composition and method for therapeutic agent delivery for treatment of kidney diseases. More particularly, the presently-disclosed subject matter relates to a composition comprising an elastin-like polypeptide (ELP) coupled to a therapeutic agent or agents, and a method of delivering the composition to a subject in need thereof.

As used herein, the term "elastin-like polypeptide" or "ELP" refers to a synthetic protein containing structural peptide units, which may be repeating units, structurally related to, or derived from, sequences of the elastin protein. ELP is a macromolecular carrier that has several advantages. It is an inert and biodegradable macromolecule, giving it a good pharmacokinetic profile and very low immunogenicity. Additionally, ELPs can stabilize small proteins, small peptides, and/or small molecule therapeutic agent cargo in systemic circulation. Also, as opposed to chemically synthesized polymers, ELP is expressed in and easily purified from E. coli. Further, these ELPs are genetically engineered polypeptides that have a unique physical property called thermal responsiveness. That is, above a characteristic transition temperature, the polypeptide forms aggregates, while below the transition temperature, the aggregates re-dissolve.

In some embodiments, each ELP includes repeated units of a five amino-acid motif having the sequence VPGXG (SEQ ID NO: 1), where each X is individually selected from any amino acid except proline. These individual repeat units may be distributed throughout the ELP in any order, including randomly, in a repeating order, in blocks, or a combination thereof. Additionally or alternatively, the ELP may include any suitable ratio of repeat units having any amino except proline in the X position.

Since ELPs are genetically engineered rather than chemically synthesized, the sequence and molecular weight thereof can be precisely controlled. As such, the composition and/or length of the ELP sequence may be modified through know methods, such as, but not limited to, recursive directional ligation. For example, in some embodiments, the composition and/or length of the ELP sequence may be modified to include therapeutic proteins or peptides, targeting proteins or peptides, cell penetrating peptides, reactive sites for chemical attachment of therapeutic agents, or a combination thereof. Accordingly, when used as a delivery system for therapeutics, the ELPs disclosed herein provide certain therapeutic advantages to the therapeutic agent(s), such as, but not limited to, comparatively better stability, solubility, bioavailability, half-life, persistence, biological action of the therapeutic proteinaceous component or attached small molecule drug.

In some embodiments, the presently-disclosed subject matter is based, at least in part, on the effects of molecular weight on the pharmacokinetics, biodistribution, and renal deposition of elastin-like polypeptides (ELPs), as well as the discovery that different molecular weights provide drug delivery to different intra-renal targets. More specifically, provided herein are specific sized ELP constructs that differentially target the cortical and medullary regions in the kidney (i.e., renal cortex and renal medulla).

ELPs with up to about 671 repeat units and/or about 257 kDa accumulate in substantially higher levels in the kidney relative to other organs and exhibit high stability upon incubation in plasma maintained at body temperature. In some embodiments, the ELP half-life and/or hydrodynamic radius increases as the molecular weight of the ELP is increased. As will be appreciated by those skilled in the art, the more repeat units in the ELP, the higher the molecular weight thereof. Surprisingly, ELPs with more repeat units exhibit longer half-life (i.e., are cleared slower from the plasma and tissues) as compared to ELPs with less repeat units. For example, the terminal half-life of ELP compositions with higher molecular weights was 5 to 20-fold longer than smaller ELP proteins of 25 kDa or less. Additionally, the present inventors have unexpectedly and surprisingly found that at certain molecular weights, the ELPs differentially target various regions of the kidney. In particular, the present inventors found that, upon administration, ELPs with up to 95 repeat units and/or a molecular weight of up to 38 kDa accumulate or substantially accumulate solely in the renal cortex (cortical region), while ELPs with more than 95 repeat units and/or a molecular weight of more than 38 kDa accumulate in both the renal cortex and renal medulla (medullary region). Furthermore, the amount of ELP in the renal medulla increased, while the amount of ELP in the renal cortex decreased, with increasing sizes greater than 38 kDa.

Accordingly, in some embodiments, a renal cortex targeting ELP includes up to 95 repeat units, between 5 and 95 repeat units, between 10 and 95 repeat units, between 15 and 95 repeat units, between 20 and 95 repeat units, between 25 and 95 repeat units, between 30 and 95 repeat units, between 31 and 95 repeat units, between 63 and 95 repeat units, or any combination, sub-combination, range, or sub-range thereof. Additionally or alternatively, in some embodiments, the renal cortex targeting ELP includes a molecular weight of up to 38 kDa, between 5 and 38 kDa, between 13 and 38 kDa, between 25 and 38 kDa, or any combination, sub-combination, range, or sub-range thereof.

In other embodiments, a renal medulla targeting ELP includes greater than 95 repeat units, between 95 and 671, between 95 and 600, between 95 and 550, between 95 and 500, between 95 and 450, between 95 and 400, between 95 and 350, between 95 and 300, between 95 and 287 repeat units, or any combination, sub-combination, range, or sub-range thereof. Additionally or alternatively, in some embodiments, the renal medulla targeting ELP includes a molecular weight of greater than 38 kDa, between 38 and 257 kDa, between 38 and 110 kDa, or any combination, sub-combination, range, or sub-range thereof.

In some embodiments, the ELP includes a drug binding domain in place of or in addition to the fused and/or chemically attached therapeutic agent. The drug binding domain facilitates attachment of any suitable known or new small molecule therapeutic agent(s). In some embodiments, the drug binding domain is attached to the ELP carrier via a drug release domain to allow for selective release of the drug under particular environmental conditions or at specific sites within the body. In some embodiments, the drug binding domain improves delivery of the therapeutic agent. For example, the drug binding domain may improve the delivery of therapeutic agents to treat preeclampsia and other pregnancy related disorders, or to treat other diseases that happen to occur during pregnancy such as cancer. Additionally or alternatively, in some embodiments, the ELP coupled therapeutic system includes multiple copies of the therapeutic agent and/or drug binding domain to increase the amount of drug delivered. This may also include the use of two or more different therapeutic agents or different drugs attached to the ELP and/or drug binding domain(s) to achieve combination therapy. Other cases may include both a therapeutic agent/s and a drug binding domain/s to achieve simultaneous delivery of peptide/protein—based therapeutic agents with small molecule drugs.

The ELPs according to one or more of the embodiments disclosed herein facilitate the delivery of a therapeutic drug for treatment of renovascular disease, renal cancer treatment, and other renal related diseases and disorders. Accordingly, also provided herein, in some embodiments, is an ELP delivery system for treatment renal diseases and disorders. In some embodiments, the ELP delivery system includes an ELP according to one or more of the embodiments disclosed herein. In some embodiments, the ELP delivery system includes the ELP and one or more therapeutic drugs. One or more therapeutic drugs attached, encompassed, or otherwise associated with the ELP facilitate the delivery thereof. In some embodiments, the ELP delivery system includes different sized ELPs to deliver one or more therapeutic drugs to different portions of the kidney. For example, in one embodiment, the ELP delivery system includes a therapeutic drug associated with an ELP having up to 95 repeat units for specific delivery to the renal cortex. In another embodiment, the ELP delivery system includes a therapeutic drug associated with an ELP having greater than 95 repeat units for delivery to both the renal cortex and the renal medulla. In yet other embodiments, both therapeutic drugs, one having an ELP up to 95 repeat units and a second having an ELP with greater than 95 repeat units, can be used in combination.

Additionally or alternatively, in some embodiments, the presently-disclosed subject matter provides a kidney targeted drug delivery system composed of a ELP biopolymer carrier modified with a kidney targeting agent and a drug binding domain or a directly fused therapeutic peptide or protein. The kidney targeted drug carrier consists of one of several targeting peptides that confer kidney-specific delivery fused to a biopolymer based on elastin-like polypeptide (ELP). In some embodiments, a drug binding domain and/or a therapeutic peptide or protein is also fused to the ELP biopolymer. In some embodiments, the drug binding domain consists of a region containing multiple cysteine or lysine residues that can be used for covalent attachment of drugs. In some embodiments, in addition to covalent drug attachment, the therapeutic domain might contain therapeutic peptides or proteins designed to intervene in disease processes of the kidney.

When all domains are included in the same molecule, the targeting domain increases kidney deposition and confers kidney specificity, the ELP biopolymer provides mass that confers protection from degradation and rapid renal clearance, and the therapeutic domain and/or drug binding domain provides a mechanism for intervening in disease processes of the kidney. ELPs can be fused to virtually any therapeutic compound by simple molecular biology techniques. Thus, determining the feasibility of using ELP technology for renal therapy could have clinical ramifications that go beyond chronic RVD and may extend to CKD from different etiologies.

In some embodiments, the presently disclosed subject matter provides a composition comprising an elastin-like polypeptide (ELP), a kidney targeting agent coupled to the ELP, and a therapeutic agent and/or a drug binding domain coupled to the ELP. In some embodiments, the presently disclosed subject matter further includes a pharmaceutically acceptable carrier. In some embodiments, the ELP includes an amino acid sequence having at least about 5 repeats of SEQ ID NO: 1, and the composition enhances the deposition and retention of the therapeutic agent in the kidney relative to the non-conjugated therapeutic. In some embodiments, the ELP includes an amino acid sequence comprising about 5 repeats to about 320 repeats of SEQ ID NO: 1. In some embodiments, X in SEQ ID NO: 1 is any amino acid except proline. In some embodiments, X in SEQ ID NO: 1 is Val, Ala, and Gly in a ratio range of about 0-1:0-8:0-8.

The terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The term "kidney targeting agents" refers to short peptides designed to have specificity for the vascular beds or other cell types of specific organs such as kidney.

The term "therapeutic agent" and the like is used herein to refer to substances that can alter, inhibit, activate, catalyze, or otherwise affect a biological or chemical event in a subject. In some embodiments a therapeutic agent has the effect of treating a disease, condition, or disorder in a subject, and possibly in the kidney of a subject. Exemplary active agents include, but are not limited to, enzymes, organic catalysts, ribozymes, organometallics, proteins, glycoproteins, peptides, polyamino acids, antibodies, nucleic acids, steroidal molecules, antibiotics, antibacterial agents, anti-inflammatory agents, antivirals, antimycotics, anticancer agents, analgesic agents, antirejection agents, immunosuppressants, cytokines, carbohydrates, oleophobics, lipids, pharmaceuticals (i.e., drugs; including small molecules), chemotherapeutics, and combinations thereof.

Non-limiting examples of the ELP sequences include an amino acid sequence in which X in SEQ ID NO: 1 is Val, Ala, and Gly in a 1:8:7 ratio (SEQ ID NO: 2); Gly (SEQ ID NO: 3); Val, Ala, and Gly in a 1:4:3 ratio (SEQ ID NO: 4); or a combination thereof.

Additionally, non-limiting examples of the kidney targeting agents include a kidney targeting peptide (SEQ ID NO: 5), a kidney targeting peptide (SEQ ID NO: 6), a Tat peptide (SEQ ID NO: 7), a SynB1 peptide (SEQ ID NO: 8), or a combination thereof.

Moreover, non-limiting examples of the drug binding domain includes repeats of the sequence GGC (SEQ ID NO: 9), the sequence GC (SEQ ID NO: 10), the sequence GGK (SEQ ID NO: 11), and the sequence GK (SEQ ID NO: 12).

Further provided in some embodiments of the presently disclosed subject matter, is a therapeutic agent including at least one growth factor. In some embodiments, the growth factor includes VEGF, HGF, b-FGF, TGF-β, and HIF. In some embodiments, the therapeutic agent includes a VEGF selected from $VEGF_{121}$, $VEGF_{165}$, $VEGF_{189}$, $VEGF_{206}$, VEGF-A, VEGF-B, VEGF-C, VEGF-D, VEGF-E, and P1GF.

The term "pharmaceutically acceptable carrier" refers to sterile aqueous or nonaqueous solutions, dispersions, suspensions or emulsions, as well as sterile powders for reconstitution into sterile solutions or dispersions just prior to use. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Depending upon the ratio of drug to polymer and the nature of the particular polymer employed, the rate of drug release can be controlled. The formulations can be sterilized, for example, by filtration through a bacterial-retaining filter or by incorporating sterilizing agents in the form of sterile solid compositions which can be dissolved or dispersed in sterile water or other sterile injectable media just prior to use.

In addition to targeting specific regions of the kidney, the ELPs disclosed herein provide many advantages for production and purification. For example, ELPs are genetically encoded rather than chemically synthesized, ELP and ELP-fusion proteins can be expressed in *E. coli* and other eukaryotic expression systems allowing large quantities of the molecules to be purified easily because the polypeptide is thermally responsive. Purification of ELP-fusion proteins is achieved by heating a bacterial lysate containing the recombinantly expressed ELP above the polypeptides' transition temperature. This induces ELP aggregation, and it is collected by centrifugation. Repeated centrifugation above and below the transition temperature leads to large quantities of very pure protein. Furthermore, ELPs are large, non-immunogenic macromolecules. Therefore, ELP fusion can stabilize small protein or peptide or small molecule therapeutic agent cargo in systemic circulation, and targeting agents can be used to direct the ELP-fused therapeutics' biodistribution.

Further, in some embodiments, the presently-disclosed subject matter provides a method of delivering a therapeutic agent to a subject in need thereof. The method includes administering to the subject an effective amount of a composition. The composition includes an elastin-like polypeptide (ELP), a kidney targeting agent coupled to the ELP, and a therapeutic agent and/or a drug binding domain coupled to the ELP. In some embodiments, the ELP includes an amino acid sequence having at least about 5 repeats of SEQ ID NO: 1, and the composition enhances the deposition and retention of the therapeutic agent in the kidney relative to the non-conjugated therapeutic. In some embodiments, the ELP includes an amino acid sequence comprising about 5 repeats to about 320 repeats of SEQ ID NO: 1, and X in SEQ ID NO: 1 is any amino acid except proline. In some embodiments, the X in SEQ ID NO: 1 is Val, Ala, and Gly in a ratio range of about 0-1:0-8:0-8. In some embodiments, the ELP includes SEQ ID NO: 1, and X is Val, Ala, and Gly in a 1:8:7 ratio (SEQ ID NO: 2) repeated between 5 and 320 times. In some embodiments, the ELP comprises SEQ ID NO: 1, and wherein X is Gly (SEQ ID NO: 3) repeated between 5 and 320 times. In some embodiments, the ELP comprises SEQ ID NO: 1, and X is Val, Ala, and Gly in a 1:4:3 ratio (SEQ ID NO: 4) repeated between 5 and 320 times.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts.

Further provided, in some embodiments of the presently disclosed subject matter, is a targeting agent that is used to increase kidney deposition and specificity. The incorporation of the targeting agent increases kidney deposition and specificity of the delivered therapeutic agent and/or a drug binding domain. In some embodiments, the kidney targeting agent is a kidney targeting peptide having SEQ ID NO: 5. In some embodiments, the kidney targeting agent is a peptide having SEQ ID NO: 6. In some embodiments, the kidney targeting agent is a Tat peptide having SEQ ID NO: 7. In some embodiments, the kidney targeting agent is a SynB1 peptide having SEQ ID NO: 8. In some embodiments, non-limiting examples of the drug binding domain includes repeats of the sequence GGC (SEQ ID NO: 9), repeats of the sequence GC (SEQ ID NO: 10), repeats of the sequence GGK (SEQ ID NO: 11), and repeats of the sequence GK (SEQ ID NO: 12). In some embodiments, the therapeutic agent includes at least one growth factor selected from the group consisting of VEGF, HGF, b-FGF, TGF-β, and HIF. Non-limiting examples of VEGF include $VEGF_{121}$, $VEGF_{165}$, $VEGF_{189}$, $VEGF_{206}$, VEGF-A, VEGF-B, VEGF-C, VEGF-D, VEGF-E, and P1GF. In some embodiments, the composition is administered intrarenally, intravenously, intraperitoneally, orally, intranasally, or subcutaneously.

In this regard, the term "administer" refers to any method of providing a compound or composition thereof to a subject. In some embodiments, suitable methods for administering a therapeutic composition in accordance with the methods of the presently-disclosed subject matter may include, but are not limited to, intra-renal administration, intravenous administration, intraperitoneal administration, oral administration, intranasal administration, subcutaneous administration, systemic administration, parenteral administration (including intravascular, intramuscular, and/or intraarterial administration), buccal delivery, rectal delivery, inhalation, intratracheal installation, surgical implantation, transdermal delivery, local injection, and hyper-velocity injection/bombardment.

Further provided, in some embodiments of the presently-disclosed subject matter are methods for the treatment of various diseases and disorders using the exemplary ELP-therapeutic agent-containing compositions described herein. In some embodiments, the presently-disclosed subject matter includes a method of treating a kidney disease or disorder in a subject wherein the subject is administered an effective amount of a composition comprising an ELP coupled to a kidney targeting agent and a therapeutic agent and/or a drug binding protein. In some embodiments, the ELP includes an amino acid sequence having at least about 5 repeats of SEQ ID NO: 1, and the composition enhances the deposition and retention of the therapeutic agent in the kidney relative to the non-conjugated therapeutic. Exemplary diseases or disorders that can be treated in accordance with the presently-disclosed subject matter include, but are not limited to, Chronic kidney disease (CKD), Chronic renal vascular disease (RVD), end-stage renal disease.

In some embodiments the method for administering the present compounds and compositions further include treating a disease or condition in the subject. The terms "treatment" or "treating" refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Furthermore, the term "subject" is inclusive of both human and animal subjects. Thus, veterinary uses are provided in accordance with the presently disclosed subject matter and the presently-disclosed subject matter provides methods for preventing oxidative damage in mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The presently-disclosed subject matter is further illustrated by the following specific but non-limiting examples. The following examples may include compilations of data that are representative of data gathered at various times during the course of development and experimentation related to the present invention.

EXAMPLES

Figure 1B:
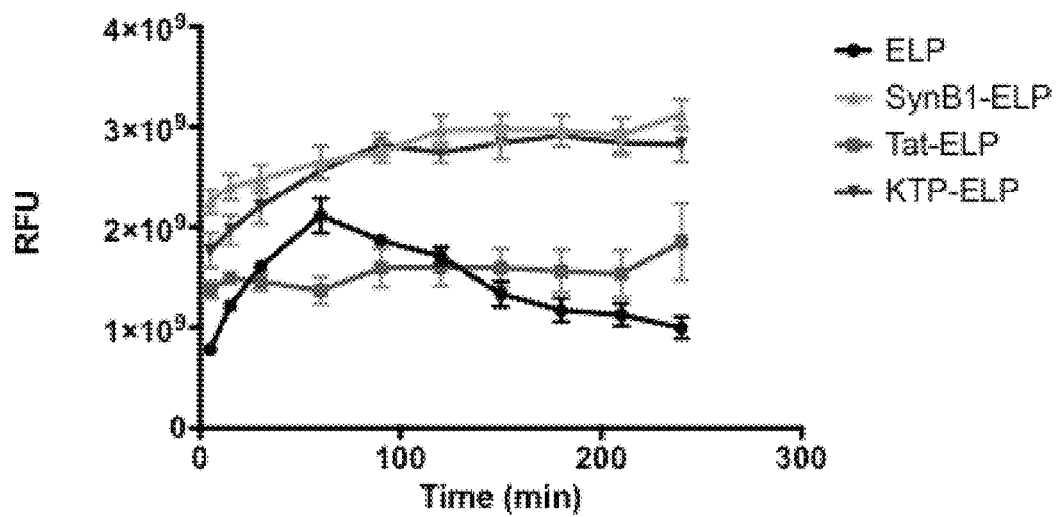

Example 1. Targeting Peptides Increase Total Renal Deposition and Enhance the Renal Specificity of ELP Biodistribution A biodistribution study was performed to determine whether increasing ELP levels in the kidneys using targeting peptides was possible. The ELP molecule was fused to one of two cell penetrating peptides (CPPs) (SynB1 and Tat [4, 5] or to a peptide found to have specificity for the kidney (Kidney Targeting Peptide, KTP [6]). Each polypeptide was labeled with a fluorophor and administered by IV injection at a dose of 100 mg/kg in hairless Sprague Dawley rats. The whole-body fluorescence of the animals throughout the experiment is measured by in vivo imaging. As shown in FIGS. 1A-B, when the untargeted ELP carrier was injected, the fluorescence spread throughout the body and reached a peak intensity approximately 1 hour after the injection, then the fluorescence level slowly decreased. In contrast, the SynB1-ELP and the KTP-ELP polypeptides achieved much higher levels throughout the body, and the levels were just beginning to peak four hours after the injection. These data reveal that the use of the targeting peptides increases extravasation and tissue uptake of the drug carrier and therefore slows its clearance from the body tissues.

The whole-body in vivo fluorescence provides a measurement of total tissue polypeptide levels, but it cannot resolve the individual organ biodistribution. In order to measure the biodistribution, the major organs were removed, and polypeptide levels were determined by quantitative whole organ ex vivo imaging four hours after the injection. As shown in FIGS. 2A-D, the unmodified ELP accumulated most highly in the kidney and the liver. When the ELP was modified with the cell penetrating peptides or the KTP, the kidney levels increased dramatically (over five-fold, FIG. 2B). Both cell penetrating peptides and the KTP achieved similar kidney levels. However, when kidney specificity was assessed by measuring the kidney:liver and the kidney:heart ratios, the KTP proved to be by far the most specific (FIGS. 2C-D). In fact, KTP-ELP accumulated in the kidneys at levels 15-fold higher than in the liver and as much as 150-fold higher than in other organs including the heart, brain, and spleen. These data demonstrate that KTP is an effective targeting agent for increasing both total renal accumulation and renal specificity of the ELP drug carrier, and they are the first demonstration of the use of targeting peptides to achieve kidney-specific delivery of the ELP carrier.

Figure 3A:
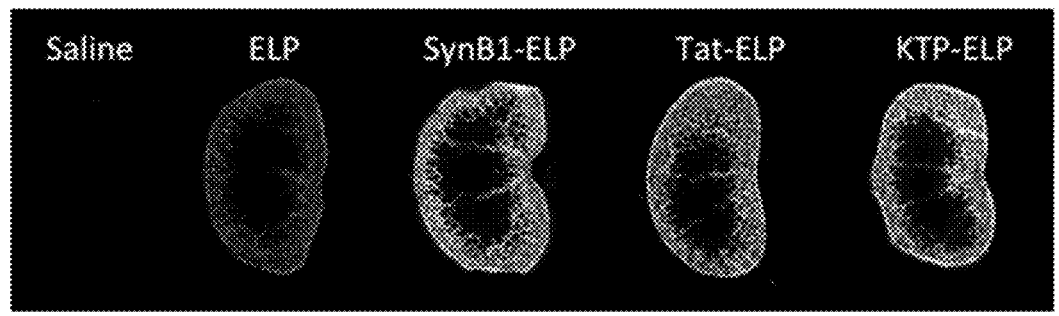
FIGS. 3A-B include a series of slide scans and micrographs depicting the intrarenal distribution of renally targeted ELPs. Four hours after intravenous infusion of fluorescently labeled ELP, SynB1-ELP, Tat-ELP, or KTP-ELP, the kidneys were rapidly frozen and cut into 20 μm sections. (A) Slides were scanned using a fluorescence slide scanner. Identical scan settings were used in order to directly compare the total kidney levels. (B) Slides were stained with several vascular markers and imaged using a fluorescence microscope and 20× objective. Shown is the intrarenal distribution of KTP-ELP. Tat-ELP and SynB1-ELP had similar intrarenal distribution (not shown).
Figure 3B:
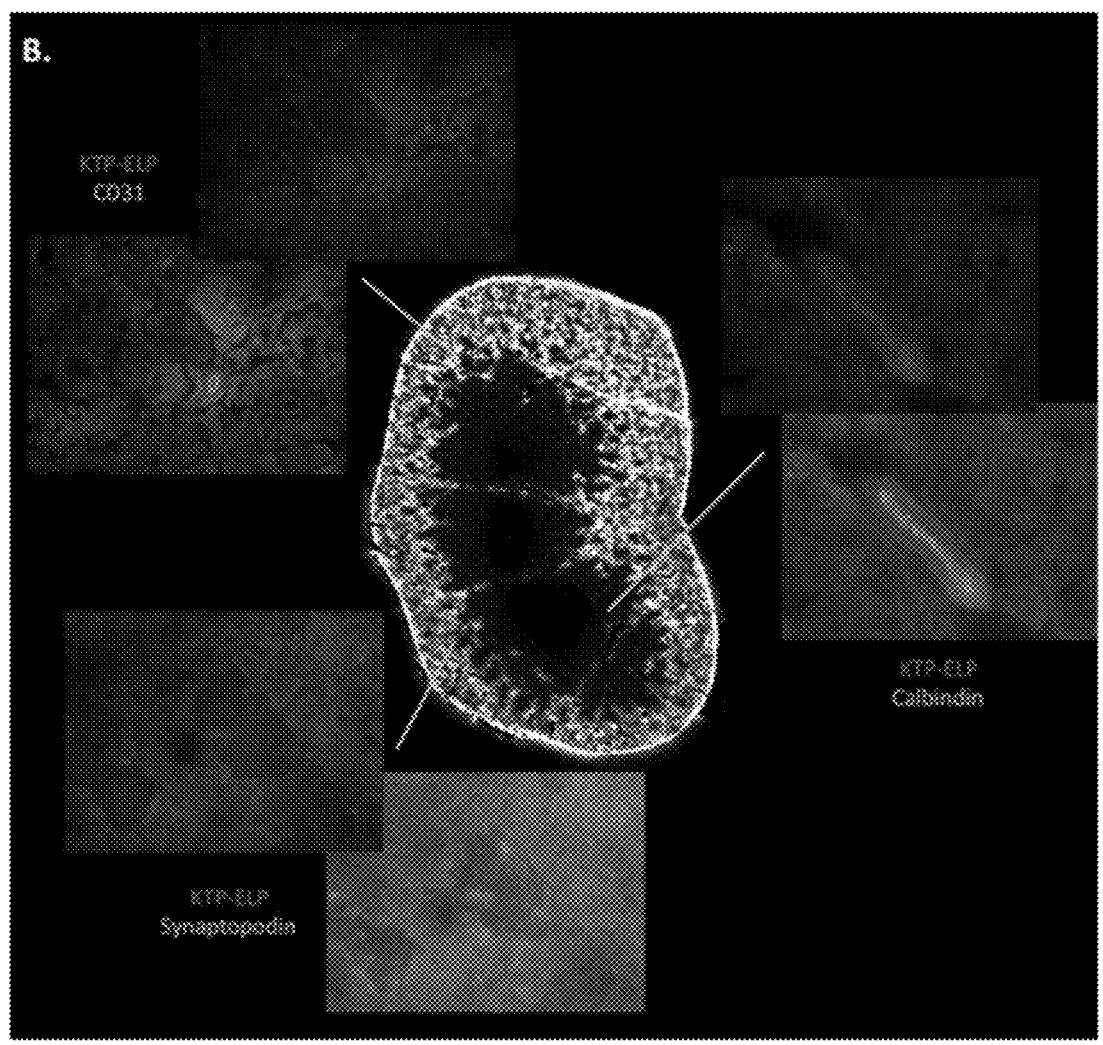

In addition to the whole-organ ex vivo imaging, the kidneys were frozen and sectioned to determine the intrarenal distribution of the polypeptides. Fluorescence slide scanning revealed that all polypeptides were mostly confined to the renal cortex (FIG. 3A). Also, consistent with the whole-organ imaging, SynB1-ELP, Tat-ELP, and KTP-ELP accumulated to very high levels relative to the untargeted ELP biopolymer. When examined microscopically (FIG. 3B), KTP-ELP was localized around the nephron (marked by synaptopodin staining) and was detectable in both the blood vessel walls (as indicated by CD31 staining) and in the surrounding proximal and distal tubules. Images taken in the outer medulla and co-stained with calbindin to mark the collecting ducts also showed high levels of KTP-ELP within the ductal epithelial cells. SynB1-ELP and Tat-ELP had very similar intrarenal distributions (data not shown).

Figure 4A:
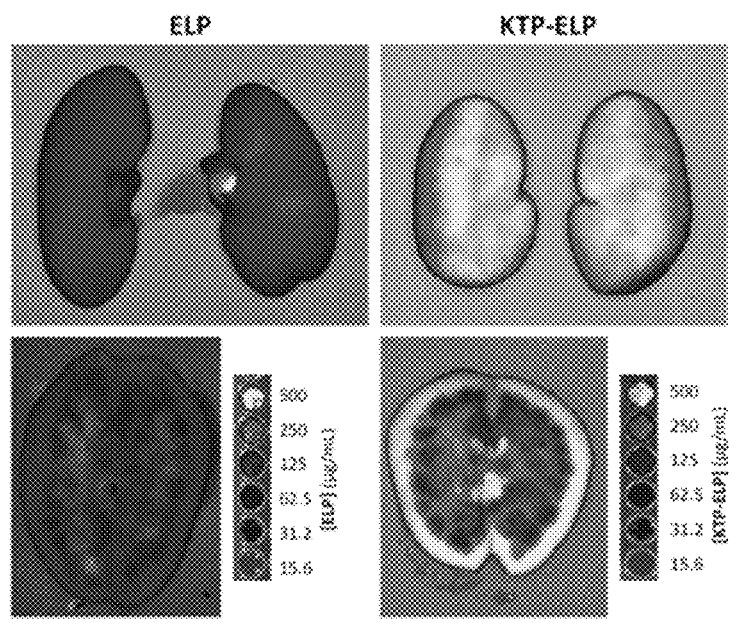
FIGS. 4A-B include fluorescence photographs and a bar graph showing that KTP enhances ELP deposition in the swine kidney after IV administration. Pigs (n=3 per agent) were given fluorescently labeled ELP or KTP-ELP by intravenous injection. Organ distribution was determined 4 h after injection by (A) ex vivo whole organ fluorescence imaging and (B) quantified relative to standard curves of each agent.
Figure 4B:
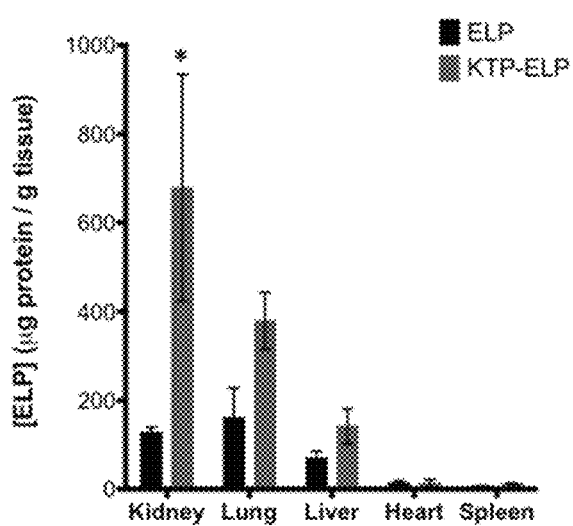

To insure that the ability of KTP to target ELP to the kidneys was not specific to rats, a similar experiment was conducted in swine. Domestic crossbred female pre-juvenile pigs (*Sus scrofa domestica*) were adminstered ELP or KTP-ELP (n=3 pigs/agent) by IV injection. Ex vivo quantitative fluorescence histology was performed as described above. As shown in FIGS. 4A-B, KTP-ELP accumulated in the swine kidney at levels 5.4 fold higher than the untargeted ELP, and kidney KTP-ELP levels were 4.8-fold higher than liver, almost two-fold higher than lung, and over 50-fold higher than heart and spleen. These data demonstrate that KTP is effective for kidney targeting in a predictive pre-clinical model and is not species specific.

Figure 5A:
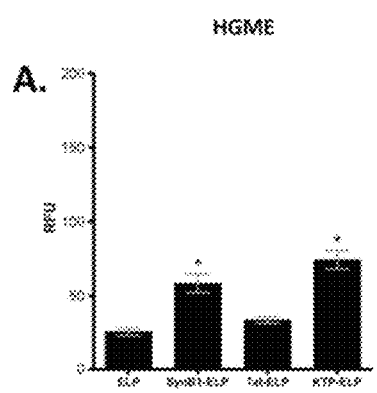
FIGS. 5A-F include a series of bar graphs demonstrating that KTP-ELP enhances ELP binding to human renal cells. (A-C) Cell binding and (D-F) cell survival of SynB1-ELP, Tat-ELP, and KTP-ELP relative to ELP control were determined by flow cytometry and a cell viability assay, respectively, in (A,D) primary human glomerular microvascular endothelial cells, (B,E) primary human podocytes, and (C,F) primary human proximal tubule epithelial cells.
Figure 5B:
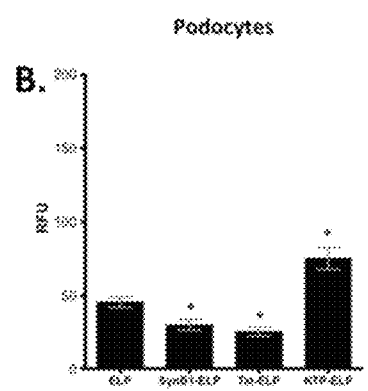
Figure 5C:
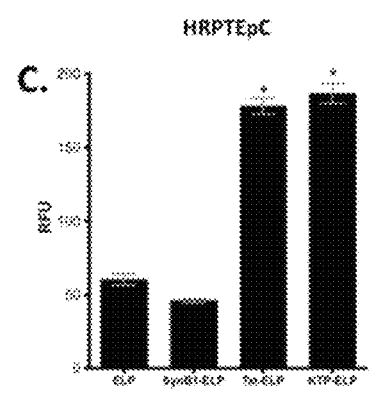
Figure 5D:
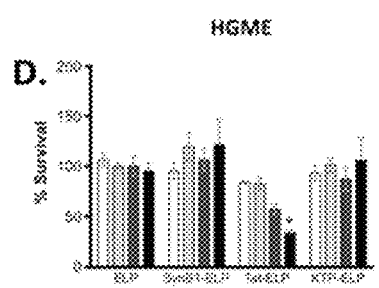
Figure 5E:
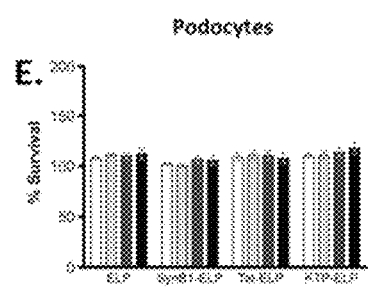
Figure 5F:
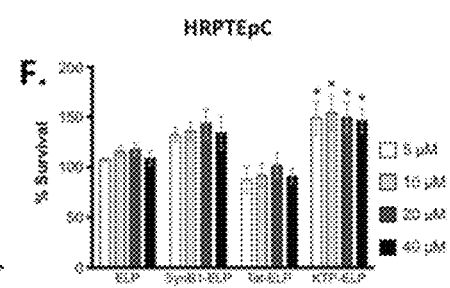

We also sought to determine if KTP could enhance ELP binding to primary human renal cells and to identify which cell type KTP has affinity for. Primary human glomerular microvascular endothelial cells (HGME), primary human podocytes, and primary human renal proximal tubule epithelial cells (HRPTEpC) were cultured in vitro and exposed to 10 μM ELP or KTP-ELP. Cells were also exposed to the cell penetrating peptide—fused ELPs SynB1-ELP and Tat-ELP as comparators. As shown in FIGS. 5A-C, KTP enhanced ELP binding to all renal cell types. Binding was increased 3 fold in HGME (FIG. 5A), 1.7 fold in podocytes (FIG. 5B), and 3 fold in HRPTEpC (FIG. 5C) by KTP-ELP relative to ELP control. This was in contrast to the CPP-fused ELPs. Tat only enhanced ELP binding to HRPTEpC (FIG. 5C) and actually reduced binding to podocytes (FIG. 5B). SynB1 only enhanced ELP binding to HGME cells (FIG. 5A) and also reduced binding to podocytes (FIG. 5B). We also tested whether KTP-ELP had any toxicity to the human cell lines (FIGS. 5D-F). Each cell line was incubated with ELP, SynB1-ELP, Tat-ELP, or KTP-ELP at concentrations up to 40 µM for 72 h, and cell number was determined using the MTS assay. KTP showed no toxicity to any cell line tested, and it even stimulated proliferation of HRPTEpC (FIG. 5F). In contrast, Tat-ELP was toxic HGME cells (FIG. 5D). SynB1-ELP showed no cytotoxicity. These data demonstrate that KTP has affinity for several renal cell lines, and, in contrast to CPPs, it increases ELP binding to all renal cell types tested.

Example 2. ELP-Fused Vascular Endothelial Growth Factor (VEGF) Deposits in the Kidney and Improves Renal Function in a Swine Model of Renovascular Disease Chronic kidney disease (CKD) is a progressive disorder affecting almost 14% of the general population, and the prevalence of this disease has continuously grown over the past 2 decades [7]. CKD is an independent risk factor for cardiovascular morbidity and mortality, as patients with diagnosed cardiovascular disease show a staggering 40.8% prevalence of CKD, a number that has doubled in less than 20 years [7]. Patients with CKD have higher rates of hospitalization, greater mortality, shorter life expectancy, and their healthcare costs are up to 5 times more expensive than non-CKD patients, which represent an enormous burden to the healthcare budget. Thus, treatments to slow, halt, or reverse the progression of CKD could have a significant impact.

Chronic RVD can deteriorate renal function and lead to CKD and end-stage renal disease. It affects between 9-11% of the general population, but this number goes up in patients with diagnosed coronary artery or peripheral vascular disease (about 30%), and are much higher in older patients (up to 60% in patients >65 years) [8-10]. The main cause of RVD is renal artery stenosis, often due to atherosclerosis. Although the vascular obstruction is the initial and possibly main instigator of renal injury, therapeutic strategies that aim to resolve the vascular stenosis such as renal angioplasty and stenting are effective in recovering renal function in less than half of the cases. The disparity between technical success and outcomes has served as the impetus for numerous trials to assess the efficacy of medical therapy vs. interventions in this disease, focusing in two major end points: reduction of hypertension and recovery of renal function. Nevertheless, the outcomes of RVD are still poor. Although numerous trials have been critiqued because of flaws in design and follow up, the results weighed more towards the conclusion that there are no major benefits achieved by renal angioplasty compared to medical treatment that would justify the risk of revascularization procedures [11]. Consequently, there is a noticeable lack of consensus regarding the best therapeutic strategy for these patients. Hence, more effective treatments are needed and the technology described within represents a new therapeutic strategy that has not been previously tested for renal therapy.

Damage of the small vessels in the kidney is a common pathological feature in CKD and end stage renal disease irrespective of the cause. Furthermore, major cardiovascular factors and causes of CKD such as hypertension or diabetes have been shown to associate with intra-renal microvascular (MV) rarefaction that is observed before deterioration of renal function. These support the notion of a potential cause-effect relationship and suggest a pathophysiological role of MV damage on the progression of renal dysfunction. Over the past 14 years, a unique swine model of RVD was developed that mimics the progressive nature of renal injury, hypertension, and cardiovascular risk found in humans with RVD. Moreover, physiological imaging techniques were developed and validated using high-resolution computerized tomography (CT) to measure renal regional volumes, total renal blood flow (RBF), glomerular filtration rate (GFR), tubular dynamics, and endothelial function; and micro-CT to study the 3D architecture of the renal microcirculation in situ. These techniques allow us to non-invasively and serially follow the time course of the deterioration of the kidney in an integrative fashion and with previously unavailable accuracy. Progressive loss of renal function and tissue damage in RVD is accompanied by marked and progressive renal microvascular damage and loss in the stenotic kidney (evident in both renal cortex and medulla), which is mediated by a progressive decrease in renal expression and availability of VEGF and a defective renal angiogenesis and vascular repair [12-15].

Figure 6:
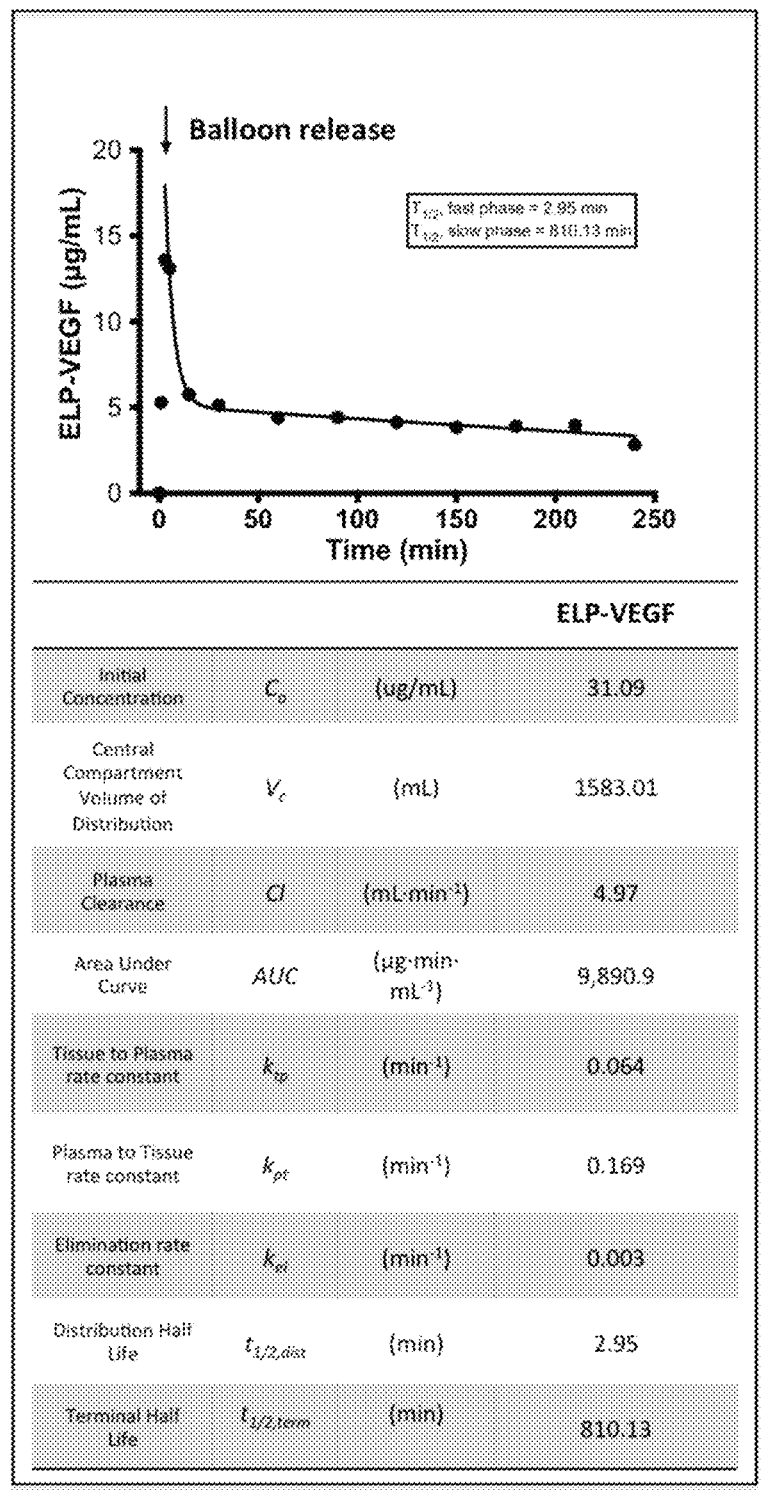
FIG. 6 contains a scatter plot and tabular data depicting the pharmacokinetics of intrarenal ELP-VEGF in the Pig. Three pigs (average weight 49.2 kg) were given fluorescently labeled ELP-VEGF by direct intrarenal administration. A balloon was inflated to block blood flow into and out of the injected kidney for three minutes. The balloon was released, and plasma was sampled to determine ELP-VEGF levels. Plasma levels were determined by direct detection of fluorescence and fit to a two compartment pharmacokinetic model.
Figure 7A:
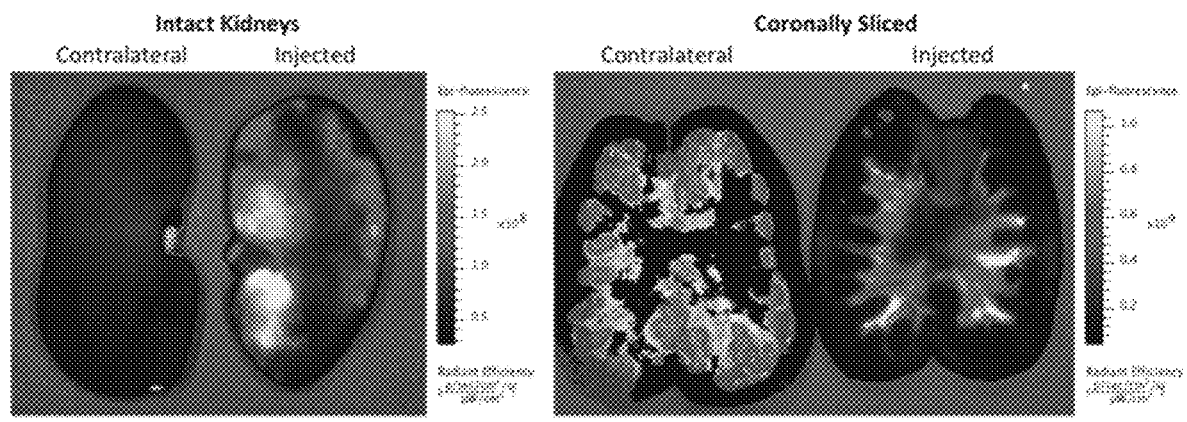
FIGS. 7A-B include a series of images and a graph depicting the biodistribution of intrarenal ELP-VEGF in the Pig. Three pigs were given fluorescently labeled ELP-VEGF by direct intrarenal administration. (A-B) Organ distribution was determined 4 h after injection by ex vivo whole organ fluorescence imaging.
Figure 7B:
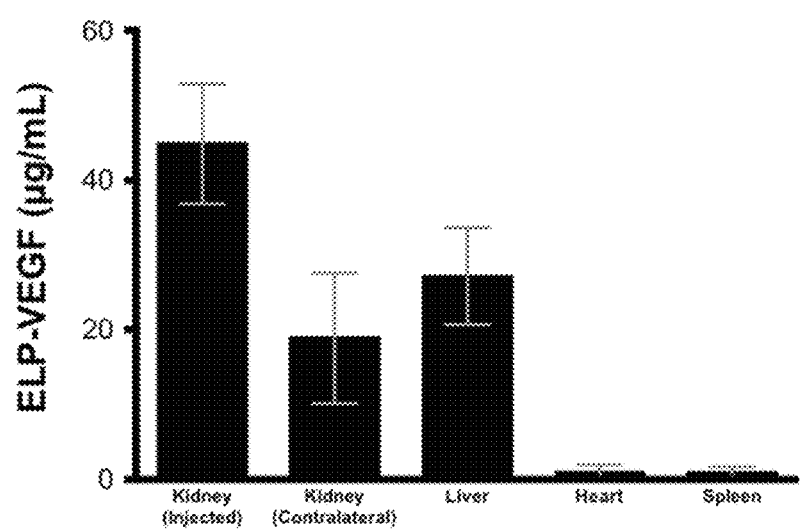

ELP-VEGF is retained in the kidney after intrarenal administration in the pig. To determine if the ELP-delivered VEGF could be retained in the kidney in the swine RVD model, a biodistribution study in the pig was conducted. Three pigs (average weight 49.2 kg) were administered fluorescently labeled ELP-VEGF by direct intrarenal injection under fluoroscopy guidance. A balloon catheter was inflated for three minutes following the injection, then the balloon was deflated to allow blood to circulate through the kidney. Blood was sampled from the jugular vein at fixed time-points, and plasma fluorescence measurements were taken to monitor ELP-VEGF levels. The distribution phase half-life was 2.95 minutes and the terminal plasma half-life was 810.1 minutes (FIG. 6). Four hours after injection, the pigs were sacrificed and the organs analyzed by ex vivo fluorescence imaging. As shown in FIGS. 7A-B, the injected kidney retained the ELP-VEGF, showing tissue levels nearly three fold higher than the contralateral kidney or any other organ. Some protein did enter systemic circulation, as evidenced by its detection in the contralateral kidney and liver. However, these results demonstrate that intrarenal administration is a viable route for delivery of ELP-VEGF, and kidney levels will be increased further when the ELP-VEGF is fused to the KTP.

ELP-VEGF is equally as active as free VEGF in primary human glomerular microvascular endothelial (HGME) cells. Primary Human Glomerular Microvascular Endothelial (HGME) cells were used to insure the signaling properties of VEGF were retained even after fusion to the ELP carrier. As shown in FIG. 8A, both unbound VEGF and ELP-VEGF stimulated proliferation of HGME cells, while the ELP polypeptide alone had no effect on HGME proliferation. Furthermore, no significant differences were seen in the potency of the unbound cytokine and the ELP-fused VEGF, suggesting that the ELP-fused VEGF is still able to bind its receptor. To test this further, HGME cells were used in to a tube formation assay on growth factor reduced Matrigel. As shown in FIG. 8B, very little tube formation was observed on this matrix without additional stimulation. However, when the media was supplemented with unbound VEGF or ELP-VEGF, tube formation was significantly induced. Quantification of tubes per visual field showed that both unbound VEGF and ELP-VEGF significantly induced tube formation relative to untreated cells (FIG. 8C). There were also more average tubes per field in the ELP control-treated samples, though the difference did not reach statistical significance. Finally, to assess the ability of ELP-VEGF to serve as a chemokine for HGME cells, a Matrigel migration assay was used. As shown in FIG. 8D and quantified in FIG. 8E, both unbound VEGF and ELP-VEGF strongly induced HGME cell migration through Matrigel, while the control ELP had no effect. Again, there was no difference in potency between VEGF and ELP-VEGF.

Figure 9A:
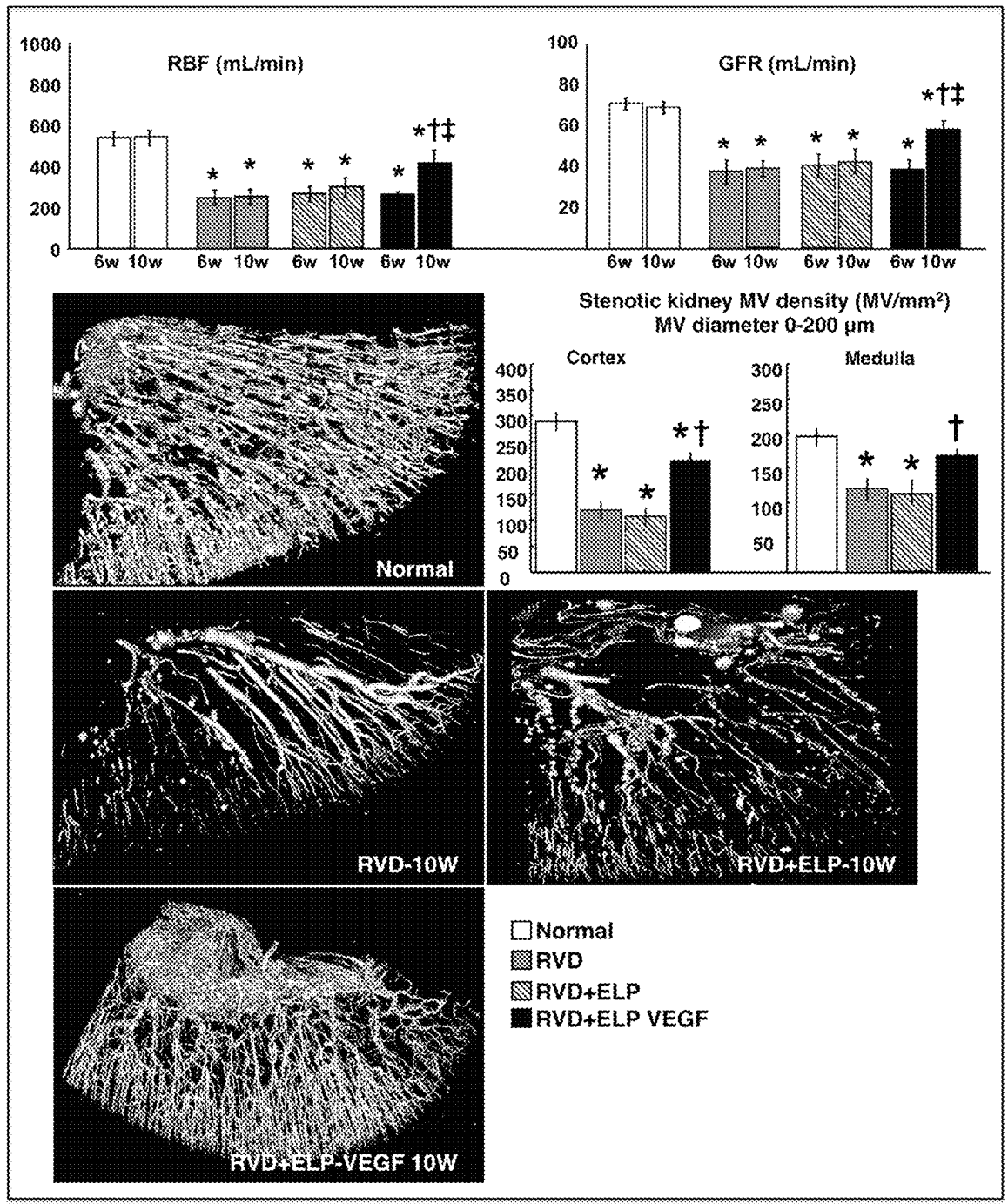
FIGS. 9A-B include a series of graphs and images demonstrating the effect of intrarenal ELP-VEGF on renal function in RVD. (A) shows that intra-renal administration of ELP-VEGF improved renal function, cortical and medullary vascular density in the stenotic kidney. Effect of intra-renal ELP-VEGF on renal function (top) and microvascular (MV) architecture (3D micro-CT reconstruction, bottom) and quantification in normal, renovascular disease (RVD), RVD+ELP, and RVD+ELP-VEGF treated kidneys. *$p<0.05$ vs. Normal; †$p<0.05$ vs. RVD/RVD+ELP; ‡$p<0.05$ vs. 6 weeks. (B) shows that intra-renal administration of ELP-VEGF improved the vascular density of both small and larger MV diameters in the cortex and medulla of the stenotic kidney. Cortical and medullary quantification of microvascular (MV) density divided by MV diameter in normal, renovascular disease (RVD), and RVD+ELP-VEGF treated kidneys. *$p<0.05$ vs. Normal; †$<0.05$ vs. RVD.
Figure 9B:
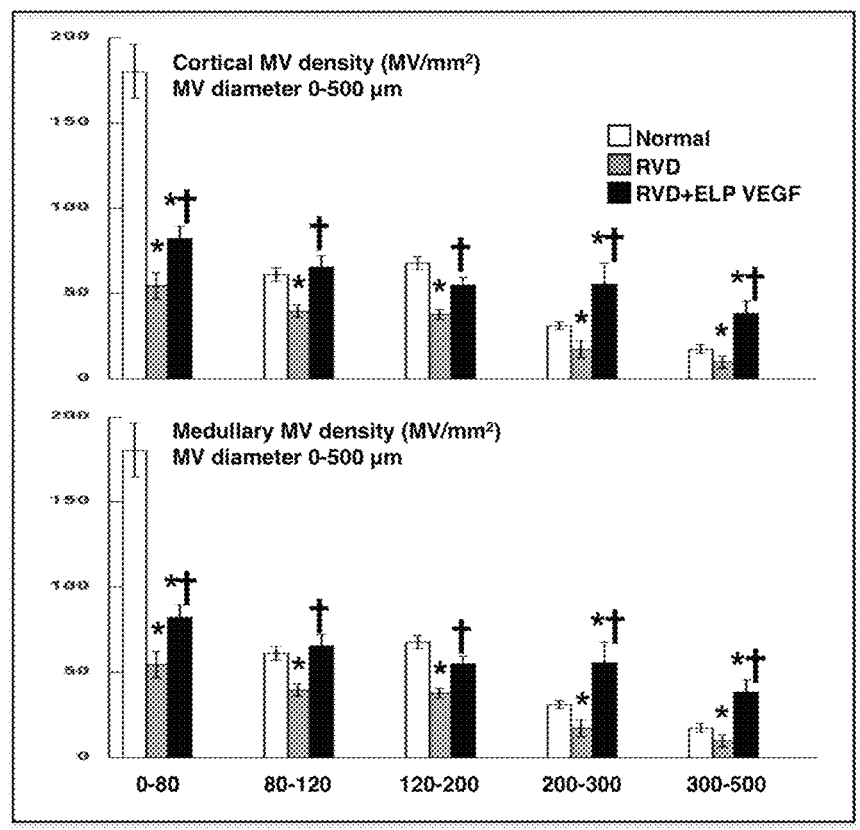

Single-dose intra-renal ELP-VEGF causes improvement in renal function in a swine model of chronic RVD. To determine whether administration of ELP-VEGF into the stenotic kidney has an impact on renal function and microvascular architecture, 7 pigs were treated after 6 weeks of RVD with a single infusion of ELP-VEGF (100 µg/kg). An additional 7 pigs with RVD received placebo and were used as controls. Single-kidney function was quantified in vivo in all pigs before and 4 weeks after treatments/placebo. Pigs were observed for a total of 10 weeks and then euthanized. Kidneys were then removed and micro CT studies (to quantify the impact of ELP/placebo on the renal microvasculature) and protein expression studies performed. It was observed that administration of ELP-VEGF significantly improved renal function compared to placebo (FIG. 9A, top). The improvement was specific to ELP-VEGF, as the ELP control polypeptide had no effect on renal function. The stenotic kidney showed a significant reduction in cortical and medullary microvascular density accompanied by substantial microvascular remodeling compared to normal controls (FIG. 9A, bottom). Notably, intra-renal ELP-VEGF significantly improved both cortical and medullary microvascular density and remodeling of small and large microvessels (0-500 µm in diameter), which was evident throughout the renal parenchyma (FIG. 9B).

ELP-VEGF is more effective than unconjugated VEGF for improvement of renal function. A single intra-renal administration of free $VEGF_{121}$ significantly improved stenotic RBF but not GFR (p<0.05 and p=NS, respectively, vs. pre-treatment values) and the magnitude of those changes was significantly less compared to ELP-VEGF therapy (FIG. 10A). Furthermore, intra-stenotic kidney infusion of acetylcholine (quantified at 10 weeks) improved RBF but not GFR in free VEGF treated kidneys whereas both RBF and GFR were improved in after ELP-VEGF (FIG. 10B). Finally, free VEGF therapy improved MV density only in those cortical microvessels under 200 µm in diameter and not in larger microvessels (200-500 µm in diameter, FIG. 10C). Overall, these findings strongly support a superior efficacy of ELP-VEGF therapy over unconjugated VEGF.

Figure 11:
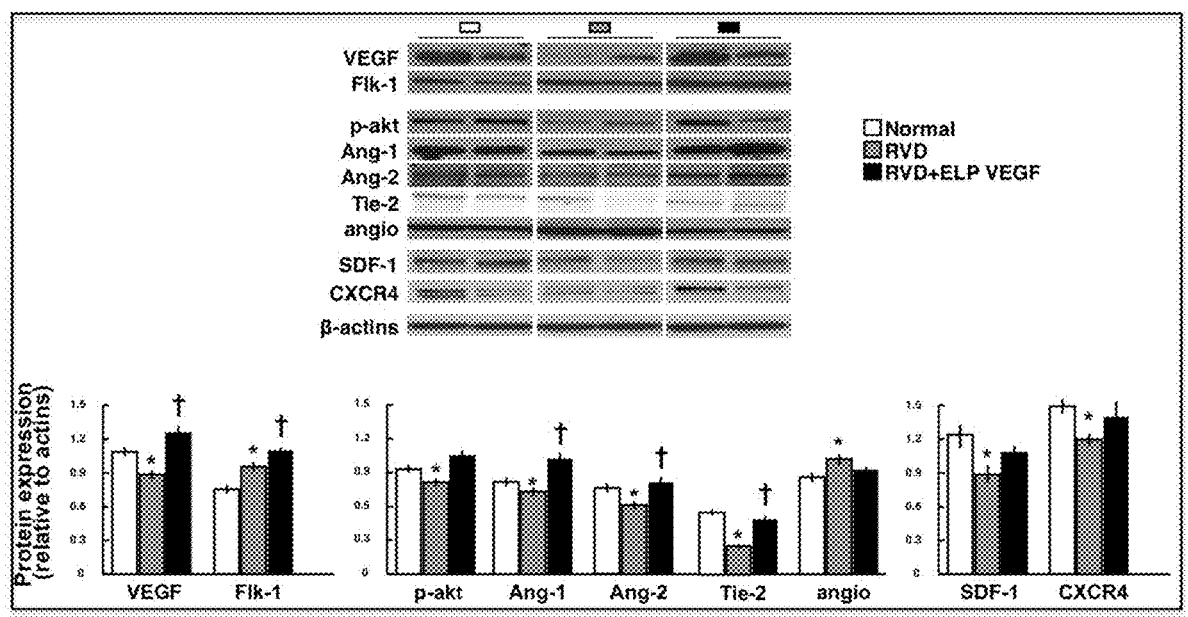
FIG. 11 includes Western blot data and bar graphs demonstrating that Intra-renal administration of ELP-VEGF improved the expression of angiogenic factors and promoters of mobilization and homing of progenitor cells in the stenotic kidney. Representative renal protein expression (top, 2 bands per group) of vascular endothelial growth factor (VEGF), its receptor Flk-1, phosphorylated (p)-akt, angiopoietin (Ang)-1 and -2, Tie-, angiostatin (angio), stromal-derived factor (SDF)-1 and its receptor CXCR4, and quantification (bottom) in normal, renovascular disease (RVD), and RVD+ELP-VEGF treated kidneys. *$p<0.05$ vs. Normal; †$p<0.05$ vs. RVD.

ELP-VEGF activates VEGF signaling in the stenotic kidney. Kidneys from the efficacy study were examined by Western blot to confirm activation of VEGF signaling at the experimental endpoint. Expression of VEGF, the receptor Flk-1, angiopoietin (Ang)-1 and -2 and the Tie-2 receptor were significantly reduced in RVD but largely restored and accompanied by improved expression of phosphorylated (p)-akt, stromal-derived factor (SDF)-1 and the CXCR4 receptor, and attenuated expression of anti-angiogenic angiostatin (angio) after ELP-VEGF therapy, suggesting a pro-angiogenic milieu in the stenotic kidney of ELP-VEGF treated pigs (FIG. 11).

Figure 12A:
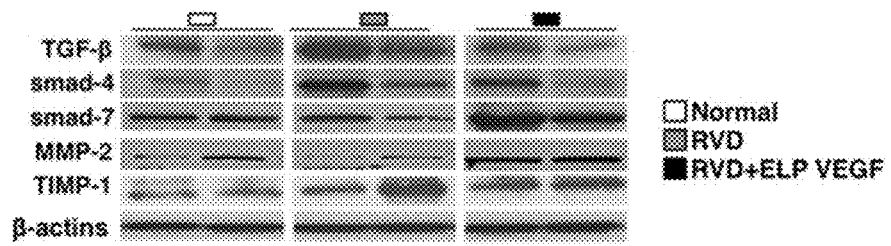
FIGS. 12A-C include Western blot and histological data showing that intra-renal administration of ELP-VEGF reduced renal fibrogenic activity and attenuated podocyte damage and fibrosis in the stenotic kidney. (A) Representative renal protein expression (2 bands per group) and (B) quantification of transforming growth factor (TGF)-β, smads-4-7, matrix metalloproteinases (MMP)-2 and its inhibitor TIMP-1 in normal, renovascular disease (RVD), and RVD+ELP-VEGF treated kidneys. (C) Top: representative pictures (from stenotic kidneys) of the glomeruli (x40), showed as examples to illustrate podocin immunoreactivity (black arrows); Bottom: representative trichrome pictures (from stenotic kidneys) of the glomeruli and tubules, and tubule-interstitial regions (×20, showed as examples to illustrate renal damage). * $p<0.05$ vs. Normal; †$p<0.05$ vs. RVD.
Figure 12B:
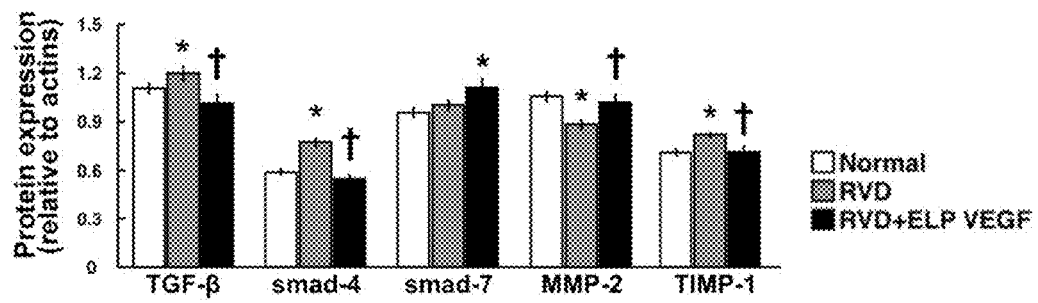
Figure 12C:
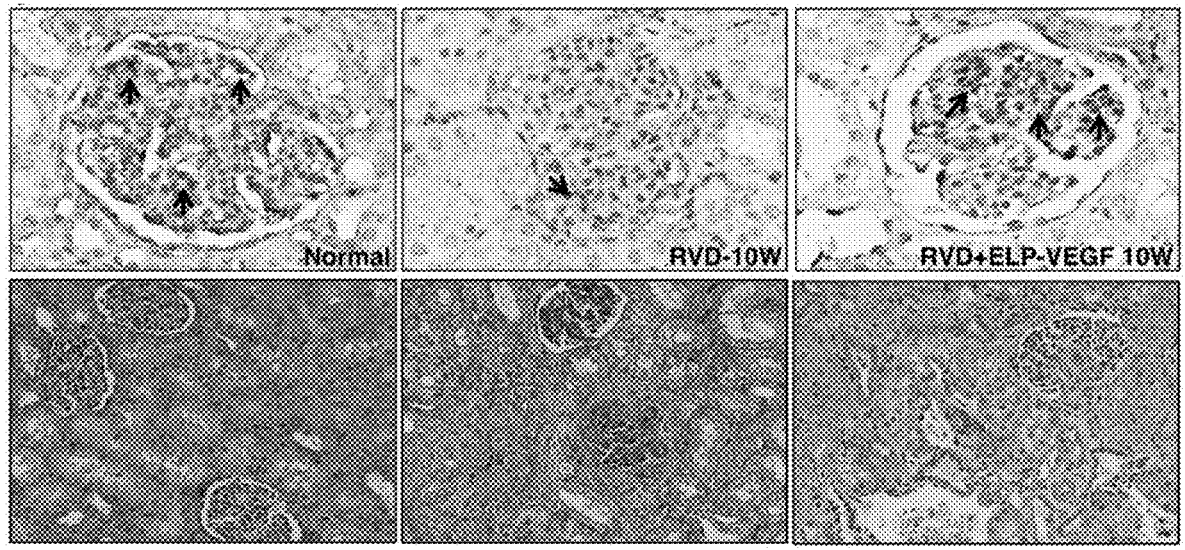

ELP-VEGF reduces inflammatory activity and fibrotic damage in the stenotic kidney. ELP-VEGF therapy decreased the renal concentration of tumor necrosis factor (TNF)-α (Untreated pigs 9.8±1.4 pg/mg tissue; RVD 19.4±0.6 pg/mg tissue; RVD+ELP-VEGF 13.4±3.2 pg/mg tissue, p<0.05), and attenuated the expression of pro-fibrotic transforming growth factor (TGF)-(β, smad-4, and tissue inhibitor of matrix-metalloproteinase (TIMP)-1, whereas improved smad-7 and matrix-metalloproteinase (MMP)-2 compared to untreated RVD, suggesting a potential decrease in pro-inflammatory, pro-fibrotic, and tissue remodeling activity (FIGS. 12A-B). Furthermore, ELP-VEGF therapy improved glomerular expression of podocin (FIG. 12C, top) and reduced nephrinuria, suggesting protection of podocytes. Glomerulosclerosis and tubule-interstitial fibrosis (7.3±0.01 and 9.3±0.04%, respectively, p<0.05 vs. Normal) were significantly reduced (2.3±0.04 and 3.4±0.1%, respectively, p<0.05 vs. RVD and Normal) after ELP-VEGF therapy (FIG. 12C, bottom). Similarly, MV media-to-lumen ratio (0.34±0.01, p<0.05 vs. Normal) was improved after ELP-VEGF therapy (0.18±0.005, p<0.05 vs. RVD, p=NS vs. Normal), suggesting attenuated MV remodeling in addition to the improvements in MV rarefaction.

This study supports the feasibility of ELP-VEGF therapy and suggests therapeutic effects of this intervention.

Figures 13A, 13B:
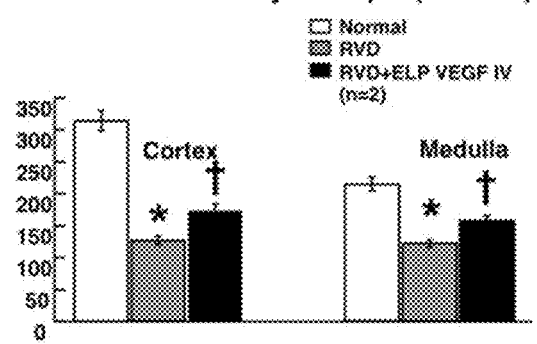
FIGS. 13A-B include an image and a graph showing the effect of IV ELP-VEGF on renal function in RVD. (A) Change in RBF and GFR after IV ELP-VEGF. (B) Micro-CT quantification of renal MV density after IV ELP-VEGF. Intra-venous ELP-VEGF improved renal function and MV density of the stenotic kidney. *$p<0.05$ vs. Normal; †$p<0.05$ vs. RVD.

Single-dose systemically-delivered ELP-VEGF improves renal function in a swine model of chronic RVD. Since ELPs have high affinity for renal tissue, preliminary studies were performed to determine whether a systemic administration may protect the kidney and improve renal function. To test this, 4 pigs with RVD were observed for 6 weeks, stenotic kidney function quantified, and then 2 of them treated with an intra-venous (IV) injection of ELP-VEGF via an ear vein cannula. Animals were observed for 4 additional weeks, and renal function was re-evaluated, observing that RBF and GFR in the stenotic kidney of treated pigs were improved by over 70% compared to pre-treatment function, as cortical MV rarefaction diminished (FIGS. 13A-B). These data suggested renoprotective effects of ELP-VEGF even using a systemic route.

Examples 3-6

These Examples explore the specific application of ELPs to renal drug delivery, as well as a detailed characterization of how ELP chain length affects the protein's pharmacokinetics and biodistribution, which is critical information when developing ELPs as drug carriers for other disease and conditions applications.

Example 3. Production and Characterization of ELP Proteins with Varying Molecular Weights ELPs were designed with varying coding sequence sizes and denoted by the number of VPGxG (SEQ ID NO: 1) motif repeat units, ranging from 31 repeat units to 671 repeat units (Table 1).

TABLE 1

ELP constructs, their coding sequence size, and predicted protein MW.

| Protein | Number of VPGxG (SEQ ID NO: 1) repeats | Insert size (bp) | Number of amino acid residues | Predicted protein MW (kDa) |
|---|---|---|---|---|
| ELP-31 | 31 | 480 | 170 | 13.0977 |
| ELP-63 | 63 | 960 | 330 | 25.2475 |
| ELP-95 | 95 | 1440 | 490 | 37.3972 |

TABLE 1-continued

ELP constructs, their coding sequence size, and predicted protein MW.

| Protein | Number of VPGxG (SEQ ID NO: 1) repeats | Insert size (bp) | Number of amino acid residues | Predicted protein MW (kDa) |
|---|---|---|---|---|
| ELP-127 | 127 | 1920 | 650 | 49.5469 |
| ELP-159 | 159 | 2400 | 810 | 61.696 |
| ELP-191 | 191 | 2880 | 970 | 73.8463 |
| ELP-223 | 223 | 3360 | 1130 | 85.996 |
| ELP-255 | 255 | 3840 | 1290 | 98.1457 |
| ELP-287 | 287 | 4320 | 1450 | 110.2955 |
| ELP-351 | 351 | 5280 | 1770 | 122.4452 |
| ELP-415 | 415 | 6240 | 2090 | 158.8943 |
| ELP-479 | 479 | 7200 | 2410 | 183.1937 |
| ELP-543 | 543 | 8160 | 2730 | 207.4932 |
| ELP-671 | 671 | 10080 | 3370 | 256.092 |

A library of ELP DNA constructs were generated in which the ratio of amino acids at the X position in the V-P-G-X-G (SEQ ID NO: 1) repeat is V:G:A in a 1:4:3 ratio. All ELP constructs are composed of pentapeptide repeats (SEQ ID NO: 1), denoted ELP-n, where n is the number of pentamer repeats. DNA encoding the ELP-31 sequence in a p-MA-RQ plasmid was custom synthesized (Life Technologies), and all subsequent constructs were synthesized by recursive directional ligation. Each new ELP coding sequence was inserted into the Sfi/site of a pET25b+ expression vector encoding a short N-terminal sequence containing a cysteine residue and short C terminal sequence, resulting in a final coding sequence of MCGPG(VPGxG)nWPGSG (SEQ ID NO: 13), where n is 31 to 671 pentamer repeats. All constructs were confirmed by DNA sequencing (Eurofins Genomics).

For expression and purification, pET25b+vectors encoding ELP proteins were transformed into E. coli BLR (DE3). All proteins were purified by inverse transition cycling. Briefly, 500 mL of E. coli BLR (DE3) bacterial cultures were grown in TB dry media for 18-20 hours in 2 L flasks. Cells were harvested by centrifugation, lysed by sonication, and nucleic acids were precipitated with polyethyleneimine and removed by centrifugation. NaCl was added to the soluble lysate to a concentration of 200 mg/mL, and the solution was heated at 47° C. until the ELP precipitated. The precipitated ELP was collected by centrifugation, re-dissolved in cold PBS, centrifuged at 4° C. to remove any un-dissolved precipitate, and this heat cycling process was repeated 2 times. ELP was once more precipitated and re-dissolved in a cold solution of 25% ethanol in PBS, centrifuged at 4° C. to remove any un-dissolved precipitate, precipitated again and resuspended in cold PBS. Purity was assessed by SDS-PAGE on a 4-20% Mini-PROTEAN TGX Stain-Free gel.

Figure 14A:
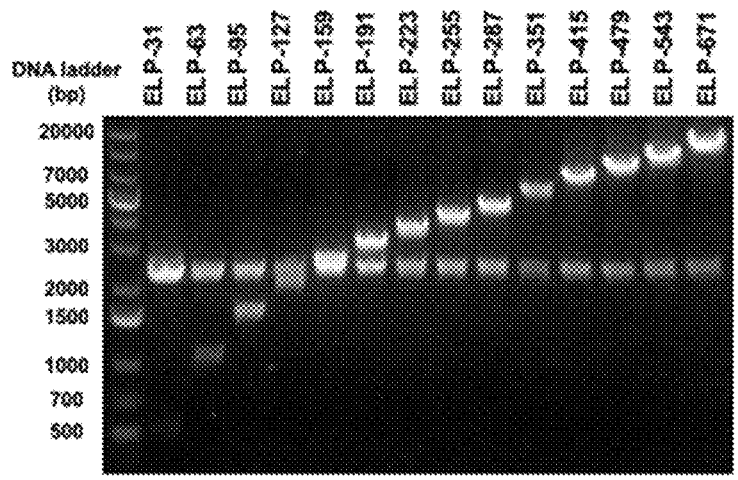
FIGS. 14A-B show images illustrating assessment of ELP expression constructs and protein expression. (A) Evaluation of ELP coding DNA size. (B) Evaluation of expressed peptide molecular weight.

In FIG. 14A, the synthesized ELP coding DNAs were digested and their size evaluated on an agarose gel. The band at 2.5 kb is the vector backbone, and the band increasing in size is the ELP insert ranging from 480 bp to 10,080 bp corresponding to 31 to 671 ELP repeated units.

Figure 14B:
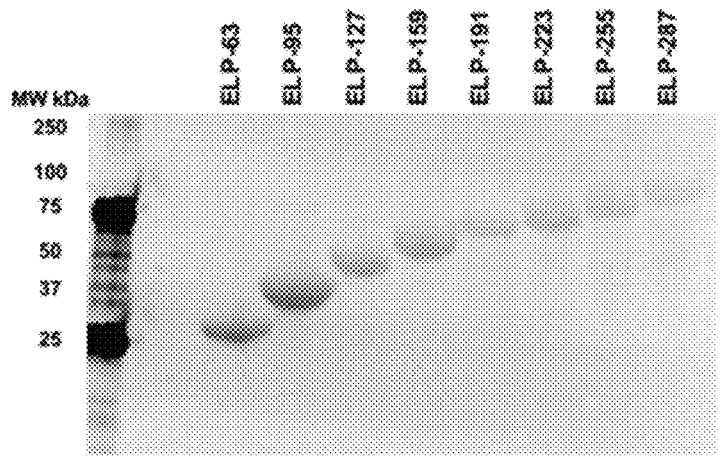

These synthesized DNA constructs were expressed in recombinant expression systems. As shown in FIG. 14B, the recombinant expression system was sufficient for successful production and purification using thermal precipitation of the peptides having sizes between 25 kDa and 110 kDa, corresponding to ELP-63 to ELP-287. ELP protein purity was assessed by SDS-PAGE and visualized using fluorescence imaging of Mini-PROTEAN TGX Stain-Free gels. Proteins were obtained at high purity, and each migrated at the expected molecular weight on an SDS-PAGE gel.

Following purification, proteins ranging from 25 kDa to 110 kDa were characterized in vitro to determine their transition temperature ($T_t$) and hydrodynamic radius ($R_h$) by turbidity assay and dynamic light scattering, respectively.

The determination of the transition temperature of ELP constructs was performed as follows. ELP samples in phosphate buffered saline were filtered through a Millex-GV hydrophilic Durapore (PVDF) filter with a pore size of 0.22 µm. 10 µM of filtered protein solution was heated at a constant rate of 0.5° C./min in a temperature-controlled multicell holder in a UV-visible spectrophotometer (Cary 100) and the turbidity of the solution was measured as absorbance at 350 nm. The transition temperature ($T_t$) was determined as the temperature at which a maximum was observed in a plot of the first derivative of the turbidity trace using GraphPad Prism version 7.00 for Windows.

The hydrodynamic radius of ELP constructs was measured as follows. 10 µm of filtered (0.22 µm) protein solution was evaluated by dynamic and static light scattering using DynaPro NanoStar (Wyatt Technology) with laser wavelength of 663.53 nm. Batch measurements were performed at a constant temperature of 20° C., the signal acquisition period was set to 5 s, and an averaged result of 10 acquisitions was taken as a measurement. A total of 3 measurements was done. The refractive index increment do/dc for protein was set to 0.185. Data were analyzed using Dynamics software (Wyatt Technology) using a Mw-R model of linear polymers and a static light scattering conformation model of random coil. Radius (nm) and % Mass were expressed as the mean value of the peak of the size distribution from the Regularization Graph using the Coils model in Dynamics.

Figure 15A:
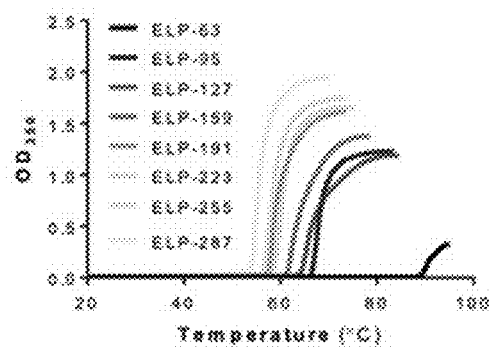
FIGS. 15A-F show graphs illustrating determination of the transition temperature and hydrodynamic radius of ELP constructs. (A) Turbidity profiles of ELP proteins. (B) Transition temperature $T_t$ as a function of ELP molecular weight. (C) Nonlinear regression plot of transition temperature in B. (D) Percent mass of ELP as a function of radius. (E) Radius as a function of ELP molecular weight. (F) Nonlinear regression plot of radius in E.
Figure 15B:
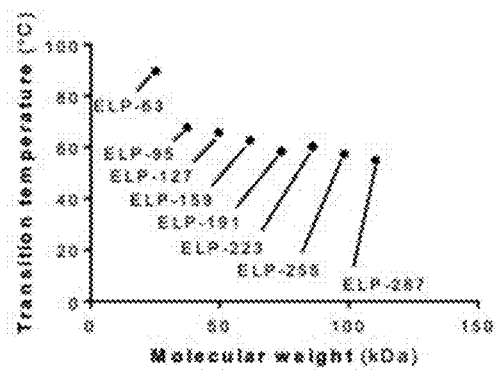
Figure 15C:
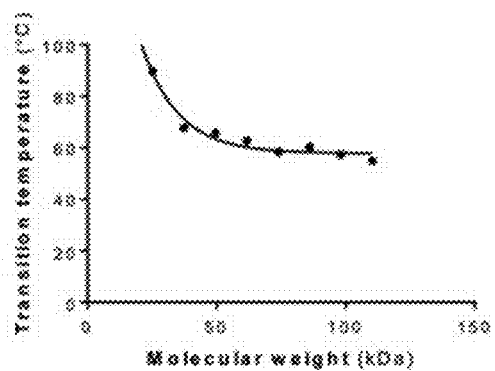
Figure 15D:
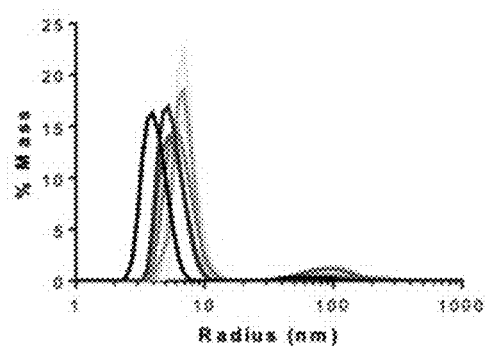
Figure 15E:
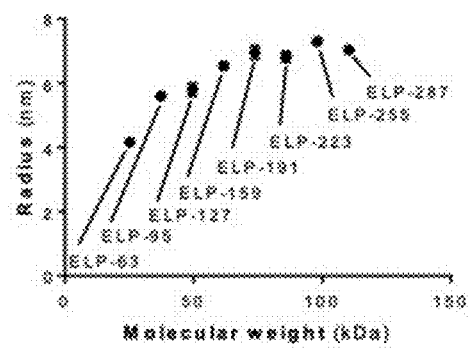
Figure 15F:
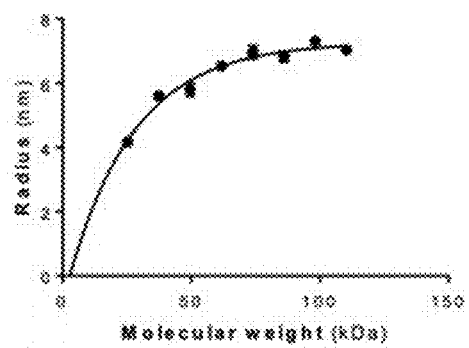

FIG. 15A shows the turbidity profiles (Abs 350 nm) of ELP proteins (10 µM in PBS, 0.22 µm filtered), obtained at a heating rate of 0.5° C./min. In FIGS. 15B-C, the transition temperature $T_t$ is plotted as a function of ELP molecular weight (MW) fit by nonlinear regression using Prism (GraphPad) to a one-phase exponential decay function. $T_t$ was determined as the peak of the first derivative of turbidity. In FIGS. 15D-F, the radius, size distribution and estimated relative amount of mass in each peak of species was obtained by dynamic light scattering while the hydrodynamic radius $R_h$ as a function of ELP MW fit was determined by nonlinear regression using Prism (GraphPad) to a one-phase exponential decay function in FIG. 15F.

It was found that with an increase in MW of the ELP protein, the $T_t$ of each protein decreased until it neared an asymptote at 54° C. for the 110 kDa (FIG. 15C). In addition, their radius increased with an increase in MW in the size range from 25 kDa to 110 kDa. Yet, hydrodynamic radius reached an asymptote for the 98 kDa and larger proteins at 7 nm (FIGS. 15D-F). Detailed $T_t$ and hydrodynamic radius data are reported in Table 2.

TABLE 2

Parameters of ELP constructs obtained by turbidity and dynamic light scattering assays.

| Protein | Predicted protein MW (kDa) | Transition temperature (° C.) | Radius (nm) |
|---|---|---|---|
| ELP-63 | 25.2475 | 89.745 | 4.170 ± 0.056 |
| ELP-95 | 37.3972 | 67.795 | 5.600 ± 0.030 |
| ELP-127 | 49.5469 | 65.775 | 5.800 ± 0.200 |
| ELP-159 | 61.696 | 62.745 | 6.530 ± 0.115 |

TABLE 2-continued

Parameters of ELP constructs obtained by turbidity
and dynamic light scattering assays.

| Protein | Predicted protein MW (kDa) | Transition temperature (° C.) | Radius (nm) |
|---|---|---|---|
| ELP-191 | 73.8463 | 58.370 | 6.967 ± 0.208 |
| ELP-223 | 85.996 | 60.250 | 6.830 ± 0.169 |
| ELP-255 | 98.1457 | 57.295 | 7.300 ± 0.100 |
| ELP-287 | 110.2955 | 54.920 | 7.33 ± 0.058 |

Example 4. Assessment of ELP Stability of Proteins with Varying Molecular Weights To determine the stability of polypeptides, 50 μM of each fluorescently labeled ELP was incubated in PBS or plasma at 4 or 37° C. for up to 10 days. Fluorophore loss from polypeptides was assessed by measuring fluorescence before and after precipitation of the proteins with 20% TCA. Fluorescence levels after TCA were corrected for dilution and compared to the pre-precipitation fluorescence to calculate the percentage of free dye at each time point. Polypeptide degradation was further assessed by SDS-PAGE on a Bolt 4-12% Bis-Tris Plus gels in reducing conditions for PBS samples and non-reducing conditions for plasma samples. Gels were visualized by direct fluorescence imaging using an IVIS Spectrum (PerkinElmer) and analyzed using Living Image Software. Fluorescence was measured as total radiant efficiency for both the total lane area including the ELP band and the lane area under the ELP band. The percentage of the sample that was degraded was determined by dividing the band intensity below the ELP band by the total band intensity. All calculations were corrected by the signal present at time 0 in order to account for any signal present as lower molecular weight species prior to the incubations. As a control, fluorescently labeled protein was hydrolyzed using a method modified from Zhong, et al. 15 μM of fluorescently labeled protein was resuspended in 500 μl of 25% aqueous trifluoroacetic acid (TFA) solution. 10 μl of protein solution was placed in 1.5 ml polypropylene centrifuge tube, capped and sealed with a Teflon tape. Sample was microwave irradiated for 10 min, followed by vacuum centrifugation (Savant Speed Vac Concentrator) to remove the acid which was repeated until an adequate amount of the protein was hydrolyzed. Hydrolyzed protein was resuspended in $H_2O$, and the sample was prepared for SDS-PAGE analysis.

Each ELP protein was fluorescently labeled on its N-terminal cysteine residue using a maleimide conjugate of rhodamine. Proteins were diluted to 200 μmol/L in 50 mM $NaH_2PO_4$ pH 7 buffer, and tris-(2-carboxyethyl) phosphine (TCEP) was added to a 10-fold molar excess. Tetramethylrhodamine-5-maleimide (Molecular Probes) was added to a 2-fold molar excess and the reaction was allowed to proceed overnight at 4° C. Unreacted dye was removed by multiple washes with an Amicon 3,000 molecular weight cutoff spin filter (Merck Millipore). Labeling efficiency was assessed by UV-visible spectrophotometry (NanoDrop 2000, Thermo Fisher Scientific, Waltham, Mass.). Removal of unreacted label was confirmed by trichloroacetic acid (TCA) precipitation of the labeled protein and assessing the free fluorophore levels in the supernatant spectrophotometrically.

Figure 16A:
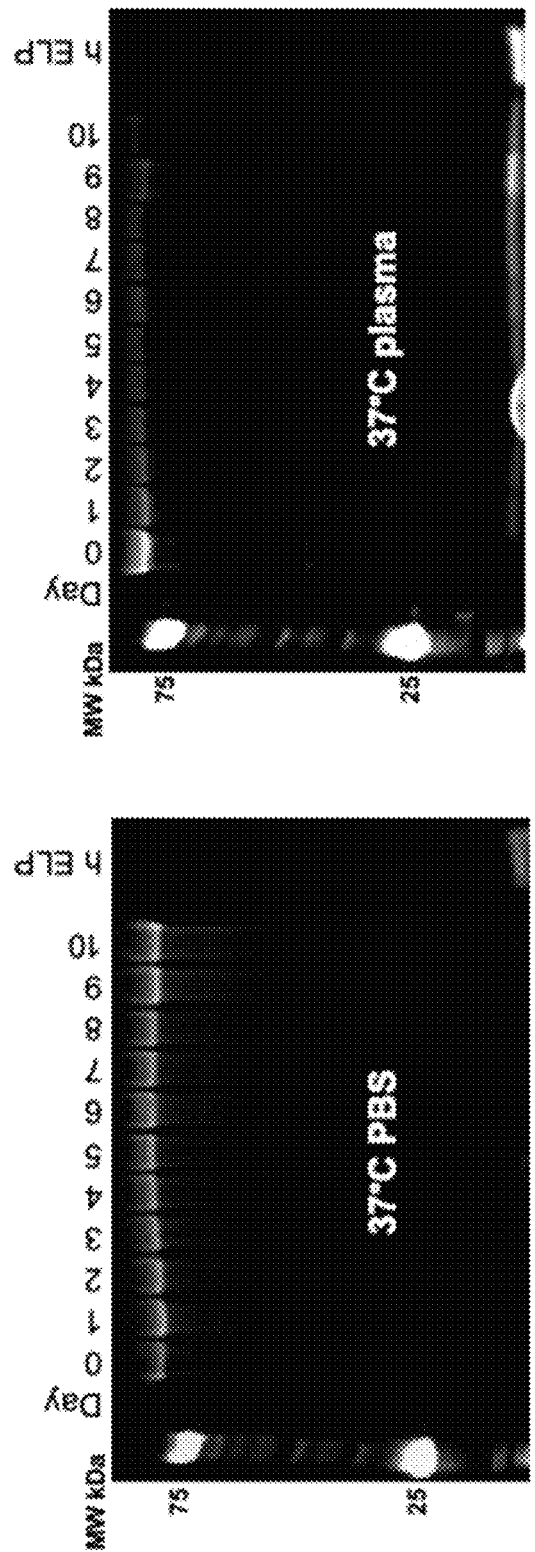
FIGS. 16A-C show images and graphs illustrating the stability of ELP constructs. (A) Representative gels demonstrating stability of 86 kDa ELP in PBS (left) and plasma (right) at 37° C. (B) Degradation of ELPs in PBS (left) and plasma (right) at 4° C. (top) and 37° C. (bottom). (C) Free dye released from fluorescently-labeled ELP in PBS (left) and plasma (right) at 4° C. (top) and 37° C. (bottom).
Figure 16B:
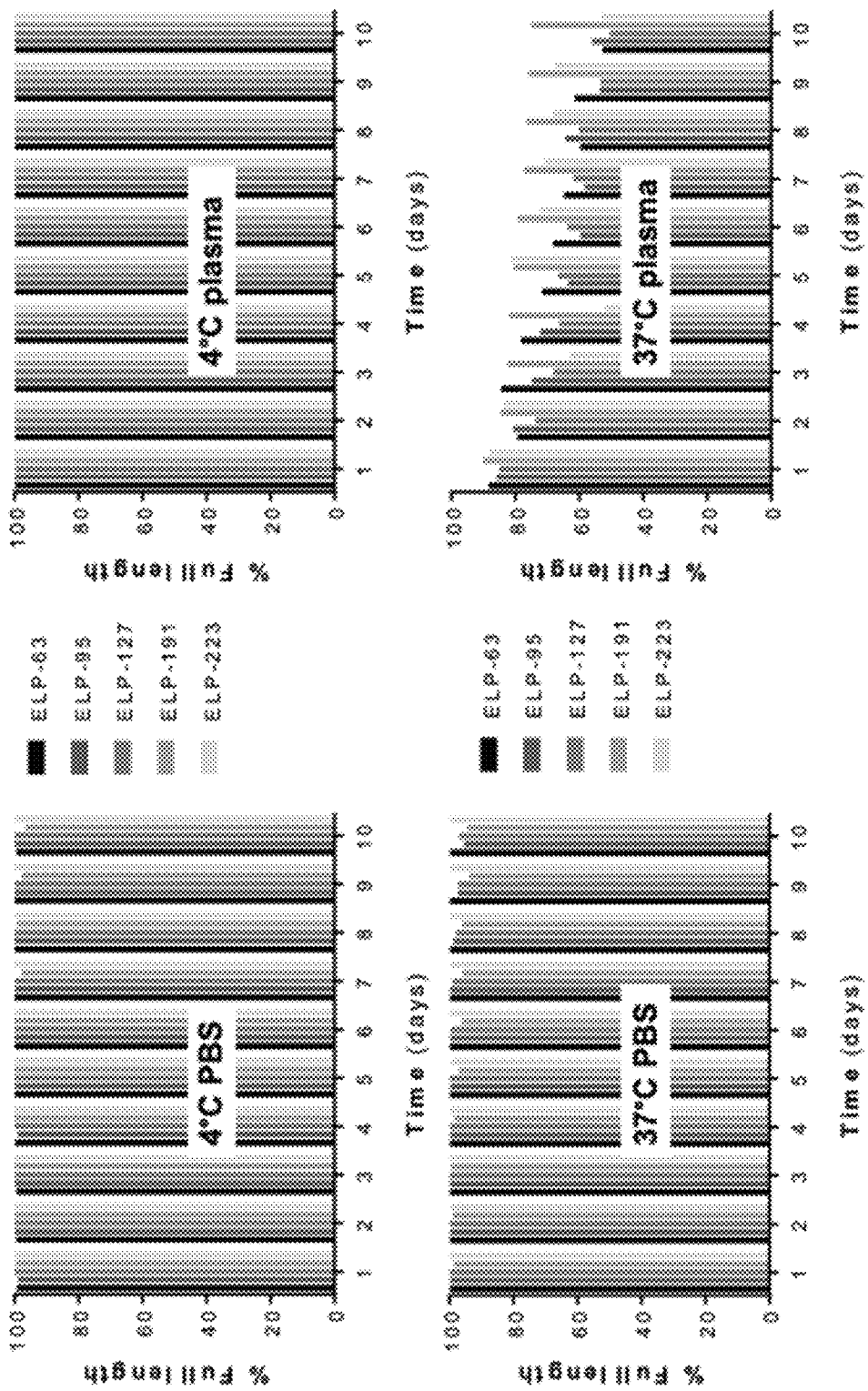

ELP stability was assessed in vitro by determining the percent of fluorescently labeled full length polypeptide present after up to 10 days of incubation in either PBS or plasma at 4 or 37° C., and by determining the percent of dye released from the polypeptide. Five ELP proteins were selected with a range of MW from 25 to 86 kDa. A representative example gel is shown in FIG. 16A of the results from the 86 kDa protein at 37° C. All polypeptides proved to be stable in PBS at both 4 and 37° C., and in plasma at 4° C., with only minimal degradation detected at very late time points (FIG. 16B). The SDS-PAGE gel shown is for ELP-223 (86 kDa) with hydrolyzed ELP (KELP) as a positive control and visualized by direct fluorescence imaging of the fluorescently-labeled ELP.

Some degradation of the polypeptides was observed when incubated in plasma at 37° C. (FIG. 16B, lower right). Polypeptide stability was quantified from the SDS-PAGE analysis for all sizes of ELP proteins. About 80-90% of the proteins were still present as full-length protein on day 1, and each showed a slow degradation over the ten-day time course. On day 10 for ELP-63, ELP-95, ELP-127, ELP-191 and ELP-223, the percent of full length was 53, 56, 51, 75 and 53%, respectively.

Figure 16C:
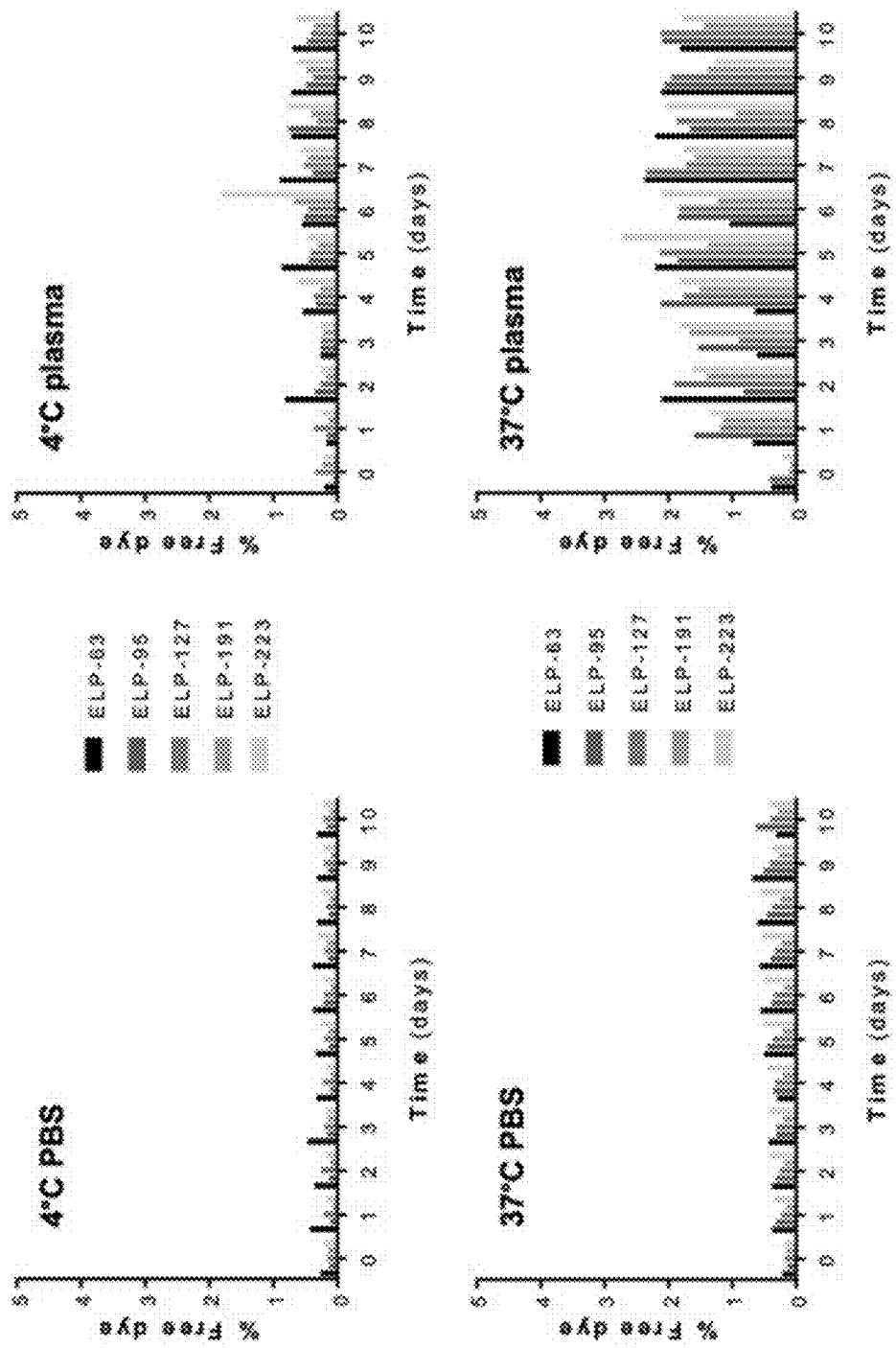

In FIG. 16C, free dye release from the fluorescently-labeled ELP did not exceed 4% in conditions tested, even in the 37° C. plasma samples, as shown by fluorophore loss evaluated using direct fluorescence measurements. These results indicated that even after significant degradation had occurred, the dye was still bound to a protein component.

Example 5. Plasma and Tissue Clearance Pharmacokinetics of ELP Proteins with Varying Molecular Weights A chronic biodistribution study was conducted in SKH1 Elite hairless female mice to determine the effects of MW on plasma pharmacokinetics and total tissue levels of ELP. For pharmacokinetic and biodistribution experiments, five different sized ELPs were selected ranging in MW from 25 to 86 kDa (Table 1).

Animal studies were approved by the Animal Care and Use Committee of the University of Mississippi Medical Center and conducted according to the guidelines of the Guide for the Care and Use of Laboratory Animals. SKH1-Elite hairless female mice (Charles River) were anesthetized with isoflurane (1-3%, to effect), administered carprofen (5 mg/kg subcutaneous), and injected with rhodamine-labeled polypeptides (1.5 μmol/kg) by intravenous injection into the femoral vein. Blood was sampled by tail prick intermittently for 48 hours, collected in Greiner Bio-One MiniCollect capillary blood collection tubes, and plasma was collected after centrifugation.

Plasma samples were analyzed for concentration of the polypeptides using quantitative fluorescence analysis. The fluorescence intensity of 2 μl of plasma was measured in a fluorescence plate reader on a NanoQuant Plate (Tecan) using an excitation wavelength of 535 nm and an emission wavelength 585 nm with Magellan software. Fluorescence of the plasma samples was compared to standard curves generated from known concentrations of the injected protein, which allows for comparison of multiple proteins regardless of the fluorescence labeling efficiency of each. A two-compartment model was fitted to the pooled data (mean concentration ±SD versus time; n=4 except ELP-127 where n=6) to develop a predictive mathematical model of the plasma concentration versus time.

Whole body fluorescence was measured at the same time as each blood sample by collecting dorsal view images of the live animal using, an IVIS Spectrum. Images were collected using 535-nm excitation and 580-nm emission filters, auto exposure, and small binning. Using Living Image software, regions of interest were drawn over the entire animal, and mean radiant efficiency was measured to determine whole body fluorescence intensity. Standard curves of each injected protein were pipetted into a black 96-well plate, which was subsequently imaged with identical imaging parameters. Mean tissue fluorescence was fit to these standard curves to correct for any differences in labeling levels among polypeptides.

Figure 17A:
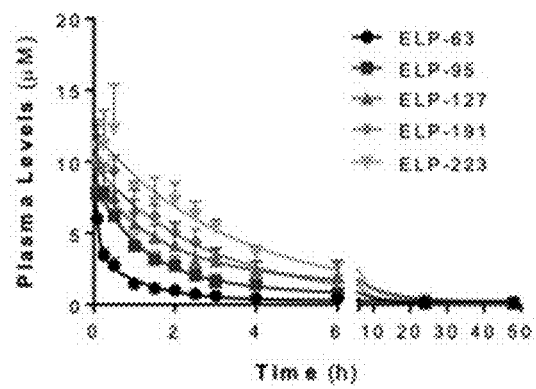
FIGS. 17A-C show graphs illustrating plasma and tissue pharmacokinetics and tissue biodistribution of ELP constructs. (A) Two-compartment pharmacokinetic model of plasma clearance after bolus intravenous injection. (B) Whole-animal fluorescence with time following injection. (C) Tissue accumulation following injection.

After bolus intravenous injection, plasma clearance was fit to a two-compartment pharmacokinetic model (FIG. 17A). This study clearly demonstrated that an increase in MW resulted in slower plasma clearance in vivo. The terminal half-life of the smallest protein, ELP-63 (25 kDa), was 0.84 h, and was directly proportional to MW (Pearson's correlation coefficient r=0.9375, n=5, p=0.0186). The largest protein, ELP-223 (86 kDa), had a terminal half-life of 16.99 h, a 20-fold increase. The distribution half-life was directly proportional to MW (Pearson's correlation coefficient r=0.9929, n=5, p=0.0.0007). Detailed pharmacokinetic analysis of each protein is shown in Table 3. These data demonstrate that the size of the ELP (which can be finely controlled by varying the number of VPGXG (SEQ ID NO: 1) repeats) can be used to tune the plasma half-life. For example, smaller ELPs could be used for drug delivery applications in which fast plasma clearance is desired. Conversely, large ELP carriers could be used to extend the half-life of fused therapeutic agents in therapeutic applications for which a longer plasma and tissue half-life is desired.

Mice were euthanized and major organs removed to quantify ELP tissue levels. Organ biodistribution was assessed with a two-way ANOVA for factors of polypeptide treatment and organ type with post hoc Tukey's multiple comparison. Kidney levels were assessed for differences between treatment groups with a one-way ANOVA with post hoc Tukey's multiple comparison. Correlation was evaluated by Pearson's correlation coefficient. All analyses were done using Prism (GraphPad), and a p value of <0.05 was considered statistically significant.

Figure 17B:
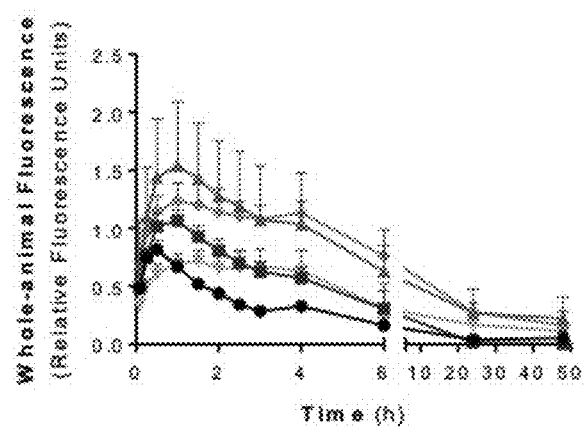
Figure 17C:
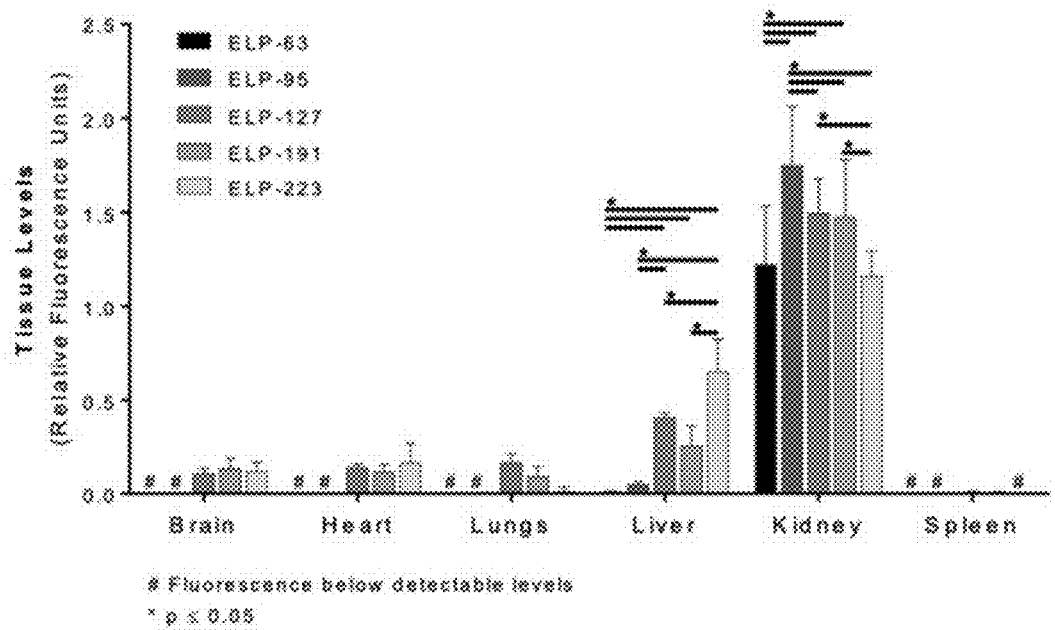

As shown in FIG. 17C, all ELP proteins accumulated most strongly in the kidneys regardless of their MW. The smallest proteins, the 25 kDa ELP-63 and the 37 kDa ELP-95, had either very low or below detectable levels in the brain, heart, lungs, liver and spleen. Statistically significant differences were denoted by * between indicated groups as assessed by a two-way ANOVA with post hoc Tukey's multiple comparison, p<0.05. Polypeptide levels below detectable levels was denoted by #.

The most remarkable finding was the effect of MW on deposition of ELP in the kidney. Renal deposition exhibited a non-linear relationship with MW (Pearson's correlation coefficient r=−0.3079, n=5, p=0.6142, $R^2$=0.09481), with the mid-sized proteins accumulating in the kidneys at the highest levels. ELP-63 levels, 1.22 relative fluorescence units (RFU), were significantly lower than ELP-95, 1.75 RFU, ELP-127, 1.49 RFU, and ELP-191 1.47 RFU. ELP-95 levels were additionally higher than ELP-127, ELP-191 and ELP-223 levels. ELP-127 levels were also significantly higher than ELP-223 levels, 1.16 RFU (Two-way ANOVA

TABLE 3

Pharmacokinetics of Different MW ELP Constructs in Mice.

|  |  | ELP-63 (25 kDa) | ELP-95 (37 kDa) | ELP-127 (50 kDa) | ELP-191 (74 kDa) | ELP-223 (86 kDa) |
|---|---|---|---|---|---|---|
| $V_c$ | (L) | 0.004183 | 0.004996 | 0.00442 | 0.004603 | 0.00364 |
| Cl | $\left(\frac{L}{h}\right)$ | 0.00801 | 0.00219 | 0.00105 | 0.00115 | 0.00079 |
| AUC | $\left(\frac{\mu mol \times h}{L}\right)$ | 4.76 | 19.83 | 37.15 | 38.72 | 55.92 |
| $t_{1/2,dist}$ | (h) | 0.07 | 0.77 | 1.07 | 1.97 | 2.27 |
| $t_{1/2,term}$ | (h) | 0.84 | 4.66 | 7.05 | 21.11 | 16.99 |

$V_c$: Central Compartment Volume of Distribution;
Cl: Plasma Clearance;
AUC: Area Under Curve;
$t_{1/2,dist}$: Distribution Half-Life;
$t_{1/2,term}$: Terminal Half-Life.

Whole-animal clearance kinetics was determined by non-invasive in vivo imaging of entire mice at each time point. Interestingly, whole-animal fluorescence, depicting tissue levels of fluorescently labeled ELP, increased for the first 30 minutes after injection of the smallest ELP-63, then began to decrease as the protein cleared the body (FIG. 17B). Increasing MW lead to a shift of the tissue clearance curve to the right. ELP-63 peaked at 30 minutes and ELP-223 at 90 min. The ELP proteins with MW above 37 kDa cleared tissue more slowly and were still detectable in the body even 48 h after injection.

An acute biodistribution study was conducted to determine organ levels of ELP proteins with varying MW. The biodistribution of ELP proteins were measured at 4 hours after intravenous injection of fluorescently labeled ELP.

with post hoc Tukey's multiple comparison, $F(4, 90)$=8.74, p<0.0001). The liver was the only other organ where all five of the ELP proteins were detected at noteworthy levels (although significantly lower than kidney levels), and liver levels increased with increasing MW.

Example 6. Intrarenal Localization of ELPs

For acute tissue biodistribution studies, SKH1-Elite hairless female mice were anesthetized with isoflurane (1-3%, to effect), administered carprofen (5 mg/kg subcutaneous), and given a single bolus dose of rhodamine-labeled polypeptides (1.5 µmol/kg) by intravenous injection into the femoral vein. Mice were allowed to rouse from anesthesia and move freely in the cage for four hours following injection. They were then re-anesthetized and euthanized while still under anesthesia, and their organs collected for whole organ fluorescence biodistribution analysis (n=4 mice per agent). All major organs were imaged ex vivo using an IVIS Spectrum. Tissues were then embedded in freezing medium (Tissue-Plus O.C.T Compound) and flash frozen. Kidneys were cut into 14 μm sections with a cryostat. Sections were first scanned using a fluorescence slide scanner ScanArray Express (Packard BioScience) using excitation wavelengths 543 nm and emission wavelength 570 nm, scan resolution 50 1.tm, and full scan speed for quantitative scans; and scan resolution 5 μm and half scan speed for high resolution scans. For quantitative scans, the mean fluorescence intensity of tissue sections was analyzed with ImageJ software, and the measured fluorescence intensity was fit to a standard curve of each protein (made from known concentrations of the same labeling batch used for animal injections).

Sections were further analyzed by confocal microscopy. Slides were equilibrated to room temperature and either stained with Hoechst 33342 (5 μg/ml in PBS) or imaged without processing. Stained sections were covered by a coverslip, sealed and imaged immediately by laser scanning confocal microscopy (Nikon C2+) using, 405- and 561-nm lasers for excitation of Hoechst 33342 and rhodamine-labeled protein, respectively. Unprocessed sections were imaged by confocal microscopy image stitching using, 561-nm laser. Brightness levels were adjusted for image quality and don't represent actual intensity.

Figure 18A:
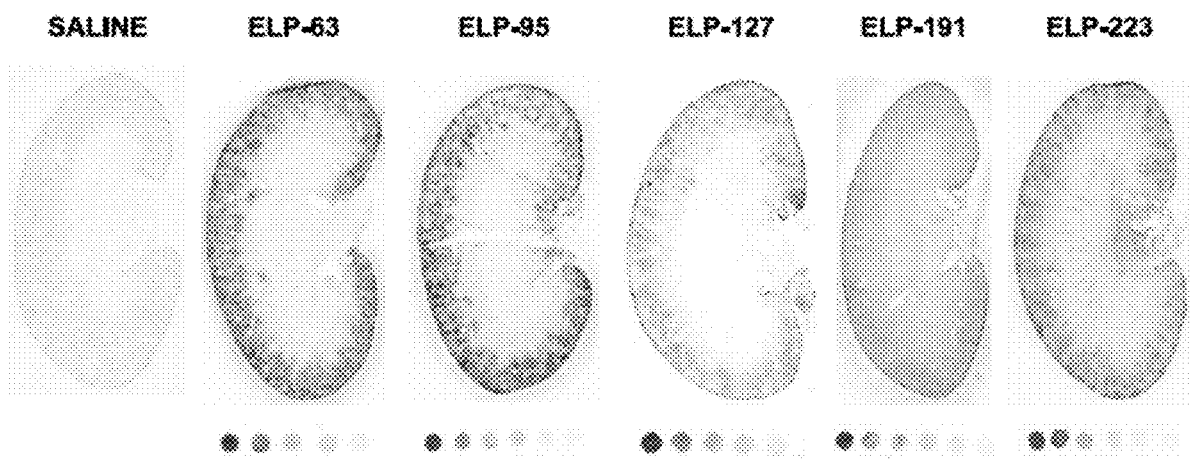
FIGS. 18A-B show an image and a graph illustrating quantitative analysis of ELP intrarenal levels. (A) Quantitative fluorescence histology of kidney sections showing intra-renal concentrations and distribution of ELPs. (B) Accumulation of various ELPs in the renal cortex and renal medulla.

In addition to whole organ ex vivo imaging, quantitative fluorescence histology of kidney sections was performed to accurately measure intra-renal concentrations and to determine the intra-renal distribution. Scans of kidney sections revealed that the smaller ELP-63 and ELP-95 localized were exclusively in the renal cortex (FIG. 18A).

With an increase in MW, the ELP proteins became more distributed in the medulla. Quantitation of these data revealed that the cortical ELP concentration was highest for the smallest proteins, reaching an intra-cortical concentration of around 4 μM at the dose used, and significantly decreasing to around 2 μM for the largest proteins (one-way ANOVA with post hoc Tukey's multiple comparison, F (4, 15)=6.753, p=0.0026; Pearson's correlation coefficient r=−0.8938, n=5, p=0.0409).

Concomitant with the decrease in cortical levels, the medullary ELP levels significantly increased as the polymer size increased (FIG. 18B), from around 0.07 μM for ELP-63 to around 0.84 μM for ELP-223 (one-way ANOVA with post hoc Tukey's multiple comparison, F(4, 15)=5.247, p=0.0076; Pearson's correlation coefficient r=0.7325, n=5, p=0.1593).

Figure 19A:
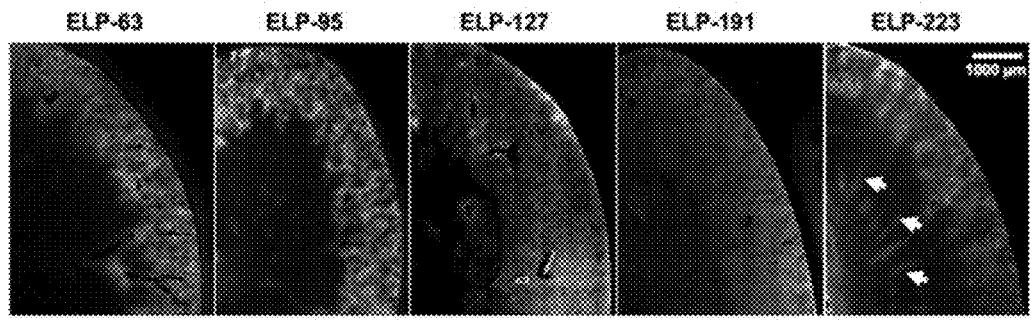
FIGS. 19A-B show images illustrating intrarenal distribution of ELP constructs. (A) Confocal microscopy showing localization of ELPs. (B) Higher magnification imaging with nuclear co-staining showing location of ELP within the renal cortex.
Figure 19B:
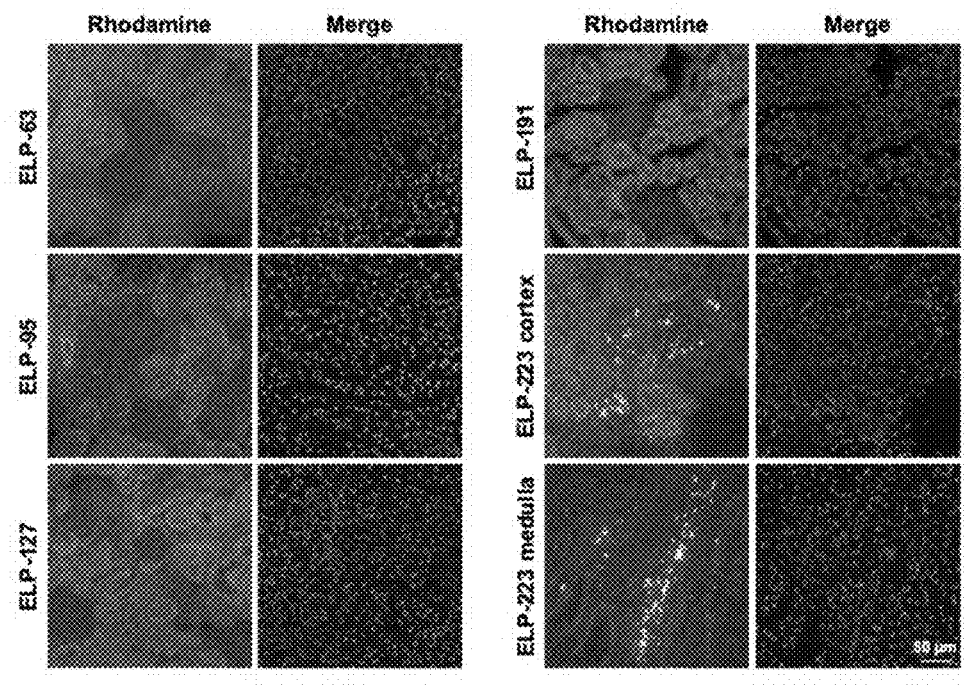

This was confirmed by confocal microscopy of unprocessed slides, shown in FIG. 19A. The smallest ELPs localized cortically and appeared to be mostly present in the renal tubules. As the size increased, the medullary levels increased, and the largest construct, ELP-223, was detectable in distinct medullary structures (FIG. 19A, arrows). Higher magnification imaging with nuclear co-staining revealed that in the cortex, all ELP proteins other than ELP-223 were mostly localized in the tubular epithelial cells, with lower levels in the glomeruli (FIG. 19B). The 86 kDa ELP-223, however, formed aggregates in the glomeruli, and high-resolution images revealed that the distinct medullary signal seen in the slide scanning data was actually protein aggregates in medullary structures (FIG. 19B, right panel middle and bottom).

Figure 18B:
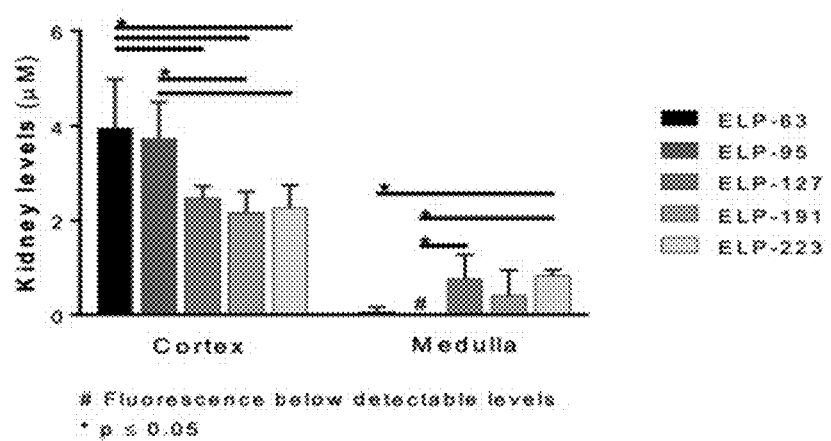

Surprisingly, in addition to differences in organ biodistribution and stability of different size ELP constructs, these results demonstrated that the intra-renal localization of ELP constructs can be targeted exclusively to the cortical region of the kidney if the ELP construct contains about 95 repeat units or less, whose ELP proteins have a MW of 38 kDa or less (FIG. 18B). While in contrast, those ELP constructs containing greater than about 95 repeat units, whose ELP proteins have a MW of 38 kDa or more, showed a renal localization in both the cortical and medullary regions. Further, these data found the amount of ELP protein shifted from cortex to medulla as the size of ELP increased above 38 kDa.

The differential localization of the different size ELP open new strategies in the targeting of therapeutic delivery of biological or chemically based molecules used for the treatment of diseases having distinct disorder profiles, such as renovascular disease or cancer present in the kidney.

Starting with ELP, it was coupled to the therapeutic agent that may be a peptide or protein or protein fragment or nucleic acid or small molecule drug known to have therapeutic activity in renal vascular diseases or cancer. In addition to altering the physical properties of the ELP carrier itself, other attributes of the ELP coupled therapeutic agent are designed. To further optimize the drug delivery to the kidney, in vivo targeting was accomplished by the inclusion of targeting sequences or peptides on the ELP carrier coupled to the targeting agent. The targeting agent may be a peptide, protein, antibody, aptamer, or small molecule with a specific molecular target in the kidney. Further, it also may also contain a cell penetrating peptide, other peptide, or protein capable of penetrating the cellular membrane.

Other modifications of the drug delivery system included a drug binding domain to allow attachment of known or new small molecule therapeutic agents to improve their delivery to treat renal disorders. The drug binding domain may be attached to the ELP carrier via a drug release domain to allow for selective release of the drug under particular environmental conditions or at specific sites within the body. In other delivery vehicles, the ELP coupled therapeutic system includes multiple copies of the therapeutic agent and/or drug binding domain to increase the amount of drug delivered. This may also include the use of 2 or more different therapeutic agents or different drugs attached to the drug binding domain(s) to achieve combination therapy. Other cases may include both a therapeutic agent(s) and a drug binding domain(s) to achieve simultaneous delivery of peptide/protein—based therapeutic agents with small molecule drugs.

Throughout this document, various references are mentioned. All such references are incorporated herein by reference, including the references set forth in the following list.

REFERENCES

1. Kagan H M, Tseng L, Trackman P C, et al. (1980) Repeat polypeptide models of elastin as substrates for lysyl oxidase. J Biol Chem 255:3656-9.
2. Luan C H, Parker T M, Prasad K U, Urry D W (1991) Differential scanning calorimetry studies of NaCl effect on the inverse temperature transition of some elastin-based polytetra-, polypenta-, and polynonapeptides. Biopolymers 31:465-75. doi: 10.1002/bip.360310502
3. McPherson D T, Morrow C, Minehan D S, et al. (1992) Production and purification of a recombinant elastomeric polypeptide, G-(VPGVG)19-VPGV, from *Escherichia coli*. Biotechnol Prog 8:347-52. doi: 10.1021/bp00016a012

4. Rousselle C, Clair P, Lefauconnier J M, et al. (2000) New advances in the transport of doxorubicin through the blood-brain barrier by a peptide vector-mediated strategy. Mol Pharmacol 57:679-86.
5. Vives E, Brodin P, Lebleu B (1997) A truncated HIV-1 Tat protein basic domain rapidly translocates through the plasma membrane and accumulates in the cell nucleus. J Biol Chem 272:16010-7.
6. Pasqualini R, Ruoslahti E (1996) Organ targeting in vivo using phage display peptide libraries. Nature 380:364-6. doi: 10.1038/380364a0
7. National Institutes of Health, National Institute of Diabetes and Digestive and Kidney Diseases (2013) U.S. Renal Data System, USRDS 2013 Annual Data Report: Atlas of Chronic Kidney Disease and End-Stage Renal Disease in the United States.
8. Ritchie J, Green D, Chrysochou C, et al. (2014) High-risk clinical presentations in atherosclerotic renovascular disease: prognosis and response to renal artery revascularization. Am J Kidney Dis Off J Natl Kidney Found 63:186-197. doi: 10.1053/j.ajkd.2013.07.020
9. Textor S C, Lerman L O (2014) Reality and renovascular disease: when does renal artery stenosis warrant revascularization? Am J Kidney Dis Off J Natl Kidney Found 63:175-177. doi: 10.1053/j.ajkd.2013.11.004
10. Textor S C, Misra S, Oderich G S (2013) Percutaneous revascularization for ischemic nephropathy: the past, present, and future. Kidney Int 83:28-40. doi: 10.1038/ki.2012.363
11. Cooper C J, Murphy T P, Cutlip D E, et al. (2014) Stenting and medical therapy for atherosclerotic renal-artery stenosis. N Engl J Med 370:13-22. doi: 10.1056/NEJMoa1310753
12. Chade A R, Kelsen S (2010) Renal microvascular disease determines the responses to revascularization in experimental renovascular disease. Circ Cardiovasc Interv 3:376-383. doi: 10.1161/CIRCINTERVENTIONS.110.951277
13. Chade A R, Kelsen S (2012) Reversal of renal dysfunction by targeted administration of VEGF into the stenotic kidney: a novel potential therapeutic approach. Am J Physiol Ren Physiol 302:F1342-50. doi: 10.1152/ajprenal.00674.2011
14. Iliescu R, Fernandez S R, Kelsen S, et al. (2010) Role of renal microcirculation in experimental renovascular disease. Nephrol Dial Transplant Off Publ Eur Dial Transpl Assoc—Eur Ren Assoc 25:1079-1087. doi: 10.1093/ndt/gfp605
15. Chade A R, Zhu X, Lavi R, et al. (2009) Endothelial progenitor cells restore renal function in chronic experimental renovascular disease. Circulation 119:547-557. doi: 10.1161/CIRCULATIONAHA.108.788653

What is claimed is:

1. A renal medulla and cortex targeting elastin-like polypeptide (ELP) comprising:
   between 223 and 671 repeat units having the sequence VPGXG (SEQ ID NO: 1);
   wherein X in each of the repeat units is individually selected from the group consisting of any amino acid except proline.

2. The ELP of claim 1, wherein the ELP comprises between 300 and 671 of the repeat units.

3. The ELP of claim 1, wherein the ELP comprises between 400 and 671 of the repeat units.

4. The ELP of claim 1, wherein the ELP comprises between 500 and 671 of the repeat units.

5. The ELP of claim 1, wherein the ELP comprises a molecular weight of at least 86 kDa.

6. The ELP of claim 1, wherein the ELP comprises a molecular weight of between 86 kDa and 257 kDa.

7. The ELP of claim 1, wherein the distribution of amino acids at the X position in the VPGXG repeat units includes V:G:A in a 1:4:3 ratio.

8. The ELP of claim 1, further comprising one or more of a group selected from a therapeutic agent or agents, a drug binding domain, a targeting domain, and a cell penetrating peptide.

9. A method of treating a renal disorder, the method comprising:
   administering an elastin-like peptide (ELP) and a therapeutic drug to a subject in need thereof;
   wherein the ELP includes between 223 and 671 repeat units having the sequence VPGXG (SEQ ID NO: 1); and
   wherein X in each of the repeat units is individually selected from the group consisting of any amino acid except proline.

10. The method of claim 9, wherein the ELP comprises between 300 and 671 of the repeat units.

11. The method of claim 9, wherein the ELP comprises between 400 and 671 of the repeat units.

* * * * *